(12) United States Patent
Fischell et al.

(10) Patent No.: US 11,759,608 B2
(45) Date of Patent: Sep. 19, 2023

(54) INTRAVASCULAR FLUID CATHETER WITH MINIMAL INTERNAL FLUID VOLUME

(71) Applicant: Ablative Solutions, Inc., San Jose, CA (US)

(72) Inventors: David R. Fischell, Fair Haven, NJ (US); Tim A. Fischell, Kalamazoo, MI (US)

(73) Assignee: Ablative Solutions, Inc., Wakefield, MA (US)

( * ) Notice: Subject to any disclaimer, the term of this patent is extended or adjusted under 35 U.S.C. 154(b) by 664 days.

(21) Appl. No.: 16/805,033

(22) Filed: Feb. 28, 2020

(65) Prior Publication Data

US 2020/0269015 A1 Aug. 27, 2020

Related U.S. Application Data

(63) Continuation of application No. 13/643,065, filed as application No. PCT/US2012/051906 on Aug. 22, (Continued)

(51) Int. Cl.
*A61M 25/00* (2006.01)
*A61M 25/06* (2006.01)
(Continued)

(52) U.S. Cl.
CPC .... *A61M 25/0084* (2013.01); *A61M 25/0074* (2013.01); *A61M 25/0108* (2013.01); (Continued)

(58) Field of Classification Search
CPC .......... A61M 25/0086; A61M 25/0108; A61M 2025/0087; A61M 2025/0093; (Continued)

(56) References Cited

U.S. PATENT DOCUMENTS 3,119,391 A 1/1964 Harrison
3,924,617 A 12/1975 Ferro
(Continued)

FOREIGN PATENT DOCUMENTS

CA 2799505 11/2011
CN 1147964 4/1997
(Continued)

OTHER PUBLICATIONS

U.S. Appl. No. 16/561,599, filed Sep. 5, 2019, Fischell et al.
(Continued)

*Primary Examiner* — Kami A Bosworth
(74) *Attorney, Agent, or Firm* — Knobbe, Martens, Olson & Bear, LLP

(57) ABSTRACT

A catheter-based/intravascular ablation (denervation) system includes a multiplicity of needles which expand open around a central axis to engage the wall of a blood vessel, or the wall of the left atrium, allowing the injection of a cytotoxic or/or neurotoxic solution for ablating conducting tissue, or nerve fibers around the ostium of the pulmonary vein, or circumferentially in or just beyond the outer layer of the renal artery. The expandable needle delivery system is formed with self-expanding materials and include structures, near the end portion of the needles, or using separate guide tubes. The system also includes means to limit and/or adjust the depth of penetration of the ablative fluid into the tissue of the wall of the targeted blood vessel. The preferred embodiment of the catheter delivered through the vascular system of a patient includes a multiplicity of expandable guide tubes that engage the wall of a blood vessel. Injection needles having injection egress at or near their sharpened distal end are then advanced through the guide tubes to penetrate the wall of the blood vessel to a prescribed depth. The ability to provide PeriVascular injection so as to only
(Continued)

affect the outer layer(s) of a blood vessel without affecting the media has particular application for PeriVascular Renal Denervation (PVRD) of the sympathetic nerves which lie in the adventitia or outside the adventitia of the renal artery.

20 Claims, 31 Drawing Sheets

Related U.S. Application Data 2012, now Pat. No. 10,576,246, which is a continuation-in-part of application No. 13/294,439, filed on Nov. 11, 2011, now abandoned, which is a continuation-in-part of application No. 13/216,495, filed on Aug. 24, 2011, now Pat. No. 9,278,196, said application No. PCT/US2012/051906 is a continuation-in-part of application No. 13/216,495, filed on Aug. 24, 2011, now Pat. No. 9,278,196.

(51) Int. Cl.
 *A61M 25/01* (2006.01)
 *A61B 5/00* (2006.01)

(52) U.S. Cl.
 CPC ....... *A61M 25/0662* (2013.01); *A61B 5/6848* (2013.01); *A61M 25/0097* (2013.01); *A61M 2025/0039* (2013.01); *A61M 2025/0086* (2013.01); *A61M 2025/0087* (2013.01); *A61M 2025/0681* (2013.01); *A61M 2202/0468* (2013.01); *A61M 2210/12* (2013.01)

(58) Field of Classification Search
 CPC .. A61M 2025/0095; A61M 2205/3303; A61M 2205/3317; A61M 2025/0086; A61B 5/6848; A61B 5/6849; A61B 5/685; A61B 18/1492; A61B 2018/00577; A61B 2018/143; A61B 2018/1475
 See application file for complete search history.

(56) References Cited

U.S. PATENT DOCUMENTS

| | | |
|---|---|---|
| 4,578,061 A | 3/1986 | Lemelson |
| 4,798,595 A | 1/1989 | Anderson et al. |
| 5,203,777 A | 4/1993 | Lee |
| 5,304,141 A | 4/1994 | Johnson et al. |
| 5,354,279 A | 10/1994 | Hofling |
| 5,385,562 A | 1/1995 | Adams et al. |
| 5,405,376 A | 4/1995 | Mulier et al. |
| 5,419,777 A | 5/1995 | Hofling |
| 5,431,649 A | 7/1995 | Mulier et al. |
| 5,464,395 A | 11/1995 | Faxon et al. |
| 5,474,102 A | 12/1995 | Lopez |
| 5,551,426 A | 9/1996 | Hummel et al. |
| 5,588,960 A | 12/1996 | Edwards et al. |
| 5,662,606 A | 9/1997 | Cimino et al. |
| 5,667,488 A | 9/1997 | Lundquist et al. |
| 5,672,173 A | 9/1997 | Gough |
| 5,683,384 A | 11/1997 | Gough |
| 5,685,322 A | 11/1997 | Sung et al. |
| 5,713,863 A | 2/1998 | Vigil et al. |
| 5,792,094 A | 8/1998 | Stevens et al. |
| 5,800,379 A | 9/1998 | Edwards |
| 5,800,484 A | 9/1998 | Gough et al. |
| 5,855,576 A | 1/1999 | LeVeen et al. |
| 5,902,289 A | 5/1999 | Swartz et al. |
| 5,971,958 A | 10/1999 | Zhang |
| 5,980,516 A | 11/1999 | Mulier et al. |
| 6,006,755 A | 12/1999 | Edwards |
| 6,056,744 A | 5/2000 | Edwards |
| 6,106,521 A | 8/2000 | Blewett et al. |
| 6,165,164 A | 12/2000 | Hill et al. |
| 6,190,353 B1 | 2/2001 | Makower et al. |
| 6,190,393 B1 | 2/2001 | Bevier et al. |
| 6,217,554 B1 | 4/2001 | Green |
| 6,221,049 B1 | 4/2001 | Selmon et al. |
| 6,231,597 B1 | 5/2001 | Deem et al. |
| 6,254,599 B1 | 7/2001 | Lesh et al. |
| 6,277,107 B1 | 8/2001 | Lurie et al. |
| 6,283,947 B1 | 9/2001 | Mirzaee |
| 6,283,951 B1 | 9/2001 | Flaherty et al. |
| 6,302,870 B1 | 10/2001 | Jacobsen et al. |
| 6,375,660 B1 | 4/2002 | Fischell et al. |
| 6,416,510 B1 | 7/2002 | Altman et al. |
| 6,432,092 B2 | 8/2002 | Miller |
| 6,478,778 B1 | 11/2002 | Jacobsen et al. |
| 6,514,248 B1 | 2/2003 | Eggers et al. |
| 6,547,803 B2 | 4/2003 | Seward et al. |
| 6,599,267 B1 | 7/2003 | Ray et al. |
| 6,610,054 B1* | 8/2003 | Edwards .................. A61N 1/40 606/41 |
| 6,652,517 B1 | 11/2003 | Hall et al. |
| 6,685,648 B2 | 2/2004 | Flaherty et al. |
| 6,692,466 B1 | 2/2004 | Chow et al. |
| 6,764,461 B2 | 7/2004 | Mickley et al. |
| 6,854,467 B2 | 2/2005 | Boekstegers |
| 6,855,124 B1 | 2/2005 | Gonzalez et al. |
| 6,905,480 B2 | 6/2005 | McGuckin et al. |
| 6,951,549 B1* | 10/2005 | Beyerlein .............. A61B 5/053 607/116 |
| 6,966,897 B2 | 11/2005 | Shimazaki |
| 6,978,174 B2 | 12/2005 | Gelfand et al. |
| 6,997,903 B2 | 2/2006 | Wijay et al. |
| 7,015,253 B2 | 3/2006 | Escandon et al. |
| 7,056,286 B2 | 6/2006 | Ravenscroft et al. |
| 7,087,040 B2 | 8/2006 | McGuckin, Jr. et al. |
| 7,094,202 B2 | 8/2006 | Nobis et al. |
| 7,162,303 B2 | 1/2007 | Levin et al. |
| 7,181,288 B1 | 2/2007 | Rezai et al. |
| 7,273,469 B1 | 9/2007 | Chan et al. |
| 7,326,238 B1 | 2/2008 | Kilpatrick |
| 7,422,587 B2 | 9/2008 | Bek et al. |
| 7,472,705 B2 | 1/2009 | Baran |
| 7,617,005 B2 | 11/2009 | Demarais et al. |
| 7,621,945 B2 | 11/2009 | Lennox et al. |
| 7,635,353 B2 | 12/2009 | Gurusamy et al. |
| 7,647,115 B2 | 1/2010 | Levin et al. |
| 7,653,438 B2 | 1/2010 | Deem et al. |
| 7,666,163 B2 | 2/2010 | Seward et al. |
| 7,691,080 B2 | 4/2010 | Seward et al. |
| 7,691,086 B2 | 4/2010 | Tkebuchava |
| 7,717,899 B2 | 5/2010 | Bowe et al. |
| 7,717,948 B2 | 5/2010 | Demarais et al. |
| 7,744,584 B2 | 6/2010 | Seward et al. |
| 7,756,583 B2 | 7/2010 | Demarais et al. |
| 7,794,444 B2 | 9/2010 | Lesh et al. |
| 7,850,656 B2 | 12/2010 | McKay et al. |
| 7,862,563 B1 | 1/2011 | Cosman et al. |
| 7,873,417 B2 | 1/2011 | Demarais et al. |
| 7,881,807 B2 | 2/2011 | Schaer |
| 7,942,854 B1 | 5/2011 | Von Oepen et al. |
| 8,000,764 B2 | 8/2011 | Rashidi |
| 8,088,127 B2 | 1/2012 | Mayse et al. |
| 8,100,883 B1 | 1/2012 | Johnson |
| 8,131,371 B2 | 3/2012 | Demarals et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,758 B2 | 4/2012 | Chan et al. |
| 8,152,804 B2 | 4/2012 | Elmouelhi et al. |
| 8,175,711 B2 | 5/2012 | Demarais et al. |
| 8,396,548 B2 | 3/2013 | Perry et al. |
| 8,399,443 B2 | 3/2013 | Seward et al. |
| 8,465,451 B2 | 6/2013 | McRae et al. |
| 8,465,752 B2 | 6/2013 | Seward |
| 8,663,190 B2 | 3/2014 | Fischell et al. |
| 8,684,998 B2 | 4/2014 | Demarais et al. |

(56) References Cited

U.S. PATENT DOCUMENTS

| | | |
|---|---|---|
| 8,708,995 B2 | 4/2014 | Seward et al. |
| 8,740,849 B1 | 6/2014 | Fischell et al. |
| 8,771,252 B2 | 7/2014 | Gelfand et al. |
| 8,852,163 B2 | 10/2014 | Deem et al. |
| 8,880,186 B2 | 11/2014 | Levin et al. |
| 8,934,978 B2 | 1/2015 | Deem et al. |
| 8,948,865 B2 | 2/2015 | Zarins et al. |
| 8,975,233 B2 | 3/2015 | Stein et al. |
| 8,979,801 B2 | 3/2015 | Lamson et al. |
| 8,983,595 B2 | 3/2015 | Levin et al. |
| 9,011,879 B2 | 4/2015 | Seward |
| 9,023,095 B2 | 5/2015 | Bueche et al. |
| 9,056,185 B2 | 6/2015 | Fischell et al. |
| 9,125,661 B2 | 9/2015 | Deem et al. |
| 9,131,978 B2 | 9/2015 | Zarins et al. |
| 9,131,983 B2 | 9/2015 | Fischell et al. |
| 9,138,281 B2 | 9/2015 | Zarins et al. |
| 9,179,962 B2 | 11/2015 | Fischell et al. |
| 9,192,715 B2 | 11/2015 | Gelfand et al. |
| 9,199,065 B2 | 12/2015 | Seward |
| 9,237,925 B2 | 1/2016 | Fischell et al. |
| 9,254,360 B2 | 2/2016 | Fischell et al. |
| 9,265,558 B2 | 2/2016 | Zarins et al. |
| 9,278,196 B2 | 3/2016 | Fischell et al. |
| 9,289,255 B2 | 3/2016 | Deem et al. |
| 9,301,795 B2 | 4/2016 | Fischell et al. |
| 9,308,044 B2 | 4/2016 | Zarins et al. |
| 9,314,630 B2 | 4/2016 | Levin et al. |
| 9,320,561 B2 | 4/2016 | Zarins et al. |
| 9,320,850 B2 | 4/2016 | Fischell et al. |
| 9,326,817 B2 | 5/2016 | Zarins et al. |
| 9,439,726 B2 | 9/2016 | Zarins et al. |
| 9,456,869 B2 | 10/2016 | Zarins et al. |
| 9,474,563 B2 | 10/2016 | Zarins et al. |
| 9,486,270 B2 | 11/2016 | Zarins et al. |
| 9,526,827 B2 | 12/2016 | Fischell et al. |
| 9,539,047 B2 | 1/2017 | Fischell et al. |
| 9,554,849 B2 | 1/2017 | Fischell et al. |
| 9,629,675 B2 | 4/2017 | Kleshinski et al. |
| 9,636,174 B2 | 5/2017 | Zarins et al. |
| 9,675,413 B2 | 6/2017 | Deem et al. |
| 9,743,983 B2 | 8/2017 | Levin et al. |
| 9,757,192 B2 | 9/2017 | Levin et al. |
| 9,789,276 B2 | 10/2017 | Seward et al. |
| 9,795,441 B2 | 10/2017 | Fischell et al. |
| 9,814,873 B2 | 11/2017 | Zarins et al. |
| 9,895,195 B2 | 2/2018 | Zarins et al. |
| 9,907,611 B2 | 3/2018 | Levin et al. |
| 9,931,046 B2 | 4/2018 | Fischell et al. |
| 9,949,652 B2 | 4/2018 | Fischell et al. |
| 9,993,278 B2 | 6/2018 | Rioux et al. |
| 10,022,059 B2 | 7/2018 | Fischell et al. |
| 10,118,004 B2 | 11/2018 | Fischell et al. |
| 10,172,663 B2 | 1/2019 | Fischell et al. |
| 10,226,278 B2 | 3/2019 | Fischell et al. |
| 10,350,392 B2 | 7/2019 | Fischell et al. |
| 10,405,912 B2 | 9/2019 | Fischell et al. |
| 10,420,481 B2 | 9/2019 | Fischell et al. |
| 10,485,951 B2 | 11/2019 | Fischell et al. |
| 10,517,666 B2 | 12/2019 | Fischell et al. |
| 10,576,246 B2 | 3/2020 | Fischell et al. |
| 10,736,524 B2 | 8/2020 | Fischell et al. |
| 10,736,656 B2 | 8/2020 | Fischell et al. |
| 10,849,685 B2 | 12/2020 | Denison et al. |
| 10,881,312 B2 | 1/2021 | Fischell et al. |
| 10,881,458 B2 | 1/2021 | Fischell et al. |
| 10,945,787 B2 | 3/2021 | Fischell et al. |
| 11,007,008 B2 | 5/2021 | Fischell et al. |
| 11,007,329 B2 | 5/2021 | Fischell et al. |
| 11,007,346 B2 | 5/2021 | Fischell et al. |
| 11,202,889 B2 | 12/2021 | Fischell et al. |
| 11,510,729 B2 | 11/2022 | Fischell et al. |
| 2001/0037065 A1 | 11/2001 | Graf et al. |
| 2002/0002349 A1 | 1/2002 | Flaherty et al. |
| 2002/0010439 A1 | 1/2002 | Miller |
| 2002/0052577 A1 | 5/2002 | Shimazaki et al. |
| 2002/0082584 A1 | 6/2002 | Rosenman et al. |
| 2002/0120238 A1 | 8/2002 | McGuckin et al. |
| 2002/0120261 A1 | 8/2002 | Morris et al. |
| 2002/0151866 A1 | 10/2002 | Lundkvist et al. |
| 2002/0177846 A1 | 11/2002 | Mulier et al. |
| 2002/0183738 A1 | 12/2002 | Chee et al. |
| 2003/0009095 A1 | 1/2003 | Skarda |
| 2003/0032929 A1 | 2/2003 | McGuckin, Jr. |
| 2003/0171723 A1 | 9/2003 | Ponzi |
| 2004/0019310 A1 | 1/2004 | Hogendijk |
| 2004/0064098 A1 | 4/2004 | Cuschieri et al. |
| 2004/0133154 A1 | 7/2004 | Flaherty et al. |
| 2004/0147902 A1 | 7/2004 | McGuckin, Jr. et al. |
| 2004/0158143 A1 | 8/2004 | Flaherty et al. |
| 2005/0010203 A1 | 1/2005 | Edwards et al. |
| 2005/0070885 A1 | 3/2005 | Nobis et al. |
| 2005/0096647 A1 | 5/2005 | Steinke et al. |
| 2005/0187546 A1 | 8/2005 | Bek et al. |
| 2005/0234437 A1 | 10/2005 | Baxter et al. |
| 2005/0245923 A1 | 11/2005 | Christopherson et al. |
| 2005/0288730 A1 | 12/2005 | Deem et al. |
| 2006/0064056 A1 | 3/2006 | Coyle et al. |
| 2006/0064065 A1 | 3/2006 | Russo |
| 2006/0173440 A1 | 8/2006 | Lamson et al. |
| 2006/0189940 A1 | 8/2006 | Kirsch |
| 2006/0200121 A1 | 9/2006 | Mowery |
| 2006/0224118 A1 | 10/2006 | Morris et al. |
| 2006/0271111 A1 | 11/2006 | Demarais et al. |
| 2006/0271135 A1 | 11/2006 | Minar et al. |
| 2006/0282048 A1 | 12/2006 | Kimura et al. |
| 2006/0293647 A1 | 12/2006 | Mcrea et al. |
| 2007/0005018 A1 | 1/2007 | Tekbuchava |
| 2007/0060812 A1 | 3/2007 | Harel et al. |
| 2007/0083239 A1 | 4/2007 | Demarias et al. |
| 2007/0129720 A1 | 6/2007 | Demarais et al. |
| 2007/0129760 A1 | 6/2007 | Demarais et al. |
| 2007/0173899 A1 | 7/2007 | Levin et al. |
| 2007/0185483 A1 | 8/2007 | Butty et al. |
| 2007/0203549 A1 | 8/2007 | Demarais et al. |
| 2007/0244479 A1 | 10/2007 | Beatty et al. |
| 2007/0270751 A1 | 11/2007 | Stangenes |
| 2007/0270757 A1 | 11/2007 | Willis et al. |
| 2008/0039786 A1 | 2/2008 | Epstein et al. |
| 2008/0045890 A1 | 2/2008 | Seward et al. |
| 2008/0051756 A1 | 2/2008 | Makower et al. |
| 2008/0125709 A1 | 5/2008 | Chang et al. |
| 2008/0135443 A1 | 6/2008 | Frojd et al. |
| 2008/0161790 A1 | 7/2008 | Dando et al. |
| 2008/0188812 A1 | 8/2008 | Valaie |
| 2008/0213331 A1 | 9/2008 | Gelfand et al. |
| 2008/0300454 A1 | 12/2008 | Goto |
| 2009/0018526 A1 | 1/2009 | Power |
| 2009/0018638 A1 | 1/2009 | Shirley et al. |
| 2009/0036948 A1 | 2/2009 | Levin et al. |
| 2009/0076500 A1 | 3/2009 | Azure |
| 2009/0312617 A1 | 12/2009 | Creed et al. |
| 2010/0076545 A1 | 3/2010 | Kleshinski et al. |
| 2010/0114087 A1 | 5/2010 | Edwards |
| 2010/0137860 A1 | 6/2010 | Demarais et al. |
| 2010/0137952 A1 | 6/2010 | Demarais et al. |
| 2010/0179416 A1 | 7/2010 | Hoey et al. |
| 2010/0191112 A1 | 7/2010 | Demarais et al. |
| 2010/0222851 A1 | 9/2010 | Deem et al. |
| 2010/0268307 A1 | 10/2010 | Demarais et al. |
| 2010/0298948 A1 | 11/2010 | Hoey et al. |
| 2010/0305546 A1 | 12/2010 | Seward et al. |
| 2010/0324446 A1 | 12/2010 | Pendleton |
| 2011/0009848 A1 | 1/2011 | Woodard et al. |
| 2011/0104060 A1 | 5/2011 | Seward |
| 2011/0104061 A1 | 5/2011 | Seward |
| 2011/0112400 A1 | 5/2011 | Emery et al. |
| 2011/0146674 A1 | 6/2011 | Roschak |
| 2011/0172593 A1 | 7/2011 | Lyyikainen et al. |
| 2011/0182912 A1 | 7/2011 | Evans et al. |
| 2011/0184337 A1 | 7/2011 | Evans et al. |
| 2011/0195971 A1 | 8/2011 | Cincotta |
| 2011/0202098 A1 | 8/2011 | Demarais et al. |
| 2011/0207758 A1 | 8/2011 | Sobotka et al. |

(56) References Cited

U.S. PATENT DOCUMENTS

| | | |
|---|---|---|
| 2011/0208096 A1 | 8/2011 | Demarais et al. |
| 2011/0257564 A1 | 10/2011 | Demarais et al. |
| 2011/0257622 A1 | 10/2011 | Salahieh et al. |
| 2011/0295354 A1 | 12/2011 | Bueche et al. |
| 2012/0010524 A1 | 1/2012 | Fojtik et al. |
| 2012/0041419 A1 | 2/2012 | Blanchard et al. |
| 2012/0053604 A1 | 3/2012 | DiCaprio |
| 2012/0071832 A1 | 3/2012 | Bunch |
| 2012/0083877 A1 | 4/2012 | Nguyen et al. |
| 2012/0101490 A1 | 4/2012 | Smith |
| 2012/0108517 A1 | 5/2012 | Evans et al. |
| 2012/0116438 A1 | 5/2012 | Salahieh et al. |
| 2012/0130269 A1 | 5/2012 | Rea |
| 2012/0130289 A1 | 5/2012 | Demarais et al. |
| 2012/0130345 A1 | 5/2012 | Levin et al. |
| 2012/0143181 A1 | 6/2012 | Demarais et al. |
| 2012/0197198 A1 | 8/2012 | Demarais et al. |
| 2012/0197252 A1 | 8/2012 | Deem et al. |
| 2012/0253186 A1 | 10/2012 | Simpson et al. |
| 2012/0253192 A1 | 10/2012 | Cressman |
| 2012/0271277 A1 | 10/2012 | Fischell et al. |
| 2012/0271301 A1 | 10/2012 | Fischell et al. |
| 2012/0296329 A1 | 11/2012 | Ng |
| 2013/0053792 A1 | 2/2013 | Fischell et al. |
| 2013/0053821 A1 | 2/2013 | Fischell et al. |
| 2013/0053822 A1 | 2/2013 | Fischell et al. |
| 2013/0090637 A1 | 4/2013 | Sliwa |
| 2013/0103026 A1 | 4/2013 | Kleshinski et al. |
| 2013/0131743 A1 | 5/2013 | Yamasaki et al. |
| 2013/0138082 A1 | 5/2013 | Salahieh et al. |
| 2013/0144251 A1 | 6/2013 | Sobotka |
| 2013/0178910 A1 | 7/2013 | Azamian et al. |
| 2013/0274614 A1 | 10/2013 | Shimada et al. |
| 2013/0274673 A1 | 10/2013 | Fischell et al. |
| 2013/0274674 A1 | 10/2013 | Fischell et al. |
| 2013/0287698 A1 | 10/2013 | Seward |
| 2014/0024959 A1 | 1/2014 | Sobotka |
| 2014/0025041 A1 | 1/2014 | Fukuoka et al. |
| 2014/0046298 A1 | 2/2014 | Fischell et al. |
| 2014/0121641 A1 | 5/2014 | Fischell et al. |
| 2014/0121644 A1 | 5/2014 | Fischell et al. |
| 2014/0127126 A1 | 5/2014 | Lifton et al. |
| 2014/0236103 A1 | 8/2014 | Fischell et al. |
| 2014/0296708 A1 | 10/2014 | Flaherty et al. |
| 2014/0316351 A1 | 10/2014 | Fischell et al. |
| 2014/0358079 A1 | 12/2014 | Fischell et al. |
| 2014/0378906 A1 | 12/2014 | Fischell et al. |
| 2015/0005719 A1 | 1/2015 | Fischell et al. |
| 2015/0119674 A1 | 4/2015 | Fischell et al. |
| 2015/0119875 A1 | 4/2015 | Fischell et al. |
| 2015/0126965 A1 | 5/2015 | Liungman |
| 2015/0132409 A1 | 5/2015 | Stein et al. |
| 2015/0157405 A1 | 6/2015 | Beeckler |
| 2015/0202220 A1 | 7/2015 | Stein et al. |
| 2015/0224289 A1 | 8/2015 | Seward |
| 2015/0245863 A1 | 9/2015 | Fischell et al. |
| 2015/0335384 A1 | 11/2015 | Fischell et al. |
| 2015/0343156 A1 | 12/2015 | Fischell et al. |
| 2016/0045257 A1 | 2/2016 | Fischell et al. |
| 2016/0058489 A1 | 3/2016 | Fischell et al. |
| 2016/0120587 A1 | 5/2016 | Fischell et al. |
| 2016/0235464 A1 | 8/2016 | Fischell et al. |
| 2016/0242661 A1 | 8/2016 | Fischell et al. |
| 2016/0279384 A1 | 9/2016 | Zarins et al. |
| 2016/0338734 A1 | 11/2016 | Shah et al. |
| 2016/0354137 A1 | 12/2016 | Fischell et al. |
| 2017/0119408 A1 | 5/2017 | Ma |
| 2017/0119974 A1 | 5/2017 | Racz |
| 2017/0290598 A1 | 10/2017 | Culbert et al. |
| 2017/0304594 A1 | 10/2017 | Fischell et al. |
| 2017/0326363 A1 | 11/2017 | Deem et al. |
| 2017/0332926 A1 | 11/2017 | Fischell et al. |
| 2018/0043107 A1 | 2/2018 | Hooven et al. |
| 2018/0071019 A1 | 3/2018 | Fischell et al. |
| 2018/0085554 A1 | 3/2018 | Kassab et al. |
| 2018/0193596 A1 | 7/2018 | Fischell et al. |
| 2018/0279894 A1 | 10/2018 | Fischell et al. |
| 2019/0008580 A1 | 1/2019 | Fischell et al. |
| 2019/0015002 A1 | 1/2019 | Fischell et al. |
| 2019/0076186 A1 | 3/2019 | Fischell et al. |
| 2019/0076187 A1 | 3/2019 | Fischell et al. |
| 2019/0076188 A1 | 3/2019 | Fischell et al. |
| 2019/0117936 A9 | 4/2019 | Fischell et al. |
| 2019/0167918 A1 | 6/2019 | Fischell et al. |
| 2019/0201070 A1 | 7/2019 | Fischell et al. |
| 2019/0269435 A1 | 9/2019 | Fischell et al. |
| 2020/0022751 A1 | 1/2020 | Denison et al. |
| 2020/0061348 A1 | 2/2020 | Fischell et al. |
| 2020/0163566 A1 | 5/2020 | Fischell et al. |
| 2020/0188007 A1 | 6/2020 | Fischell et al. |
| 2020/0188684 A1 | 6/2020 | Wang et al. |
| 2020/0197079 A1 | 6/2020 | Fischell et al. |
| 2020/0197663 A1 | 6/2020 | Fischell et al. |
| 2020/0269015 A1 | 8/2020 | Fischell et al. |
| 2021/0015381 A1 | 1/2021 | Fischell et al. |
| 2021/0015518 A1 | 1/2021 | Fischell et al. |
| 2021/0161594 A1 | 6/2021 | Denison et al. |
| 2021/0204854 A1 | 7/2021 | Fischell et al. |
| 2021/0205011 A1 | 7/2021 | Fischell et al. |
| 2021/0220044 A1 | 7/2021 | Fischell et al. |
| 2021/0290302 A1 | 9/2021 | Fischell et al. |
| 2021/0290860 A1 | 9/2021 | Fischell et al. |
| 2021/0290903 A1 | 9/2021 | Fischell et al. |
| 2022/0031389 A1 | 2/2022 | Fischell et al. |
| 2022/0134062 A1 | 5/2022 | Fischell et al. |

FOREIGN PATENT DOCUMENTS

| | | |
|---|---|---|
| CN | 1269708 | 1/2000 |
| CN | 1290148 | 4/2001 |
| CN | 101518470 | 9/2002 |
| CN | 1494399 | 5/2004 |
| CN | 1927130 | 3/2007 |
| CN | 101888807 | 11/2010 |
| CN | 102274074 | 12/2011 |
| CN | 102413788 | 4/2012 |
| DE | 197 17 253 | 10/1998 |
| EP | 0 797 409 | 10/1997 |
| EP | 0834288 | 4/1998 |
| EP | 1332724 | 8/2003 |
| EP | 0876805 | 8/2006 |
| EP | 2263550 | 7/2015 |
| EP | 2911735 | 9/2015 |
| JP | H06-277294 | 10/1994 |
| JP | H07-524 | 1/1995 |
| JP | H07509389 | 10/1995 |
| JP | H0889582 | 4/1996 |
| JP | 2001527428 | 12/2001 |
| JP | 2002-507458 | 3/2002 |
| JP | 2002510229 | 4/2002 |
| JP | 2002542901 | 12/2002 |
| JP | 2003-510126 | 3/2003 |
| JP | 2004-505689 | 2/2004 |
| JP | 2004516042 | 6/2004 |
| JP | 2004-528062 | 9/2004 |
| JP | 2005-40599 | 2/2005 |
| JP | 2005-506101 | 3/2005 |
| JP | 2008506500 | 3/2008 |
| JP | 09509865 | 3/2009 |
| JP | 2013-517847 | 5/2013 |
| JP | 2015-536186 | 12/2015 |
| JP | 2016-171893 | 9/2016 |
| WO | WO94/04220 | 3/1994 |
| WO | WO 95/13752 | 5/1995 |
| WO | WO 03/049125 | 6/2003 |
| WO | WO 2004/030740 | 4/2004 |
| WO | WO 2006/033989 | 3/2006 |
| WO | WO 2006/084256 | 8/2006 |
| WO | WO 2007/121143 | 10/2007 |
| WO | WO 2009/137819 | 11/2009 |
| WO | WO 2009/141727 | 11/2009 |
| WO | WO 2010/014658 | 2/2010 |
| WO | WO 2010/124120 | 10/2010 |
| WO | WO 2011/094367 | 8/2011 |

(56) References Cited

FOREIGN PATENT DOCUMENTS

| | | |
|---|---|---|
| WO | WO 2012/145300 | 10/2012 |
| WO | WO 2012/145304 | 10/2012 |
| WO | WO 2013/028781 | 2/2013 |
| WO | WO 2013/112844 | 8/2013 |
| WO | WO 2013/159066 | 10/2013 |
| WO | WO 2014/070558 | 5/2014 |
| WO | WO 2015/061614 | 4/2015 |
| WO | WO 2015/168314 | 11/2015 |
| WO | WO 2019/195625 | 10/2019 |
| WO | WO 2022/026105 | 2/2022 |

OTHER PUBLICATIONS

U.S. Appl. No. 16/577,327, filed Sep. 20, 2019, Fischell et al.
U.S. Appl. No. 16/689,604, filed Nov. 20, 2019, Fischell et al.
U.S. Appl. No. 16/717,286, filed Dec. 17, 2019, Fischell et al.
Angelini et al., Retractable-Needle Catheters: An Updated on Local Drug Delivery in Coronary Interventions, Texas Heart Institute Journal, 2008, p. 419-424.
Bello-Reuss et al., Effects of Acute Unilateral Renal Denervation in the Rat, J. of Clinical Investigation, vol. 56, Jul. 1975, p. 208-217.
Berne, Hemodynamics and Sodium Excretion of Denervated Kidney in Anesthetized and Unanesthetized Dog, Am. J. of Physiology, vol. 171, No. 1, Oct. 1952, p. 148-158.
Chinushi et al., "Blood Pressure And Autonomic Responses To Electrical Stimulation Of The Renal Arterial Nerves Before And After Ablation Of The Renal Artery", Hypertension, 2013, vol. 61, p. 450-456.
Dave, R.M., "The ClearWay™ RX Local Therapeutic Infusion Catheter", CathLab Digest, May 2010, vol. 18, No. 5, p. 1-6.
Demas et al., Novel method for localized, functional sympathetic nervous system denervation of peripheral tissue using guanethidine (Journal of Neuroscience Methods 112, 2001), p. 21-28.
Dorward et al., "Reflex Responses To Baroreceptor, Chemoreceptor And Nociceptor Inputs In Single Renal Sympathetic Neurons In The Rabbit And The Effects Of Anaesthesia On Them", Journal of the Autonomic Nervous System, 1987, vol. 18, p. 39-54.
F Mahoud, C Ukena, RE Schmieder. Ambulatory Blood Pressure Changes After Renal Sympathetic Denervation in Patients With Resistant Hypertension. Jul. 8, 2013 AHA Circulation 2013;128:132-140.
Gado et al., "Intra-articular guanethidine injection for resistant shoulder pain: a preliminary double blind study of a novel approach" Annals of the Rheumatic Disease, 1996, p. 199-201.
Habara et al., "Novel Use of a Local Drug Delivery Catheter for Coronary Perforation", Journal of Invasive Cardiology, Jan. 2011, vol. 23, No. 1, p. 1-8.
Hamza et al., "Substantial Reduction In Single Sympathetic Nerve Firing After Renal Denervation In Patients With Resistant Hypertension", Nov. 19, 2012, p. 856-864.
Hsu et al., "The Use of Intravenous Guanethidine Block in the Management of Reflex Sympathtic Dystrophy Syndrome of the Hand." Second Congress of the Hong Kong Orthopaedic Association, Nov. 1982, p. 93-105.
Hering et al., "Substantial Reduction In Single Sympathetic Nerve Firing After Renal Denervation In Patients With Resistant Hypertension", Nov. 19, 2012 in 15 pages.
Klein et al. "Functional reinnervation and development of supersensitivity to NE after renal denervation in rats" American Physiological Society, 1980, p. 353-358.
Klein et al., Effect of Renal Denervation on Arterial Pressure and Renal Norepinephrine Concentration in Wistar-Kyota and Spontaneously Hypersensitive Rats, Can. J. Physiology and Pharmacology, vol. 58, 1980, p. 1384-1388.
Markovic, B., et al., "Embolization With Absolute Ethanol Injection Of Insufficiently Ligated Renal Artery After Open Nephrectomy"; Diagnostic and Interventional Radiology, Mar. 2011; vol. 17, Issue 1, p. 88-91.
"Multi-prong Infusion Needle Case Study", from the web site of peridot™ Precision Manufacturing, http://www.peridotcorp.com/casestudy.aspx, Copyright 2012, in 8 pages.
Nanni et al., Control of Hypertension by Ethanol Renal Ablation (Radiology 148:51-54, Jul. 1983), p. 52-54.
National Institute for Health and Care Excellence. Hypertension in adults: diagnosis and management. Aug. 24, 2011, Nice, CG127.
Owens et al., Percutaneous Peri-Adventitial Guanethidine Delivery Induces Renal Artery Sympathectomy: Preclinical Experience and Implication for Refractory Hypertension (Journal of Vascular Surgery 53:17S), p. 87S, Jun. 2011.
Roytta et al., Taxol-induced neuropathy: short-term effects of local injection (Journal of Neurocytology 13, 1984), p. 685-701.
S.J .Doletskiy et al. "Vysokochastotnaj Elektrotekhnika", M., 7-10 "Meditsina", 1980, p. 48-50, fig. 18-19.
Trostel et al., Do renal nerves chronically influence renal function and arterial pressure in spinal rats? (The American Physiological Society 1992), p. 1265-1270.
Verloop et al., Eligibility for percutaneous renal denervation: the importance of a systematic screening, Journal of Hypertension, 2013, p. 1-7.
Vink et al. Limited destruction of renal nerves after catheter-based renal denervation: results of a human case study, Nephrol Dial Transplant, 2014, p. 1-3.
YA Ashram, NH Abdel Wahab, IH Diab, Non-dipping pattern of nocturnal blood pressure in obstructive sleep apnea syndrom: Possible role of oxidative stress and endothelin-1 precursor. Feb. 14, 2013, Alexandria Journal of Medicine, 49, 153-161.
Zafonte et al., "Phenol and Alcohol Blocks for the Treatment of Spasticity", Physical medicine and rehabilitation clinics of North America, Nov. 2001, p. 817-832.
International Search Report and Written Opinion in PCT/US12/051906 dated Nov. 16, 2012 in 38 pages.
Extended Search Report in EP 12826228 dated Mar. 17, 2015 in 5 pages.
Office Action for Chinese Patent Application 201280051666.9 dated Sep. 22, 2015 in 9 pages.
Office Action for Japanese Patent Application 2014-527272 dated May 17, 2016 in 3 pages.
Office Action for Singapore Patent Application 11201400138Y dated Jun. 2, 2016 in 4 pages.
Office Action for Chinese Patent Application 201280051666.9 dated Jul. 15, 2016 in 7 pages.
Office Action for Chinese Patent Application 201280051666.9 dated Dec. 20, 2016 in 3 pages.
EPO Communication in EP 12826228 dated Mar. 31, 2017 in 4 pages.
Office Action for Japanese Patent Application 2014-527272 dated Apr. 3, 2017 in 6 pages.
Office Action for Chinese Patent Application 201280051666.9 dated Oct. 9, 2017 in 2 pages.
Office Action for Japanese Patent Application 2014-527272 dated Nov. 20, 2017 in 3 pages.
Office Action for Japanese Patent Application 2017-149730 dated Aug. 27, 2018 in 4 pages.
Office Action for Japanese Patent Application 2017-149730 dated Jul. 10, 2019 in 4 pages.
Office Action for Chinese Patent Application 201711417679.4 dated Feb. 19, 2020 in 17 pages.
U.S. Appl. No. 16/945,077, filed Jul. 31, 2020, Fischell et al.
U.S. Appl. No. 17/127,151, filed Dec. 18, 2020, Fischell et al.
U.S. Appl. No. 17/127,443, filed Dec. 18, 2020, Fischell et al.
U.S. Appl. No. 17/173,536, filed Feb. 11, 2021, Fischell et al.
Office Action for Japanese Patent Application 2019-204891 dated Jan. 22, 2021 in 9 pages.
Office Action for Japanese Patent Application 2017-149730 dated Feb. 1, 2021 in 4 pages.
Office Action for Chinese Patent Application 201711417679.4 dated May 25, 2021 in 9 pages.
Office Action for Japanese Patent Application 2019-204891 dated Nov. 15, 2021 in 5 pages.

(56) References Cited

OTHER PUBLICATIONS

Office Action for Japanese Patent Application 2019-204891 dated Jul. 11, 2022 in 4 pages.

* cited by examiner

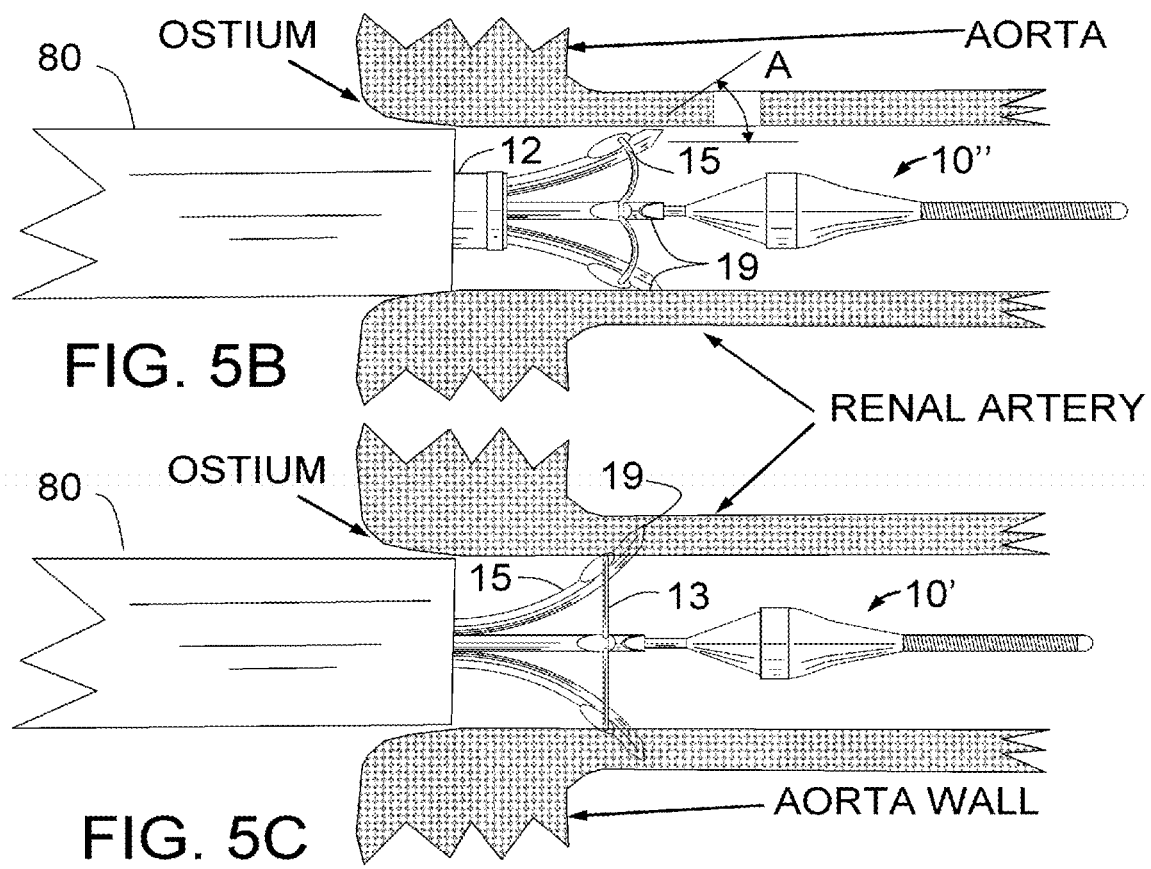

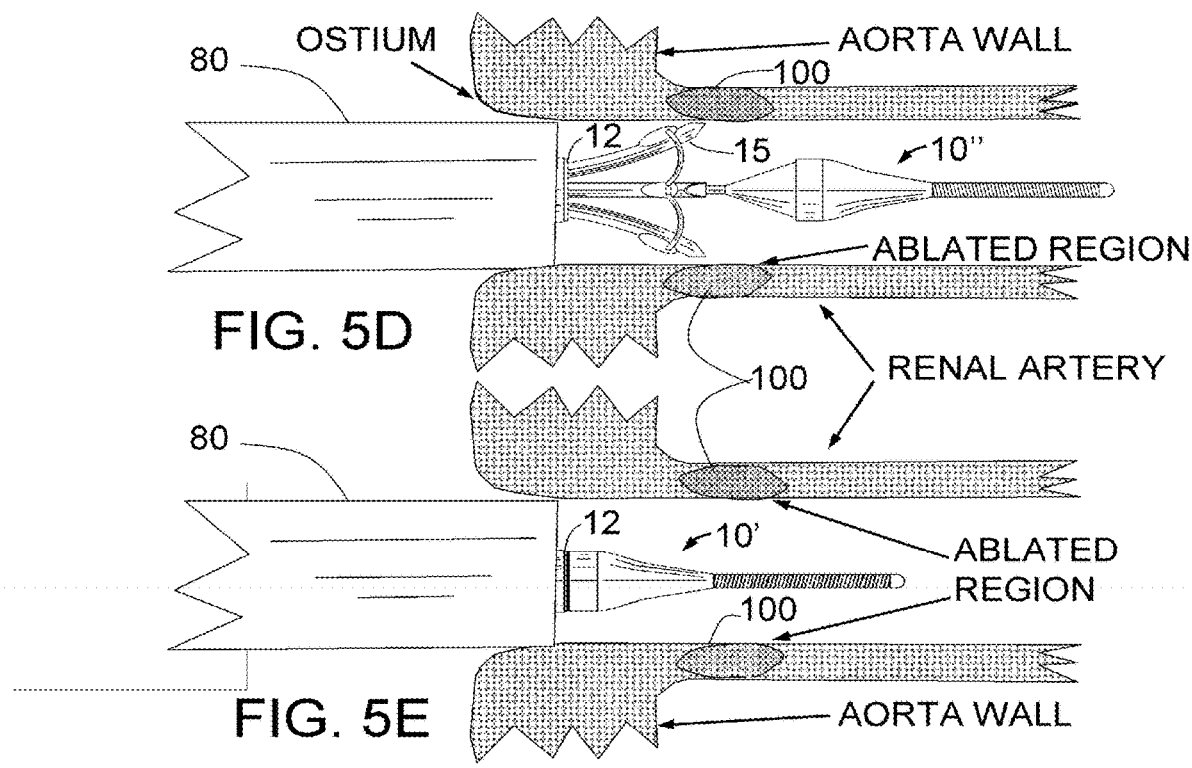

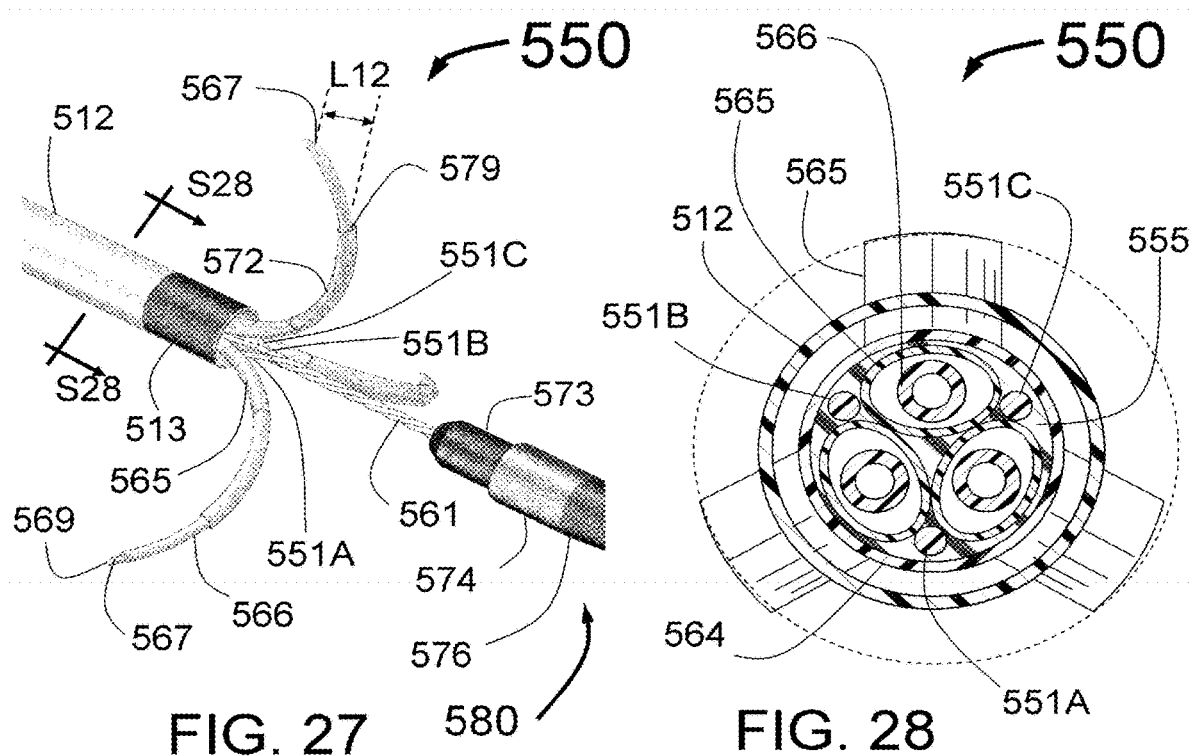

INTRAVASCULAR FLUID CATHETER WITH MINIMAL INTERNAL FLUID VOLUME

CROSS-REFERENCE TO RELATED APPLICATIONS

Any and all applications for which a foreign or domestic priority claim is identified in the Application Data Sheet as filed with the present application are hereby incorporated by reference under 37 C.F.R. § 1.57.

FIELD OF USE

This invention is in the field of devices to ablate muscle cells and nerve fibers for the treatment of cardiac arrhythmias, hypertension, congestive heart failure and other disorders.

BACKGROUND OF THE INVENTION

Since the 1930s it has been known that injury or ablation of the sympathetic nerves in or near the outer layers of the renal arteries can dramatically reduce high blood pressure. As far back as 1952, alcohol has been used in animal experiments. Specifically Robert M. Berne in "Hemodynamics and Sodium Excretion of Denervated Kidney in Anesthetized and Unanesthetized Dog" Am J Physiol, October 1952 171:(1) 148-158, describes painting alcohol on the outside of a dog's renal artery to produce denervation.

At the present time, physicians often treat patients with atrial fibrillation (AF) using radiofrequency (RF) catheter systems to ablate conducting tissue in the wall of the left atrium of the heart around the ostium of the pulmonary veins. Similar technology, using radiofrequency energy, has been successfully used inside the renal arteries to ablate sympathetic and other nerve fibers that run in the outer wall of the renal arteries, in order to treat high blood pressure. In both cases these are elaborate and expensive catheter systems that can cause thermal, cryoablative, or other methods to injure surrounding tissue. Many of these systems also require significant capital outlays for the reusable equipment that lies outside of the body, including RF generation systems and the fluid handling systems for cryoablative catheters.

Because of the similarities of anatomy, for the purposes of this disclosure, the term target wall will refer here to either wall of a pulmonary vein near its ostium for AF ablation applications or the wall of the renal artery, for hypertension or congestive heart failure (CHF) applications.

In the case of atrial fibrillation ablation, the ablation of tissue surrounding multiple pulmonary veins can be technically challenging and very time consuming. This is particularly so if one uses RE catheters that can only ablate one focus at a time. There is also a failure rate using these types of catheters for atrial fibrillation ablation. The failures of the current approaches are related to the challenges in creating reproducible circumferential ablation of tissue around the ostium (peri-ostial) of a pulmonary vein. There are also significant safety issues with current technologies related to very long fluoroscopy and procedure times that lead to high levels of radiation exposure to both the patient and the operator, and may increase stroke risk in atrial fibrillation ablation.

There are also potential risks using the current technologies for RE ablation to create sympathetic nerve denervation from inside the renal artery for the treatment of hypertension or congestive heart failure. The short-term complications and the long-term sequelae of applying RE energy from inside the renal artery to the wall of the artery are not well defined. This type of energy applied within the renal artery, and with transmural renal artery injury, may lead to late restenosis, thrombosis, renal artery spasm, embolization of debris into the renal parenchyma, or other problems inside the renal artery. There may also be uneven or incomplete sympathetic nerve ablation, particularly if there are anatomic anomalies, or atherosclerotic or fibrotic disease inside the renal artery, such that there is non-homogeneous delivery of RE energy. This could lead to treatment failures, or the need for additional and dangerous levels of RE energy to ablate the nerves that run along the adventitial plane of the renal artery.

The Ardian system for RE energy delivery also does not allow for efficient circumferential ablation of the renal sympathetic nerve fibers. If circumferential RE energy were applied in a ring segment from within the renal artery (energy applied at intimal surface to kill nerves in the outer adventitial layer) this could lead to even higher risks of renal artery stenosis from the circumferential and transmural thermal injury to the intima, media and adventitia. Finally, the "burning" or the inside of the renal artery using RF ablation can be extremely painful. Thus, there are numerous and substantial limitations of the current approach using RF-based renal sympathetic denervation. Similar limitations apply to Ultrasound or other energy delivery techniques.

The Bullfrog® micro infusion catheter described by Seward et al in U.S. Pat. Nos. 6,547,803 and 7,666,163 which uses an inflatable elastic balloon to expand a single needle against the wall of a blood vessel could be used for the injection of a chemical ablative solution such as alcohol hut it would require multiple applications as it does not describe or anticipate the circumferential delivery of an ablative substance around the entire circumference of the vessel. The most number of needles shown by Seward is two and the two needle version of the Bullfrog® would be hard to miniaturize to fit through a small guiding catheter to be used in a renal artery. If only one needle is used, controlled and accurate rotation of any device at the end of a catheter is difficult at best and could be risky if the subsequent injections are not evenly spaced. This device also does not allow for a precise, controlled, and adjustable depth of delivery of a neuroablative agent. This device also may have physical constraints regarding the length of the needle that can be used, thus limiting the ability to inject agents to an adequate depth, particularly in diseased renal arteries with thickened intima. Another limitation of the Bullfrog® is that inflation of a balloon within the renal artery can induce stenosis due to balloon injury of the intima and media of the artery, as well as causing endothelial cell denudation.

Jacobson and Davis in U.S. Pat. No. 6,302,870 describe a catheter for medication injection into the inside wall of a blood vessel. While Jacobson includes the concept of multiple needles expanding outward, each with a hilt to limit penetration of the needle into the wall of the vessel, his design depends on rotation of the tube having the needle at its distal end to allow it to get into an outward curving shape. The hilt design shown of a small disk attached a short distance proximal to the needle distal end has a fixed diameter which will increase the total diameter of the device by at least twice the diameter of the hilt so that if the hilt is large enough in diameter to stop penetration of the needle, it will significantly add to the diameter of the device. For either the renal denervation or atrial fibrillation application, the length of the needed catheter would make control of such rotation difficult. In addition, the hilts which limit penetration are a fixed distance from the distal end of the needles. There is no built in adjustment on penetration depth which may be important if one wishes to selectively target a specific layer in the blood vessel or if one needs to penetrate all the way through to the volume past the adventitia in vessels with different wall thicknesses. Jacobson also does not envision use of the injection catheter for denervation. Finally, in FIG. 3 of Jacobson, when he shows a sheath over expandable needles, there is no guide wire and the sheath has an open distal end which makes advancement through the vascular system more difficult. Also, the needles, if they were withdrawn completely inside of the sheath, could, because of the hilts, get stuck inside the sheath and be difficult to push out.

The prior art also does not envision use of anesthetic agents such as lydocaine which if injected first or in or together with an ablative solution can reduce or eliminate any pain associated with the denervation procedure.

As early as 1980, alcohol has been shown to be effective in providing renal denervation in animal models as published by Kline et al in "Functional re-innervation and development of supersensitivity to NE after renal denervation in rats", *American Physiological Society* 1980:0363-6110/80/0000-0000801.25, pp. R353-R358. While Kline states that "95% alcohol was applied to the vessels to destroy any remaining nerve fibers, using this technique for renal denervation we have found renal NE concentration to be over 90% depleted (i.e. <10 mg/g tissue) 4 days after the operation" Again in 1983, in the article "Effect of renal denervation on arterial pressure in rats with aortic nerve transaction" Hypertension, 1983, 5:468-475, Kline again publishes that a 95% alcohol solution applied during surgery is effective in ablating the nerves surrounding the renal artery in rats. While drug delivery catheters such as that by Jacobson, designed to inject fluids at multiple points into the wall of an artery, have existed since the 1990's and alcohol is effective as a therapeutic element for renal denervation, there is need for an intravascular injection system specifically designed for the PeriVascular circumferential ablation of sympathetic nerve fibers in the outer layers around the renal arteries with adjustable penetration depth to accommodate variability in renal artery wall thicknesses.

The prior art also does not envision use of anesthetic agents such as lidocaine which, if injected first or in or together with an ablative solution, can reduce or eliminate any pain associated with the denervation procedure.

McGuckin, in U.S. Pat. No. 7,087,040, describes a tumor tissue ablation catheter having three expandable tines for injection of fluid that exit a single needle. The tines expand outward to penetrate the tissue. The McGuckin device has an open distal end that does not provide protection from inadvertent needle sticks from the sharpened tines. In addition the McGuckin device depends on the shaped tines to be of sufficient strength that they can expand outward and penetrate a the tissue. To achieve such strength tines would not be small enough so as to have negligible blood loss when retracted back following fluid injection for a renal denervation application. There also is no workable penetration limiting mechanism that will reliably set the depth of penetration of the injection egress from the tines with respect to the inner wall of the vessel, nor is there a pre-set adjustment for such depth. For the application of treating liver tumors, the continually adjustable depth of tine penetration makes sense where multiple injections at several depths might be needed; however for renal denervation, being able to accurately dial in the depth is critical so as to not infuse the ablative fluid too shallow and kill the media of the renal artery or too deep and miss the nerves that are just outside or in the outer layer of the renal artery.

Finally Fischell et al in U.S. patent applications Ser. Nos. 13/092,363, 13/092,363 describe expandable intravascular catheters with expandable needle injectors. In Ser. No. 13/092,363 the Fischells disclose an intravascular catheter with a sheath that, unlike Jacobson, has a closed configuration that completely encloses the sharpened needles to protect health care workers from needle stick injuries and blood borne pathogens. The Fischell application Ser. Nos. 13/092,363, 13/092,363, however show only designs to operate into the wall of the left atrium around the ostium of a pulmonary vein or into the wall of the aorta around the ostium of a renal artery and not from inside a vessel.

SUMMARY OF THE INVENTION

The present invention, Intravascular Nerve Ablation System (INAS), is capable of applying an ablative fluid to produce circumferential damage in the nerve tissue that is in or near the wall of a blood vessel with a relatively short treatment time using a disposable catheter and requiring no additional capital equipment. The primary focus of use of INAS is in the treatment of cardiac arrhythmias, hypertension and congestive heart failure. Unlike the Bullfrog or RF ablation devices that work with one or, at most two, points of ablation, the present invention is designed to provide PeriVascular fluid injection allowing a more uniform circumferential injury to the nerves, while minimizing injury to the intima and medial layers of the vessel wall. The term circumferential delivery is defined here as at least three points of simultaneous injection of a suitable ablative solution within a vessel wall, or circumferential filling of the space outside of the adventitial layer (outer wall) of a blood vessel. Unlike the Jacobson device of U.S. Pat. No. 6,302,870, which does describe circumferential delivery, the present invention does not depend upon rotation of a tube to create outward movement nor does it have a fixed diameter hilt to limit penetration. In addition, while Jacobson shows a version of his device that pulls back within a sheath like tube, the tube has an open end and the Jacobson claims require an increase in diameter to accommodate the manifold that allows the fluid flowing in one lumen from the proximal end of the catheter to egress through multiple needles. The preferred embodiment of the present invention uses a manifold that fits within the lumen of the tube thus greatly decreasing the diameter of the catheter which enhances delivery of the catheter to the desired site within the human body.

Specifically, there is a definite need for such a catheter system that is capable of highly efficient, and reproducible PeriVascular ablation of the nerves surrounding the renal artery ostium, or distal to the ostium in the renal artery wall, in order to damage the sympathetic nerve fibers that track from the peri-ostial aortic wall into the renal arteries, and thus improve the control and treatment of hypertension, etc.

This type of system may also have major advantages over other current technologies by allowing highly efficient, and reproducible Peri Vascular circumferential ablation of the muscle fibers and conductive in the wall of the pulmonary veins near or at their ostium into the left atrium of the heart. Such ablation could interrupt atrial fibrillation (AF) and other cardiac arrhythmias. Other potential applications of this approach may evolve.

The present invention is a small (<2 mm diameter) catheter, which includes multiple expandable, injector tubes having sharpened injection needles their distal ends. The preferred embodiment also includes expandable guide tubes to guide passage of the coaxial injector tubes to facilitate penetration of the sharpened injection needles arranged circumferentially around the body of the INAS near its distal end. Ablative fluid can be injected through the distal ends of these needles each having injection egress at or near its distal end, There is a penetration limiting member as part of the INAS so that the needles will only penetrate into the tissue of the wall of the target blood vessel to a preset distance. These may be a preset distance proximal to the distal end of each needle similar to the hilts of the Jacobson et al patent or the penetration limiting member may be built into the proximal section of the INAS. Limiting penetration is important to reduce the likelihood of perforation of the vessel wall, optimize the depth of injection or to adjust the depth to be into the PeriVascular volume just outside of the blood vessel wall. In a preferred embodiment for PVRD (PeriVascular Renal Denervation), expandable guide tubes are first deployed against the inside wall of the renal artery and act as a guide for separate coaxially longitudinally moveable injector tubes with sharpened injection needles with injection egress port(s) near the distal end.

Ideally, the injection needles should be sufficiently small so that there will be no blood loss that following withdrawal after penetration completely through the wall of the renal artery. A major advantage of the present invention embodiments is that with such small (<25 gauge) needles, self expanding structures may be quite flimsy and not reliable to ensure accurate penetration of the vessel wall. The present invention solves this problem in 2 ways. The use of a cord or wire attached at a fixed distance proximal to the distal end of the needles, limits penetration and connects the expandable injection needles to each other will assist in creating uniform expansion of the injection needles to facilitate reliable penetration of the vessel wall. The preferred embodiment however is the use of expandable guide tubes which open up against the inside of the vessel and therefore guide each injection needle directly to the point of penetration of the vessel wall. The guide tubes can be made of a memory metal such as NITINOL or of a plastic material such as polyamide or urethane. The guide tubes should also be radiopaque or have a radiopaque marker at the tip, e.g. a tantalum, gold or platinum band. The ideal configuration of the guide tubes is a pre-shaped self-expanding plastic tube with a soft tip so as not to damage or accidentally penetrate into the wall of the vessel. The last 0.5 to 3 mm of this plastic tube could be formed in a filled plastic having a radiopaque material such as barium or tungsten. It is also envisioned, that a two layer plastic tube e.g. urethane on the outside and polyamide on the inside could provide an even better structure. The durometer of the plastic used could also vary with a soft material at the tip, a stiffer material in the part that bends and expands outward and a softer material again in the section proximal to the expandable section. This last section being softer will facilitate the delivery of the INAS around the nearly right angle bend through a guiding catheter into a renal artery.

To facilitate the guide tubes staying against the inside wall of the target vessel, it is envisioned that the distal portions of the injector tubes including the injection needle would be formed with approximately the same radius of curvature as the guide tubes, in reality, the radius of curvature of the guide tube will vary with the diameter of the vessel, being larger for smaller vessels that will constrain the tubes not allowing them to completely open up. Thus ideally, the radius of curvature of the distal portion of each injector tube including the injection needle should be the same as the distal portion of the guide tubes at their maximum diameter.

The term expandable will be used throughout this specification to describe the outward movement of a portion of the present invention with respect to the longitudinal axis of the INAS catheter. It includes the outward motion of the guide tubes, injector tubes and/or needles. This expansion can be from the self-expansion of a self-expanding structure that is released from a constraining structure or it can be expansion facilitated by distal or proximal motion of another mechanism within the INAS such as a wire that pushes or pulls the expandable structure out from the longitudinal axis. Another term that can be used to describe of this outward movement is the term deflectable. For example, a self-expanding structure deflects outward when released from its constraint and use of a wire moved distally or proximally to cause the outward movement of the delectable component would, be a manually deflectable structure. It is also envisioned that an inflatable balloon can be used to deflect or expand the deflectable or expandable structure outward from the longitudinal axis of the INAS.

A preferred embodiment of the present invention that will function in vessels of different inside diameters has both the guide tubes and injection needles at the distal end of the injector tubes having a curved shape. Ideally the expanded shape of the guide tubes will be set so that without constraint of the inside of a vessel, they will achieve an expanded diameter slightly larger than the biggest vessel envisioned for device use. The guide tube shape should also have the distal ends at 90 degrees plus or minus 30 degrees to the longitudinal axis of the INAS. For example, the INAS guide tubes could have an unconstrained diameter of 9 mm where the distal ends curve back 100 degrees, i.e. 10 degrees further back than perpendicular to the longitudinal axis of the INAS. Thus when constrained in arteries of 8 mm or less the angles at which the guide tubes engage the inside of the vessel will be less than 100 degrees. For example, in a 7 mm diameter vessel the distal tips of the guide tubes might be close to 90 degrees, in a 6 mm vessel 80 degrees, in a 5 mm vessel 70 degrees. Even in a 5 mm vessel, the system will still work because of the curved shape of the injection needles that will curve back toward the proximal end of the INAS and ensure proper penetration of the vessel wall. It is an important feature of the present invention that the injector tubes curve back in the proximal direction as they extend from the distal end of the guide tubes and penetrate through the vessel wall. It would be typical for the injection egress of each injection needle at the distal end of the injector tubes to have a deployed position that is proximal to the distal end of the guide tubes. For example, with the injection egress of the injection needles at 2.5 mm distance beyond the distal end of the guide tubes, the injection egress might be 1 to 2 mm proximal to the distal end of the guide tube.

Because precise depth penetration is preferred, the tubing used for any of the INAS proximal or distal sections should have limited stretchability so they do not enlongate during deployment through a guiding catheter into the renal artery. For example, stainless steel, L605 or NINTINOL could be the best material for the proximal sections of the INAS. Metal reinforced tubing with reduced elongation tendencies could be the best for the distal section of the INAS where more flexibility is needed to go around the nearly right angle bend in the guiding catheter from the aorta to the renal artery.

The penetration limiting function of the present invention INAS as described herein uses one of the following techniques that will greatly reduce the diameter of the device as compared with the Jacobson designs of U.S. Pat. No. 6,302,870 and thus also improve the ability to deliver it into a vessel of a human body such as the renal artery. These techniques include:

Use of a cord or wire attached to the multiple needles that can fold during insertion to limit the diameter of the distal section of the INAS, Use of one, two or more short NITINOL, wires attached in the longitudinal direction at their proximal ends to the sides of the needle. The wires being designed to have their distal ends not be attached and having a memory state that curves away from the needle so as to act as a penetration limiting member for the needle. Such wires would fold tight against the needles to reduce the diameter of the distal section of the INAS, Use of two bends in the needle the bend forming the penetration limiting member and the bend also being in the circumferential direction so as to not increase the diameter of the distal section of the INAS, and The preferred embodiment includes the use of guide tubes that curve outward through which the needles slide in the longitudinal direction. The limit for penetration in this design is integral into the proximal end of the INAS and does not require diametric volume in the distal section of the INAS. This last embodiment has the added advantage of allowing adjustment of the penetration depth. The adjustment could include markings that allow for precise depth adjustments.

Adjustment of the penetration depth by mechanisms in the proximal end of the INAS may be either physician controlled or only accessible during device production. In the first case, use of intravascular ultrasound or other imaging techniques could be used to identify the thickness of the renal artery at the desired site for PVRD. The clinician would then adjust the depth accordingly. It is also envisioned that the INAS could be preset in the factory using the depth adjustment which would not be accessible to the clinician and if multiple depths are needed, different product codes would be provided. For example, three depths might be available such as 2 mm, 2.5 mm and 3 mm. The other advantage of factory adjustable depth is to simplify calibration and quality production as the variation for each produced INAS may require a final in factory adjustment of needle depth so that precise depth of penetration is provided. It is also an advantage for regulatory filings that a preset depth or depths be used during trials and for approval to limit potential error in setting the wrong depth. Finally, it is envisioned that both an internal adjustment for factory production and calibration and an externally available adjustment with depth markings could be integrated in to the INAS.

The injector tubes with distal needles are in fluid communication with an injection lumen in the catheter body, which is in fluid communication with an injection port at the proximal end of the INAS. Such an injection port would typically include a standard connector such as a Luer connector used to connect to a source of ablative fluid.

This injection system also anticipates the use of very small gauge needles (smaller than 25 gauge) to penetrate the arterial wall, such that the needle penetration could be safe, even if targeted to a plane or volume of tissue that is at, or deep to (beyond) the adventitial layer of the aorta, a pulmonary vein or renal artery. It is also anticipated that the distal needle could be a cutting needle or a coring needle and with a cutting needle the injection egress ports could be small injection holes (pores) cut into the sides of the injector tubes or distal needle, proximal to the cutting needle tip.

The expandable injector tubes may be self-expanding made of a springy material, a memory metal such as NITINOL or they may be made of a metal or plastic and expandable by other mechanical means. For example, the expandable legs with distal injection needles could be mounted to the outside of an expandable balloon whose diameter is controllable by the pressure used to inflate the balloon. There should be at least 2 injector tubes but 3 to 8 tubes may be more appropriate, depending on the diameter of the vessel to be treated. For example, in a 5 mm diameter renal artery, only 3 or 4 needles may be needed while in an 8 mm diameter renal one might need 6 needles.

The entire INAS is designed to include a fixed distal guide wire or be advanced over a guide wire in either an over-the-wire configuration where the guide wire lumen runs the entire length of the INAS or a rapid exchange configuration where the guide wire exits the catheter body at least 10 cm distal to the proximal end of the INAS and runs outside of the catheter shaft for its proximal section. The fixed wire version is preferred as it would have the smallest distal diameter.

The INAS would also include a tubular, thin-walled sheath that constrains the self-expanding injection tubes with distal needles and/or guiding tubes prior to deployment, and for removal from the body. The sheath also allows the distal end of the INAS to be inserted into the proximal end of a guiding catheter or introducer sheath. The sheath also serves to protect the operator(s) from possible needle sticks and exposure to blood borne pathogens at the end of the procedure when the INAS is removed from the patient's body.

It is also envisioned that the injection needles, guiding tubes and injection tubes could be formed from a radiopaque material such as tantalum or tungsten or coated, or marked with a radiopaque material such as gold or platinum so as to make them clearly visible using fluoroscopy.

It is also envisioned that one or more of the injector needles could be electrically connected to the proximal end of the INAS so as to also act as a diagnostic electrode(s) for evaluation of the electrical activity in the area of the vessel wall.

It is also envisioned that one could attach 2 or more of the expandable legs to an electrical or RF source to deliver electric current or RF energy around the circumference of a target vessel to the ostial wall to perform tissue and/or nerve ablation.

It is also envisioned that this device could utilize one, or more than one neuroablative substances to be injected simultaneously, or in a sequence of injections, in order to optimize permanent sympathetic nerve disruption in a segment of the renal artery (neurotmesis). The anticipated neurotoxic agents that could be utilized includes but is not limited to ethanol, phenol, glycerol, local anesthetics in relatively high concentration (e.g., lidocaine, or other agents such as bupivicaine, tetracaine, benzocaine, etc.), anti-arrhythmic drugs that have neurotoxicity, botulinum toxin, digoxin or other cardiac glycosides, guanethidine, heated fluids including heated saline, hypertonic salute, hypotonic fluids, KCl or heated neuroablative substances such as those listed above.

It is also envisioned that the ablative substance can be hypertonic fluids such as hypertonic saline (extra salt) or hypotonic fluids such as distilled water. These will cause permanent damage to the nerves and could be equally as good or even better than alcohol or specific neurotoxins. These can also be injected hot or cold or room temperature. The use of distilled water, hypotonic saline or hypertonic saline with an injection volume of less than 1 ml eliminates one step in the use of the INAS because small volumes of these fluids should not be harmful to the kidney and so the need to completely flush the ablative fluid from the INAS with normal saline to prevent any of the ablative fluid getting into the renal artery during catheter withdrawal is no longer needed. This means there would be only one fluid injection step per artery instead of two if a more toxic ablative fluid is used.

The present invention also envisions use of anesthetic agents such as lidocaine which if injected first or in or together with an ablative solution can reduce or eliminate any pain associated with the denervation procedure.

It is also envisioned that one could utilize imaging techniques such as multislice CT scan, MRI, intravascular ultrasound or optical coherence tomography imaging to get an exact measurement of the thickness and anatomy of the target vessel wall (e.g., renal artery) such that one could know and set the exact and correct penetration depth for the injection of the ablative agent prior to the advancement of the injector needles or injector tubes. The use of IVUS prior to use of the INAS may be particularly useful in order to target the exact depth intended for injection. This exact depth can then be targeted using the adjustable depth of penetration feature in our preferred embodiment(s). The selection of penetration depth can be accomplished using the proximal section/handle or by selection of an appropriate product code for the other designs that might have two to five versions each with a different penetration depth limit.

For use in the treatment of hypertension or CHF, via renal sympathetic nerve ablation, the present preferred guide tube embodiment of this invention INAS would be used with the following steps:

1. Sedate the patient in a manner similar to an alcohol septal ablation Versed and narcotic analgesic.
2. Engage a first renal artery with a guiding catheter placed through the femoral or radial artery using standard arterial access methods.
3. After flushing all lumens of the INAS including the injection lumen with saline, advance the distal end of the INAS with a fixed distal guidewire into the guiding catheter. Advance the device through the guiding catheter, until the distal end of the guiding tubes are at the desired location in the renal artery beyond the distal end of the guiding catheter.
4. Pull back the sheath allowing the expandable guide tubes to open up until the distal ends of the guide tubes press outward against the inside wall of the renal artery. This can be confirmed, by visualization of the radiopaque tips of the guide tubes.
5. Next, the radio-opaque injection tubes/needles are advanced coaxially through the guide tubes to penetrate through the internal elastic lamina (IEL) at a preset distance (typically between 0.5 to 4 mm but preferably about 2-3 mm) beyond the IEL into the vessel wall of the renal artery. Ideally, the very small gauge injection needles may be advanced to ~2-3 mm depth in the renal artery to deliver the neuroablative agent(s) at or deep to the adventitial plane, in order to minimize intimal and medial renal artery injury. The correct depth can be determined prior to the INAS treatment using CT scan, MRI, OCT or intravascular ultrasound to measure the renal artery wall thickness, such that the correct initial depth setting for the injector tube penetration is known prior to advancing the needles.
6. Inject an appropriate volume of the neuroablative fluid, such as ethanol (ethyl alcohol), distilled water, hypertonic saline, hypotonic saline, phenol, glycerol, lidocaine, bupivacaine, tetracaine, benzocaine, guanethidine, botulinum toxin or other appropriate neurotoxic fluid. This could include a combination of 2 or more neuroablative fluids or local anesthetic agents together or in sequence (local anesthetic first to diminish discomfort, followed by delivery of the ablative agent) and/or high temperature fluids (or steam), or extremely cold (cryoablative) fluid into the vessel wall and/or the volume just outside of the vessel. A typical injection would be 0.1-5 ml. This should produce a multiplicity of ablation zones (one for each injector tube/needles) that will intersect to form an ablative ring around the circumference of the target vessel. Contrast could be added to the injection either during a test injection before the neuroablative agent or during the therapeutic injection to allow x-ray visualization of the ablation zone.
7. Inject normal saline solution into the INAS sufficient to completely flush the ablative agent out of the injection lumen dead space) of the INAS. This prevents any of the ablative agent from accidentally getting into the renal artery during pull back of the needles into the INAS, Such accidental discharge into the renal artery could cause damage to the kidneys. This step may be avoided if distilled water, hypotonic or hypertonic saline is used as the ablative fluid.
8. Retract the INAS injector tubes/needles back inside the guide tubes. Then, retract and re-sheath the guide tubes by advancing the sheath over the guide tubes. This will collapse the guide tubes back under the sheath completely surrounding the sharpened needles. The entire INAS can then be pulled back into the guiding catheter.
9. In some cases, one may rotate the INAS 20-90 degrees, or relocate the INAS 0.2 to 5 cm distal or proximal to the first injection site and then repeat the injection if needed to make a second ring or an even more definitive ring of ablation.
10. The same methods as per prior steps can be repeated to ablate tissue in the contralateral renal artery.
11. Remove the INAS from the guiding catheter completely.
12. Remove all remaining apparatus from the body.
13. A similar approach can be used with the INAS, via transeptal access into the left atrium to treat AF, via ablation of tissue in the vessel wall of one or more pulmonary veins. When indicated, advance appropriate diagnostic electrophysiology catheters to confirm that the ablation (in the case of atrial fibrillation) has been successful It is also envisioned that one could mount injector tubes with needles on the outer surface of an expandable balloon on the INAS in order to deliver 2 or more needles into the vessel wall of a target vessel to inject ablative fluid.

Although the main embodiment of this invention utilizes three or more needle injection sites to circumferentially administer alcohol or other neuro-toxic fluid(s) to the wall or deep to the wall of the renal artery for sympathetic nerve ablation, it is also envisioned that other modifications of this concept could also be utilized to achieve the same result. In one case it is envisioned that circumferential fluid based (ethanol or other ablative fluid, a combination of ablative fluids, or heated fluid) could be administered in a circumferential fashion to a "ring segment" of the renal artery by injecting the ablative fluid into a space between two inflated balloons. Thus, after inflating a proximal occlusive balloon and a distal occlusive balloon, the ablative fluid would be injected into the space between the two balloons and allowed to dwell for a short period of time allowing the fluid, such as ethanol to penetrate through the arterial wall and reach the adventitial layer, thus disrupting and ablating the sympathetic nerves running in this space. After the dwell period the space could be flushed with saline and the balloons deflated.

Similarly, a single balloon with a smaller diameter near the middle of the balloon could function in the same way, as the ethanol or other ablative fluid, or a combination of ablative fluids, or heated fluid is injected in the "saddle-like" space in the central part of the balloon that is not touching the arterial wall.

It is also envisioned that another embodiment may include a circumferential band of polymer, hydrogel or other carrier, on the central portion of an inflatable balloon with the carrier containing the neurotoxic agent(s), such as alcohol, phenol, glycerol, lidocaine, bupivacaine, tetracaine, benzocaine, guanethidine, botulinum toxin, etc. The balloon would be inflated at relatively low pressure to oppose the intimal surface of the renal arterial wall, and inflated for a dwell time to allow penetration of the neurotoxic agent, circumferentially, into a "ring segment" of the renal artery and allow ablation of the sympathetic nerve fibers running near or in the adventitial plane.

It is also envisioned that the INAS catheter could be connected to a heated fluid, or steam, source to deliver high temperature fluids to ablate or injure the target tissue or nerves. The heated fluid could be normal saline, hypertonic fluid, hypotonic fluid alcohol, phenol, lidocaine, or some other combination of fluids. Steam injection, of saline, hypertonic saline, hypotonic saline, ethanol, or distilled water or other fluids via the needles could also be performed in order to achieve thermal ablation of target tissue or nerves at and around the needle injection sites.

It is also envisioned that the INAS could utilize very small diameter needle injection tubes (e.g., 25-35 gauge) with sharpened needles at their distal ends such that the needles would be advanced to, or even through the adventitial plane of the renal artery or aortic wall using a penetration limiting member(s) or the combination of the guide tubes with an adjustable depth advancement of injector tubes through the guide tubes in order to set the depth of penetration, and allow one to "bathe" the adventitial layer containing the sympathetic nerves with neurotoxic fluid, while causing minimal injury to the intimal and medial vessel wall layers. These very tiny needles could pass transmurally through the arterial wall yet create such tiny holes in the arterial wall that blood leakage from the lumen to outside the vessel as well as medial layer injury would be minimal, and thus safe. Thus, the present invention could have the injection be either into the wall of the renal artery, into the adventitia of the renal artery or deep to the adventitial layer (peri-adventitia) of the renal artery such that the injection needles or egress from injection tubes would occur via penetration all the way through the arterial wall to allow the ablative fluid to flow around and "bathe" the outside of the artery with one or more neuroablative substances.

Another embodiment may include two or more pores, or small metallic (very short) needle like projections on the outer surface of the central portion of an inflatable balloon, that would be in fluid communication with an injection lumen to allow injection into the wall of the renal artery and allow circumferential delivery of a neurotoxic agent(s). Given these teachings and embodiment descriptions, other similar techniques could be envisioned to allow other variations upon this concept of a balloon expandable, circumferential ablation system for renal artery sympathetic nerve ablation.

The preferred embodiment of the present invention, as described in the methods above, places the means to limit penetration of the vessel wall at the proximal end of the INAS. In this embodiment, at least three guide tubes with expandable distal portions run along the distal portion of the length of the INAS. A guide tube control mechanism with optional flushing port is attached to the proximal end of the INAS and controls the longitudinal motion of the guide tubes.

One injection tube is included for each guide tube where the injection tubes have sharpened (coring or cutting needle) distal ends with injection egress port(s) at or just proximal to the needle tip. The injection tubes are located coaxially inside of the guide tubes. The distal ends of the sharpened injection needles at the distal ends of the injection tubes are initially "parked" just proximal to the distal end of the guide tubes. A proximal injector tube control mechanism is attached to the proximal end of the injection tubes, or in the preferred embodiment to the proximal end of a single injector tube that connects to the multiple injector tubes through a connection manifold. The injector tube control mechanism when advanced will advance the injection needles out of the distal end of the guide tubes to the desired depth of penetration. One example of how the penetration is limited by the proximal section of the INAS is to have the injector tube control mechanism separated at its distal end from the proximal end of the guide tube control mechanism forming a needle advancement gap. The injector tube control mechanism could have means to adjust the needle advancement gap distance. Alternately, the adjustment could be on the guide tube control mechanism or a separate mechanism between the injector tube handle and guide tube handle. A fitting for injection of an ablative fluid is attached near the proximal end of the INAS and is in fluid communication with the injection lumens of the injector tubes.

In its initial configuration a sheath lies outside of the guide tubes constraining them. The proximal end of the sheath is attached to a sheath handle which can be locked down to prevent longitudinal motion with respect to the guide tubes or unlocked to allow the sheath to be moved in the proximal or distal direction to open and close the INAS.

The process to use the INAS proximal section is to have each of the lumens in the INAS flushed with normal saline. The distal end of the INAS is then advanced through a guiding catheter into a vessel such as a renal artery. The sheath control handle is then pulled back holding the guide tube handle in position. This will allow the distal portion of the guide tubes to expand outwardly against the wall of a vessel such as a renal artery. Optionally, after the sheath is pulled back, the guide tubes can then be pushed slightly forward using the guide tube handle to ensure they are engaged firmly against the vessel wall. The injector tube handle is then advanced so as to push the distal ends of the injection tubes having sharpened injection needles out of the distal end of the guide tubes which are touching the inside of the vessel wall. The needles will penetrate into the media of the vessel wall. Depending on the advancement gap, the penetration of the needles into the vessel wall can be limited. This can permit selective injection through the injection egress ports of the needles into the media, adventitia, outside of the adventitia. (peri-adventitia) or any combination of these depending on the number and location of injection egress ports. After the needles are properly placed into or through the vessel wall, a source of ablative fluid such as ethanol is attached to the fitting in the injection tube handle and the fluid is injected through the lumens inside the injector tubes and out through the injection egress ports into the tissue.

After the injection is complete, the injection tube handle is pulled back to retract the needles into the distal portion of the guide tubes. The sheath control handle is then advanced to collapse the guide tubes and close the INAS. The sheath control handle is then locked down to prevent inadvertent opening of the INAS. The INAS is then pulled back onto the guiding catheter and the same procedure can be repeated for the other renal artery.

In a preferred embodiment proximal section of the INAS has one handle including the sheath control mechanism, the guide tube control mechanism and the injector tube control mechanism. This preferred embodiment has two movement sections. A first movement section attached to the sheath control mechanism that moves the sheath with respect to the nice tubes, a second movement section which moves the injector tubes with respect to the guide tubes. Each of these movement sections would ideally also have a locking mechanism to prevent movement. In addition, it is envisioned that there would be an interlock between the two movement sections so that it is impossible to advance the needles unless guide tubes are deployed and expanded outward and a second interlock that prevents the sheath from closing unless the needles have already been retracted proximally into the guide tubes. The lock/unlock mechanism can be either a button that is depressed to unlock and released to lock or a rotational ring that is twisted in one direction to lock and the other to unlock.

A preferred embodiment would use the push button mechanism as follows. Push the button on the first movement section that is attached to the sheath control mechanism. This will unlock it from movement with respect to the guide tube control mechanism. Pull this first movement section proximally while holding the remainder of the handle fixed. This will pull the sheath in the proximal direction with respect to the guide tubes, allowing the guide tubes to expand outwardly against the inside of the renal artery. Release the button locking the sheath control mechanism to the guide tube control mechanism in the sheath open position releasing the interlock that prevents the injector tube control mechanism from being advanced.

Press the button on the second movement section that is attached to the injector tube control mechanism unlocking the movement of the injector tube control mechanism with respect to the guide tube control mechanism. Advance the injector tube control mechanism pushing the injector tubes with sharpened needles out through the distal ends of the guide tubes and into the wall of the vessel. Release the button locking the injector tube control mechanism to the guide tube control mechanism. In this configuration an interlock will prevent the first movement section from being able to advance the sheath with respect to the guide tubes while the needles are deployed. After injection of the ablative substance and flushing of the INAS with saline, the two steps are reversed. The button on the second movement section is now depressed and the injector tubes and needles are retracted proximally into the guide tubes. Releasing the button locks the injector tubes control mechanism with respect to the guide tube control mechanism and releases the interlock that prevents the sheath from closing.

The button on the first movement section can now be depressed and the sheath control mechanism advanced distally with respect to the guide tube control mechanism closing the INAS with the guide tubes now retracted back under the sheath.

In another embodiment the second movement section is attached to the guide tube control mechanism and the injector tube control mechanism is a third movement section. Here the second movement section only unlocks the injector tube control mechanism from the guide tube control mechanism and the injector tube control mechanism is what is pushed distally to advance the injector tubes with sharpened injection needles.

While a button is described above, a ring that is rotated to lock and unlock the relative movement of the control mechanisms is also envisioned.

Radiopacity of specific portions of the catheter is critical for use of the INAS. Ideally, the fixed guide wire at the distal end of the INAS is radio-opaque. There will also be one or more radio-opaque markers at the distal end of the sheath, on the proximal portion of the distal tip (obturator) of the INAS that closes with the distal end of the sheath, on the end of each guide tube and the distal end or the entire length of each injection tube/needle. Metal rings of tungsten, tantalum, gold or platinum can be used or radiopaque plastics formed with fillings of dense materials such as barium or tungsten can be used. The injection needles can have the needle or needle tip plated w radiopaque metal or if a coring needle, a sharpened radiopaque plug in the distal end of the needle can be used. It is also envisioned that a radio-opaque wire can be placed inside the injection needle to enhance radiopacity. For example a platinum or gold wire of smaller diameter than the needle lumen could fixed inside each needle lumen.

Thus in deploying the INAS, the markers on the sheath and distal tip will separate showing the retraction of the sheath. The marked ends of the guide tubes will then clearly show them separate and touch the inside of the vessel. The injection tubes/needles, when advanced, will be visible as extending beyond the distal ends of the guide tubes and clearly deep to the lumen of the vessel which can be seen with contrast injections using the guiding catheter. It is envisioned that fluoroscopy performed at 90 degrees to the distal portion of the INAS could clearly show from center to outside the following markers:

The radiopaque ring marking the distal end of the sheath

Outside of that the radiopaque markers at the ends of the guide tubes

Outside of that the distal portion of the injection needles extending outward through the vessel wall beyond the distal tip of each guide tube.

Although it is envisioned that there could be a number from one to 8 injector tubes/needles inside of 8 guide tubes, it is likely that 2, 3 or 4 tubes is optimal for circumferential tissue ablation.

Another important feature of the present invention INAS is a design that reduces the internal volume of the INAS the "dead space" to minimize the amount of saline needed to flush the ablative fluid out of the catheter into the desired volume of tissue. It is anticipated that less than 1 ml of an ablative fluid such as ethanol will be needed to perform PVRD. The dead space should be fess than 1 ml, better yet less than 0.5 ml and ideally less than 0.2 ml. With certain design features it is conceived that the dead space can be reduced to less than 0.1 ml. Such features include using a small diameter <0.5 trim ID hypotube for the inner tube used for fluid injection for the INAS, including a volume occupying structure such as a wire placed into the full length of the hypotube/inner tube to reduce the volume of the hypotube and thus the INAS dead space and/or designing the proximal injection port and or injection manifold at the proximal end of the INAS to have low volume by having small <0.5 mm inside diameter and short <2 cm length, One technique envisioned to decrease the dead space inside of the injection lumens of the INAS is to have a wire inside one or more of the lumens to take up volume.

Although the guide tube embodiment will work well to allow small diameter needles to be used that will minimize the potential for blood loss, other designs are also envisioned including:

Small diameter injector tubes/needles with a removable stylus that will provide enhanced radiopacity and/or structural strength to allow the shaped tube/needle to properly curve outward and penetrate the vessel wall.

A small diameter needle inserted into the distal end of a larger diameter pre-shaped plastic or metal injector tube Thus it is an goal of the present invention INAS is to have a percutaneously delivered catheter that can be used to treat atrial fibrillation with one, or more injections of an ablative fluid into the vessel walls of the pulmonary veins near the ostium, or into the left atrial tissue surrounding one or more of the pulmonary veins.

Another goal of the present invention INAS is to have a percutaneously delivered catheter that can be used to treat hypertension with one, or more injections of an ablative fluid into or deep to, the vessel wall of the renal arteries, or into the wall of the aorta surrounding the ostium of the renal artery.

Another goal of the present invention INAS is to facilitate injection of an ablative fluid into or beyond the outer layers of the renal artery to reduce or prevent injury to the inner layers including the media of the renal artery.

Another goal of the present invention INAS is to have a design with limited dead space, less than 0.2 ml and ideally less than 0.1 ml.

Another goal of the present invention is to have a two injection step method for renal denervation where the catheter is filled with normal saline before insertion into the body, then after needle deployment a first injection of ablative fluid (for example ethanol) is done followed by a second step to flush all the ablative fluid out of the catheter using normal saline or a similar fluid that is non-toxic to the kidneys. The INAS is closed and the same two injection steps are used for the other renal artery.

Still another goal of the present invention is to utilize distilled water, hypertonic or hypotonic fluid as the ablative fluid of choice. This can reduce the injection of ablative fluid to one injection (one step) per renal artery and shorten the procedure.

Still another goal of the present invention INAS is to have a percutaneously delivered catheter that includes a multiplicity f circumferentially expandable injector tubes, each tube having a needle at its distal end with injection egress allowing the delivery of an ablative fluid into the wall of a target vessel or into the space beyond the vessel wall.

Still another goal of the invention is to have a flexible penetration limiting member or means attached just proximal to the distal end of each injector needle, or relatively blunt tipped guiding tubes to limit the depth of needle penetration into, or just through, the vessel wall.

Still another goal of the present invention is to have a sheath that in conjunction with a distal tip provide for open and closed positions of the INAS, The closed position has the sheath and distal tip touching so as to totally enclose the sharpened needles while the open position allows the needles to expand outward for injection of the ablative fluid into or deep to the vessel wall.

Yet another goal of the present invention is to use heated or cooled ablative fluid to be the source of the tissue ablation such as with heated or cooled normal saline or to enhance the efficacy of an already ablative fluid such as ethanol.

Yet another goal of the present invention INAS is to have one or more of the injector needles act as diagnostic electrodes for measurement of electrical activity within the wall of the target vessel.

Yet another goal of this invention is to use a multiplicity of coaxially guided injector tubes that move slidably within corresponding expandable guiding tubes, to allow the safe, controlled and adjustable depth of passage of injector tubes with sharpened needles at their distal ends into and/or through the wall of a target vessel, to allow controlled chemoablation of nerves in the adventitial or peri-adventitial layer of an artery while minimizing intimal and medial injury of said artery.

Yet another goal of the present invention is to provide injection of an anesthetic agent before or during injection of the ablative fluid so as to prevent or reduce any pain associated with the denervation procedure.

Yet another goal of the present invention is to include one or more of the following radiopaque markers to assist in positioning, opening, closing and using the INAS. These include the following:

A radiopaque ring marking the distal end of the sheath

Radiopaque markers at the ends of the guide tubes either metal bands or plastic with a radiopaque filler such as barium or tungsten Radiopaque markers on the distal portion of the injection needles Radiopaque wires inside the lumen of the injector tubes and/or injection needles Radiopaque markers or outer layer of a fixed guidewire These and other goals and advantages of this invention will become, obvious to a person of ordinary skill in this art upon reading of the detailed description of this invention including the associated drawings.

BRIEF DESCRIPTION OF THE DRAWINGS

FIG. 5B is a schematic view of the distal portion of the closed INAS as the sheath is being pulled hack to allow the expandable tubes open against the wall of the renal artery distal to the ostium.

FIG. 5C is a schematic view of the distal portion of the fully open INAS of FIG. 3 with needles fully embedded into the wall of the renal artery to allow the infusion of an ablative substance into the vessel wall.

FIG. 5D is a schematic view of the distal portion of the closed INAS as the distal portion of the INAS is being pulled back into the sheath to close the INAS either for subsequent use in the other renal artery or for removal from the body.

FIG. 5E is a schematic view of the distal portion of the closed INAS of FIG. 2 after it has been closed by retraction of the distal portion of the INAS into the sheath either for subsequent use in the other renal artery or for removal from the body.

FIG. 27 is a schematic view of the needle section of another embodiment of the present invention INAS having a core wire formed from three twisted wires and non circular cross section guide tubes.

FIG. 28 is the central portion of a transverse cross section at S28-S28 of the INAS of FIG. 27.

DETAILED DESCRIPTION OF THE DRAWINGS

Figure 1:
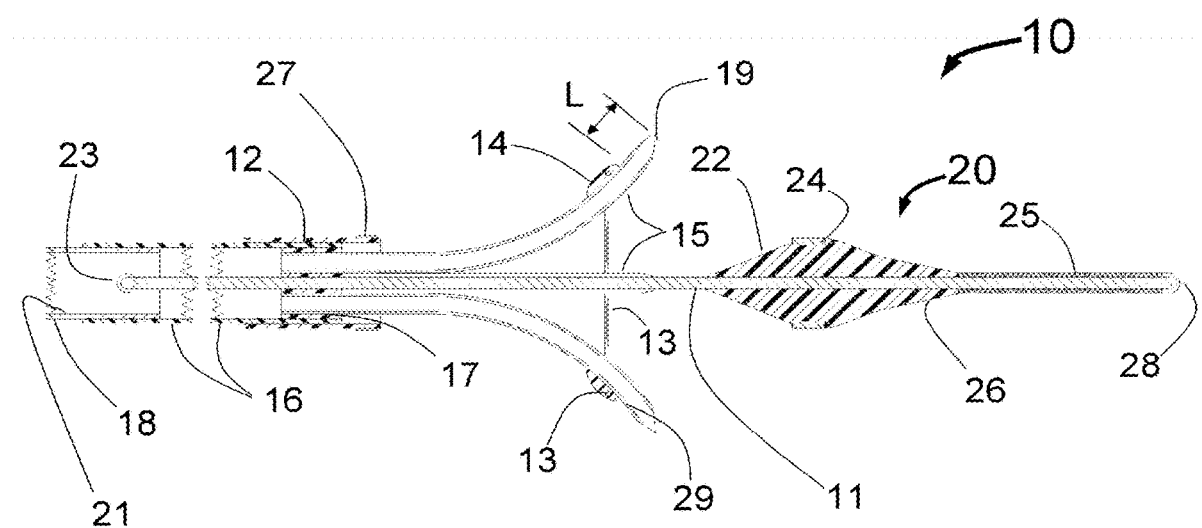
FIG. 1 is a longitudinal cross section drawing of the distal portion of the present invention Vascular Nerve Ablation System (INAS) having a fixed guide wire at its distal end.

FIG. 1 is a longitudinal cross section drawing of the distal portion of the present invention Vascular Nerve Ablation System (INAS) 10 having a fixed guide wire 25 with tip 28 at its distal end. FIG. 1 shows the INAS 10 in its fully open position with the self-expanding injector tubes 15 with distal ends sharpened to form injection needles 19 open to their maximum diameter. Flexible cords 13 with adhesive 14 that attaches the cords 13 to the injector tubes 15 act as a penetration limiting member to prevent the distal tip of the needles 19 from penetrating more than a maximum distance L into a vessel wall. The injector tubes can be made from any springy material with the preferred material being NITINOL. A separate spring or inflatable balloon could be placed inside of the injector tubes if the tubes are self-expanding to achieve the same objective. A balloon while increasing the diameter of the system would be able to push the needles with great force into the vessel wall.

A sheath 12 with radiopaque marker 27 is shown in FIG. 1 in its position where it has been pulled back to allow full expansion of the injector tubes 15. There are 4 injector tubes 15 in this embodiment of the INAS 10 although as few as 2 and as many as 12 are envisioned. The distance L can be between 0.2 and 2 mm with the optimal being about 1 mm.

The distal section 20 of the INAS 10 includes the distal wire 25, tapered flexible tip 26, radiopaque maker 24 and sheath engagement section 22 that assures that the distal portion of the INAS 10 will properly pull back into the sheath 12 following use of the INAS 10 to ablate tissue in a vessel of the human body. The INAS 10 is fully closed when the two radiopaque markers 27 and 24 are next to each other. This provides a visual indication during fluoroscopy.

The proximal end of the injector tubes 15 are held by a manifold 17 that is attached inside the distal end of the outer tube 16 and the core wire 11. The proximal end of the outer tube 16 is attached to a hypotube 18 that continues to the proximal end of the INAS 10. The hypotube 18 is typically made from a metal like 316 Stainless steel and the outer tube 16 is made from a plastic or metal reinforced plastic so that it is flexible enough to allow the INAS to easily be advanced and retracted around the bend in a typical guiding catheter such as that used for angioplasty or stenting of the renal arteries. The outer tube 16 would typically be between 5 and 30 cm long although it is also envisioned that the INAS 10 could be designed without a hypotube 18 and only a plastic or metal reinforced plastic outer tube 16 running to the proximal end.

The core wire 11 is attached to the inside of the hypotube 18 at junction point 23. This attachment could for example be by adhesive means, welding or brazing. Spot welding is the preferred method. In this way, the core wire 11 that supports the fixed wire 25 cannot be easily detached form the INAS 10. The injector lumen 21 inside of the hypotube 18 connects to the lumen of the outer tube 16 which is in fluid communication with the injector tube lumens 29 of each of the expandable tubes 15 allowing an ablative substance or solution to flow from the proximal end of the INAS 10 through the hypotube 18, through the outer tube 16, through the expandable injector tubes 15 and out of the sharpened injector needles 19 into a vessel wall.

Figure 2:
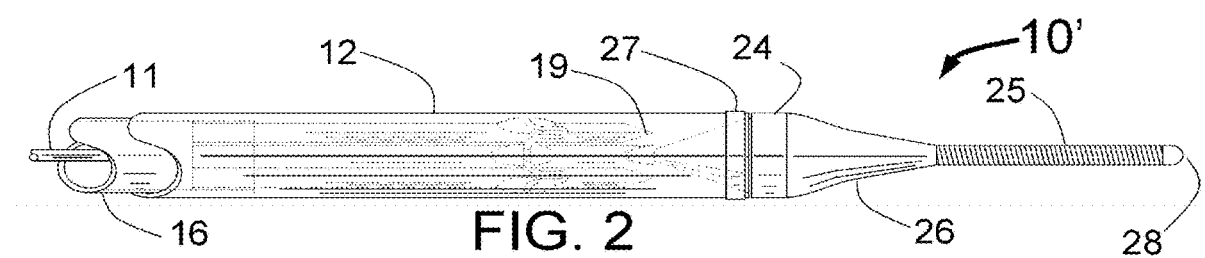
FIG. 2 is a schematic view of the distal portion NAS in its closed position as it would be configured for delivery into the human body or to cover the injector needles during removal from the human body.

FIG. 2 is a schematic view of the distal portion of the INAS 10' in its closed position as it would be configured for delivery into the human body or to cover the injection needles 19 during removal from the human body. The INAS 10' includes fixed wire 25 with tip 28, core wire 11, outer tube 16 and sheath 12. In this configuration the two radiopaque markers 27 and 24 are adjacent to each other with the sheath 12 being advanced to it fully distal position. Of great importance in this design is that in the closed position, the sharpened needles 19 are completely enclosed by the sheath 12 which is closed over the proximal portion of the tapered tip 26.

Figure 3:
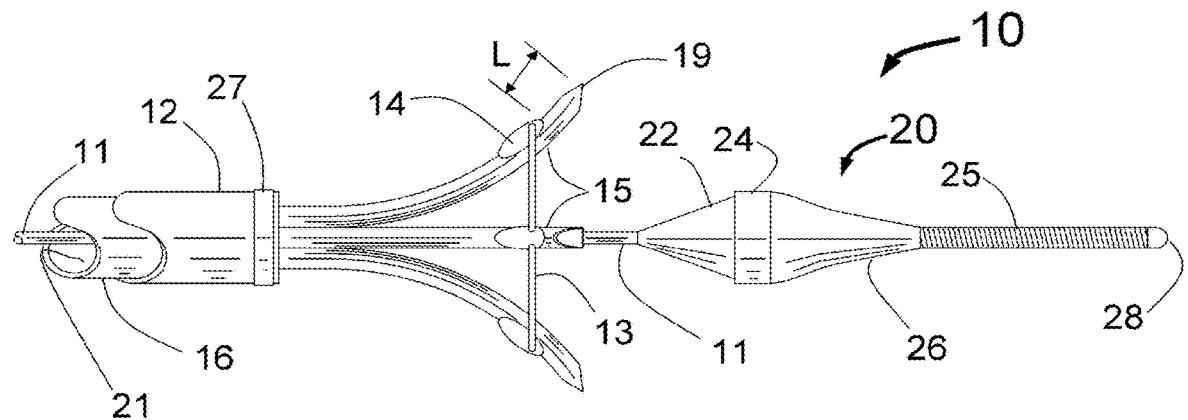
FIG. 3 is a schematic view of the distal portion of the INAS in its open position as it would be configured for delivery of an ablative solution into the target vessel wall.

FIG. 3 is a schematic view of the distal portion of the present invention Intravascular Nerve Ablation System (INAS) 10 in its fully open position having a fixed guide wire 25 with tip 28 at its distal end. FIG. 3 shows the INAS 10 in its fully open position with the self-expanding injector tubes 15 with distal ends sharpened to form injection needles 19 open to their maximum diameter. Flexible cords 13 with adhesive 14 that attaches the cords 13 to the injector tubes 15 act as a penetration limiting member to prevent the distal tip of the needles 19 from penetrating more than a maximum distance L shown in FIGS. 1 and 3 into a vessel wall.

A sheath 12 with radiopaque marker 27 is shown in FIG. 3 in its position where it has been pulled back to allow full expansion of the injector tubes 15. There are 4 injector tubes 15 in this embodiment of the INAS. The distal section 20 of the INAS 10 includes the fixed distal wire 25, tapered flexible tip 26, radiopaque maker 24 and sheath engagement section 22 that assures that the distal portion will properly pull back into the sheath 12 following use of the INAS 10 to ablate tissue in a vessel of the human body. Also shown in FIG. 3 are the outer tube 16 with injection lumen 21 and core wire 11.

Figure 4:
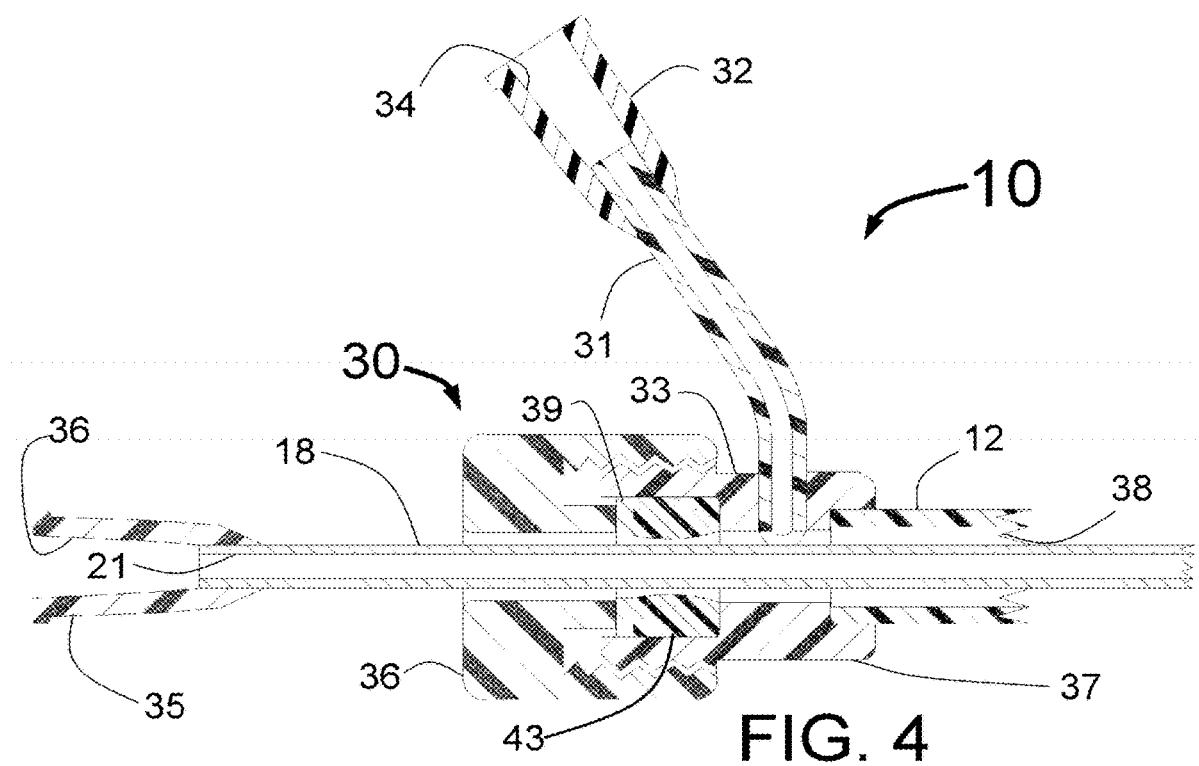
FIG. 4 is a longitudinal cross sectional drawing of the proximal end of the fixed wire embodiment of the INAS of FIGS. 1 through 3.

FIG. 4 is a longitudinal cross sectional drawing of the proximal end of the fixed wire embodiment of the INAS 10 of FIGS. 1 through 3. The hypotube 18 with injection lumen 21 also shown in FIG. 1, has a Luer fitting 35 with lumen 36 attached to its proximal end allowing a source of an ablative substance of solution to be injected through the lumen 36 of the Luer fitting 35 into the lumen 21 of the hypotube 18 and subsequently out of the injection needles 19 of FIGS. 1 through 3. The proximal end of the sheath 12 is attached to the distal end of the Tuohy-Borst fitting 30 with handle, 36, inner hub 33 washer 39 and O-Ring 43. As the handle 36 is tightened by screwing it down over the inner hub 33, the O-Ring will compress sealing the Tuohy-Borst fitting 30 against the hypotube 18. A side tube 31 with Luer fitting 32 having a lumen 34 is designed to allow the lumen 38 between the inside of the sheath 12 and hypotube 18 to be flushed with saline before insertion of the INAS 10 into a human body. Before insertion into the body, the Tuohy-Borst fitting 30 is tightened onto the hypotube 18 with the sheath 12 in its most distal position and the INAS 10' closed as is shown in FIG. 2. When in the distal end of the INAS 10' is properly positioned in one of the renal arteries, the Tuohy-Borst fitting is loosened and the handle 36 is pulled in the proximal direction while the Luer fitting 35 his held in place. This will open the INAS 10 and allow the injector tubes 15 of FIG. 1 to expand outward in the vessel.

Figure 5A:
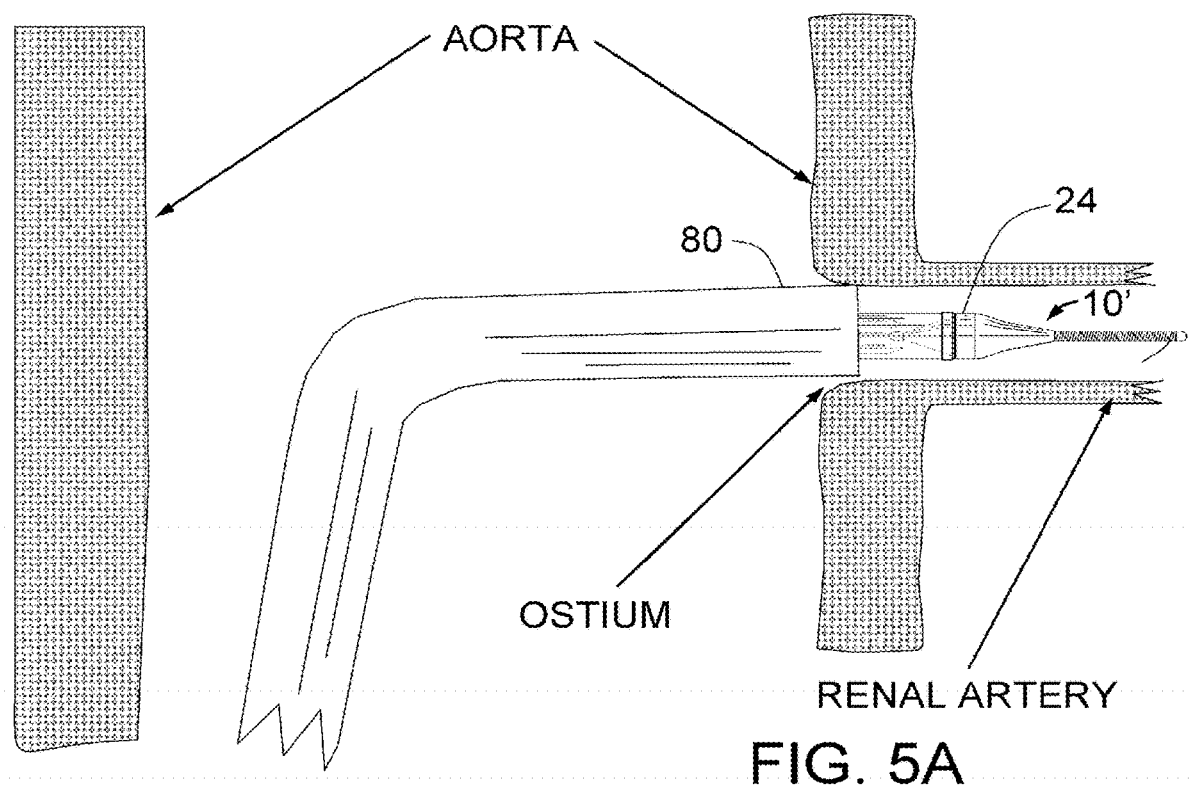
FIG. 5A is a schematic view of the distal portion of the closed INAS of FIG. 2 as it is first advanced out of a guiding catheter into a renal artery.

FIG. 5A is a schematic view of the distal portion of the closed INAS 10' of FIG. 2 as it is first advanced out of a guiding catheter 80 into a renal artery just distal to the ostium with the aorta. The INAS 10' is advanced until the marker band 24 distal to the distal end of the guiding catheter 80. It is anticipated that an optimal distance of 5 to 15 mm distal would work best although shorter and longer distances are possible depending on the geometry of the renal artery and the distance of penetration of the guiding catheter 80 into the ostium of the renal artery.

FIG. 5B is a schematic view of the distal portion of the closed INAS 10" as the sheath 12 is being pulled back to allow the expandable tubes 15 open against the wall of the renal artery just distal to the ostium into the aorta. In this position, it is desired that the angle A at which the distal end of the injection needles engage the inside of the vessel wall should be less than 80 degrees and ideally between 40 and 60 degrees. If the angle is too large, the injection tubes could buckle backwards instead of pushing the sharpened needles into the vessel wall. If the angle is too small, the needles might not penetrate properly and might slide distally along the inside of the vessel wall. After the sheath 12 is pulled back so it no longer constrains the expandable injector tubes 15, the INAS 10" is then pushed in the distal direction allowing the injector tubes 15 to continue their outward expansion as the injection needles 19 penetrate into the wall of the renal artery. The penetration will stop when the cords 13 engage the wall of the renal artery limiting the penetration of the needles 19. Alternatively, this "cord" may be replaced by a nitinol wire structure that is fixably attached to the injector tubes 15 to provide a (stiffer) metallic penetration limiting member.

FIG. 5C is a schematic view of the distal portion of the fully open INAS 10 of FIG. 3 with needles 19 fully embedded into the wall of the renal artery to allow the infusion of an ablative substance into the vessel wall. Although FIG. 5C show the cords 13 fully expanded, it would be typical for them to be slightly less in diameter than their maximum diameter when they engage the wall of the renal artery to limit the penetration of the needles 19. Preferably, the maximum diameter of the INAS 10 system selected for the procedure should be at least 2 to 4 mm greater than the inside diameter of the renal artery. For example, if the renal artery diameter at the desired ablation site is 5 mm in diameter, then a INAS 10 with maximum diameter of 7 to 9 mm should, be selected. In the configuration of FIG. 5C, the ablative substance is injected through the needles 19 into the wall of the renal artery. The preferred ablative substance is ethyl alcohol (ethanol), which has historically been used to ablate tissue, particularly nerve tissue in the cardiovascular system, Other agents such as phenol, glycerol, local anesthetic agent(s) such as lidocaine, guenethidine or other cytotoxic and/or neurotoxic agents are also anticipated as possible injectates.

FIG. 5D is a schematic view of the distal portion of the closed INAS 10" as its distal portion is being pulled back into the sheath 12 to close the INAS 10" either for subsequent use in the other renal artery or for removal from the body. A shaded area shows the ablated region 100 where the tissue in the wall of the renal artery has been ablated. If the needle depth of penetration is set at a greater depth (e.g. 2.5-3 mm) the ablation zone may be deeper (primarily adventitial) and create less injury to the intimal and medial layers of the renal artery wall than is shown in 5D.

FIG. 5E is a schematic view of the distal portion of the closed INAS 10' of FIG. 2 after it has been closed by retraction of the distal portion of the INAS into the sheath 12 either for subsequent use in the other renal artery or for removal from the body.

Figure 9:
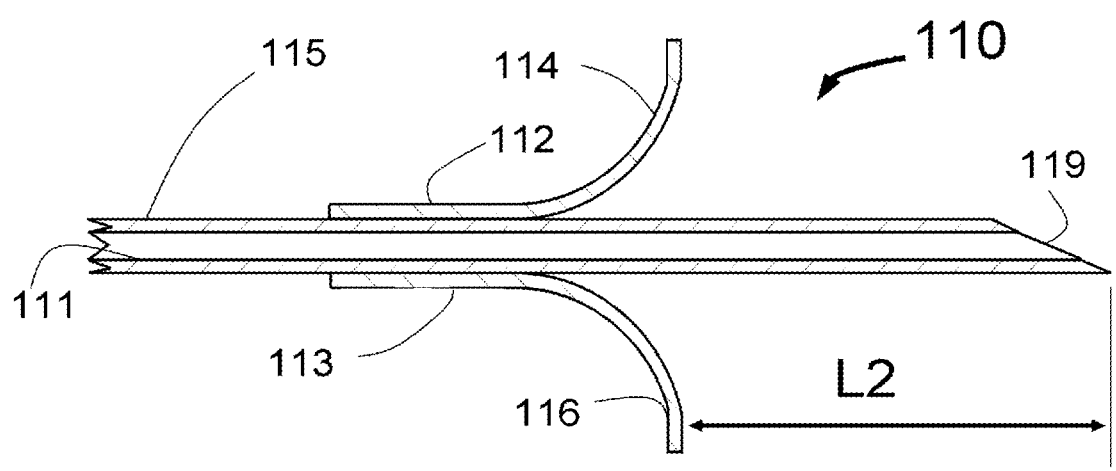
FIG. 9 is a longitudinal cross section drawing of the proximal section of an injection needle showing longitudinal welded wire penetration limiting members.

For this embodiment of the INAS 10, the method of use for hypertension would be the following steps:

1. Remove the sterilized INAS 10 from its packaging in a sterile field, flush the lumen 38 between the outer tube 12 and hypotube 18 with saline.
2. Advance the sheath 12 until the INAS 10' is in its close position.
3. Lock the Tuohy-Borst fitting 30 down onto the hypotube 18 of FIG. 4.
4. Access the aorta via a femoral artery, typically with the insertion of an introducer sheath.
5. Using a guiding catheter 80 of FIGS. 5A through 5E or a guiding sheath with a shaped distal end, engage the first targeted renal artery through the aorta. This can be confirmed with contrast injections as needed.
6. Place the distal end of the INAS 10 in its closed position of FIG. 2 into the proximal end of the guiding catheter 80. There is typically a Tuohy-Borst fitting attached to the distal end of a guiding catheter 80 to constrain blood loss.
7. The closed INAS 10 can be pushed through the opened Tuohy-Borst fitting into the guiding catheter 80.
8. Advance the INAS 10 through the guiding catheter, until the marker band 24 is distal to the distal end of the guiding catheter within the renal artery as shown in FIG. 5A,
9. Pull the sheath 12 back in the proximal direction while holding the Luer fitting 35 and hypotube 18 the proximal end of the INAS 10 fixed. This will allow expansion of the injector tubes 15 against the wall of the renal artery as shown in FIG. 5B.
10. Lock the Tuohy-Borst fitting 30 down on the hypotube 18.
11. With the Tuohy-Borst fitting at the proximal end of the guiding catheter 80 loosened advance the sheath 12 and hypotube 18 locked together pushing the sharpened needles 19 into, or through, the wall of the renal artery as the self-expanding injector tubes 15 continue to expand outward. The injector tubes 15 will stop penetration when penetration limiting member 13 engages the wall of the renal artery thus limiting the penetration of the needles 19 to the desired depth.
12. Attach a syringe or injection system to the Luer fitting 35 of FIG. 4 that provides ablative fluid that will be injected into the wall of the renal artery
13. Inject an appropriate volume of ethanol (ethyl alcohol) or other appropriate cytotoxic fluid, or combination of neuroablative fluids, or heated fluid or steam (e.g., 90-95 degree heated saline solution) from the syringe or injection system nigh the lumen 36 and out of the needles 19 into the wall of the renal artery. A typical injection would be 0.3-5 ml. This should produce a multiplicity of intersecting volumes of ablation (one for each needle) that should create a torroid of ablated tissue around the circumference of the renal artery as shown as the ablated regions shown in FIGS. 5D and 5E. Contrast and/or an anesthetic agent such as lidocaine can be injected before or at the same, time as the ablative fluid. Saline can be used to flush the neuroablative fluid out of the dead space prior to retraction of the injection tubes/needles.
14. Loosen the Tuohy-Borst fitting 30 and while holding the Tuohy-Borst fitting 30 and sheath 12 fixed, pull the Luer 35 with hypotube 18 in the proximal direction until the expandable tubes 15 with needles 19 are fully retracted back into the distal end of the sheath 12 and the marker bands 27 and 25 are next to one another. This is shown in FIGS. 5D and 5E.
15. In some cases, one may advance the INAS 10 again into the renal artery, rotate it between 20-90 degrees and then repeat the injection to make an even more definitive volume of ablation. This would be advantageous if the INAS 10 has fewer than 4 injector tubes and should not be needed with the 4 injector tubes shown in herein.
16. The same methods as per steps 8-15 can be repeated to ablate tissue around the other renal artery during the same procedure.
17. Remove the INAS 10 in its closed position from the guiding catheter. Being in the closed position, the needles 19 are enclosed and cannot harm the health care workers, or expose them to blood borne pathogens.
18. Remove all remaining apparatus from the body.

A similar approach can be used with the INAS 10, to treat atrial fibrillation through a guiding catheter inserted through the septum into the left atrium with the wall of the target vessel being the wall of one of the pulmonary veins.

Figure 6:
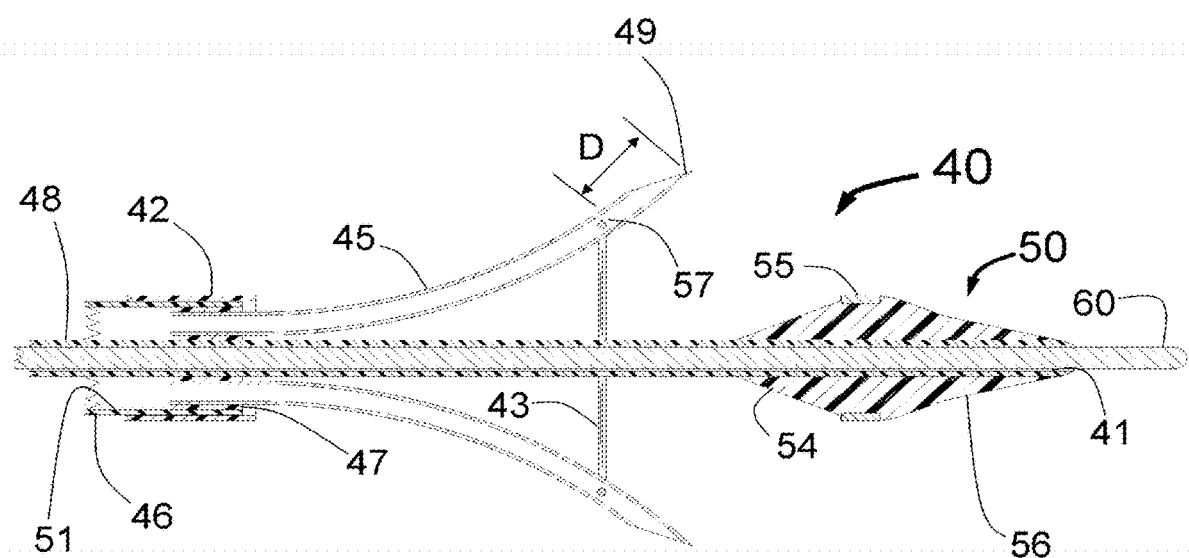
FIG. 6 is a longitudinal cross section drawing of the embodiment of the INAS that is delivered over a separate guide wire.

FIG. 6 is a longitudinal cross section drawing of the distal portion of another embodiment the present invention Vascular Nerve Ablation System (INAS) 40 that is delivered over a separate guide wire 60. FIG. 6 shows the INAS 40 in its fully open position with the self-expanding injector tubes 45 with distal ends sharpened to form needles 49 open to their maxi diameter. Flexible cords 43 connect the injector tube 45 and act as a penetration limiting member to prevent the distal tip of the needles 49 from penetrating more than a maximum distance D into a vessel wall. Unlike the cord 13 of FIG. 1, the cords 43 are fed though holes 57 in the sides of each injector tube 45 a distance D from the distal end. A drop of adhesive (not shown) can be used to seal the holes and prevent leakage of the ablative substance or solution during injection into a vessel wall.

A sheath 42 is shown in its position where it has been pulled back to allow full expansion of the injector tubes 45. There are 4 injector tubes 45 in this embodiment of the INAS 40 although as few as 2 and as many as 12 are envisioned. The distance D can be between 0.2 and 2 mm with the optimal being about 0.5-1 mm.

The proximal end of the injector tubes 45 are held by a manifold 47 that is attached inside the distal end of the outer tube 46 and the inner tube 48. An injection lumen 51 lies between the inner tube 48 and outer tube 46 proximal to the manifold 47. Ablative material injected through the injection lumen 51 will flow into the proximal ends of the injector tubes 45 and then out of the injection needles 49 into one or more layers of the blood vessel and/or into the volume of tissue just outside the vessel wall.

Figure 7:
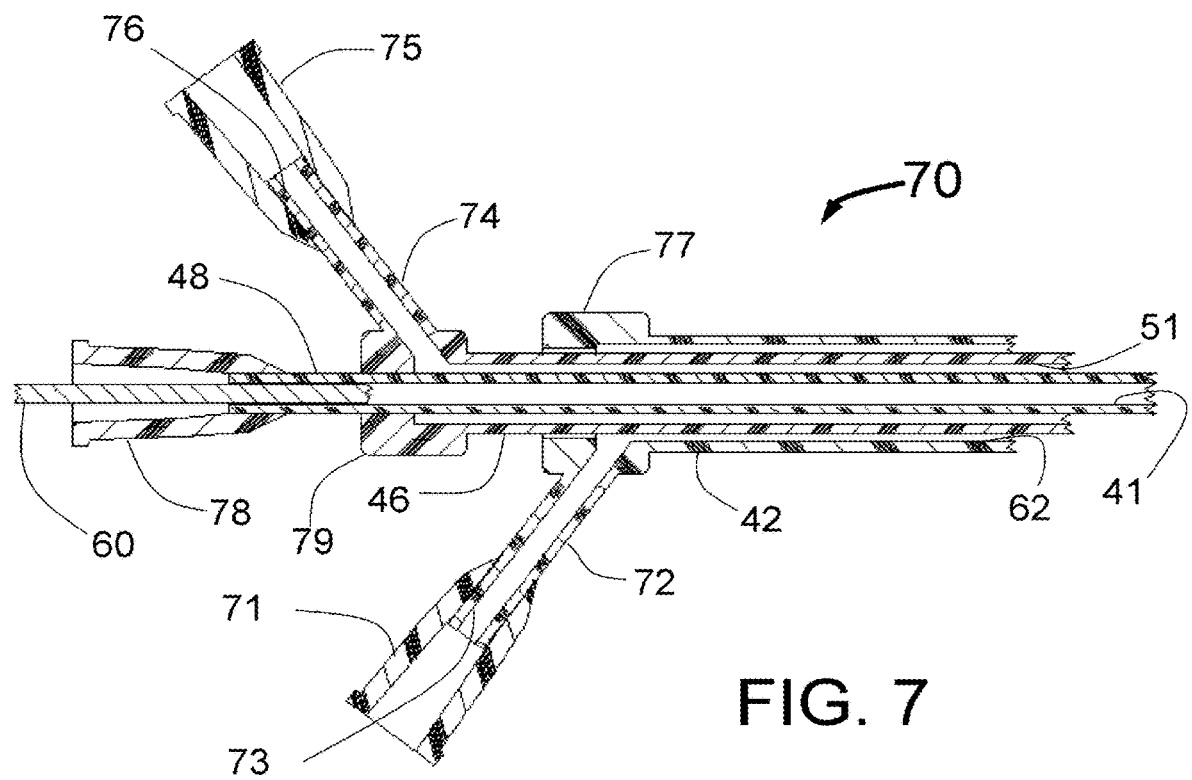
FIG. 7 is a longitudinal cross sectional drawing of the proximal end of an over-the-wire embodiment of the INAS of FIG. 6.

The distal section 50 of the INAS 40 that is coaxially attached to the distal section of the inner tube 48 includes the tapered flexible tip 56, radiopaque maker 55 and sheath engagement section 54 that assures that the distal portion of the INAS 40 will properly pull back into the sheath 42 following use of the INAS 40 to ablate tissue in a vessel of the human body. The guide wire 60 can be advance and retracted in the longitudinal direction inside of the guide wire lumen 41 that lies inside of the inner tube 48. The INAS 40 can be configured either as an over-the-wire or a rapid exchange device. If over-the-wire, the guide wire lumen 41 inside of the inner tube 48 runs all the way to the proximal end of the INAS 40 as is shown in FIG. 7. If a rapid exchange configuration is used then the guide wire would exit from the INAS 40 and run external to the outside of the INAS 40 for some portion of the length of the INAS 40. If a rapid exchange is used then a slot will be needed in the sheath 42 to allow for the sheath 42 to move longitudinally with respect to the rest of the INAS 40. The proximal end of the rapid exchange configuration would be identical to that of the fixed wire INAS 10 of FIG. 4. The guide wire would typically run outside of the body of the INAS 40 for at least the most proximal 10 cm with the preferred embodiment having the guide wire exit through the side of the outer tube 46 and sheath 42 between 5 and 15 cm from the distal end of the INAS 40.

Figure 8:
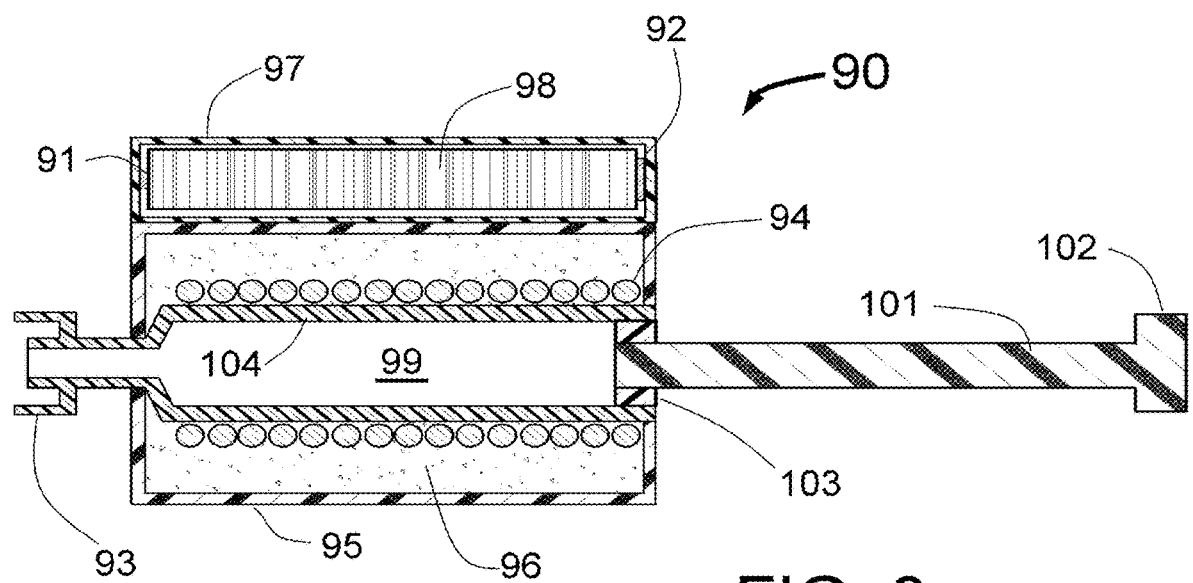
FIG. 8 is a longitudinal cross section drawing of an injector capable of delivering a heated ablative solution into the INAS of FIGS. 1-4.

FIG. 7 is a longitudinal cross sectional drawing of the proximal end 70 of an over-the-wire embodiment of the INAS 40 of FIG. 6. The inner tube 48 has a Luer fitting 78 attached to its proximal end. The guide wire 60 can be advanced through the guide wire lumen 41 inside of the inner tube 48. The proximal end of the outer tube 46 is attached to the hub 79 that is sealed against the inner tube 48, forming the injection lumen 51 between the inner tube 48 and outer tube 46. A side tube 74 with lumen 76 connects into the hub 79 with a Luer fitting 75 attached to the proximal end of the side tube 74, A syringe or other injection device can be attached to the Luer fitting 75 to inject an ablative substance or solution through the lumen 76 into the injection lumen 51 into the injector tube 45 of FIG. 6 and out of the ends of the injection needles 49 into a vessel wall. The proximal end of the sheath 42 connects to the hub 77 that acts as a handle to slide the sheath 42 coaxially over the outer tube 46 to open and close the INAS 40 of FIG. 6. A side tube 72 with lumen 73 connects into the hub 77. A Luer fitting 71 it attached to the proximal end of the side tube 72 to allow the lumen 62 between the sheath 42 and the outer tube 46 to be flushed with saline solution before introduction of the INAS 40 in to the human body. While the hub 77 shown here is a plastic member, it is envisioned that a Tuohy-Borst fitting such as the Tuohy-Borst fitting 30 of FIG. 4 could be used here and could be advantageous as it would allow one to lock the sheath 42 in position onto the outer tube 46 during insertion and removal from the body so that the distal end of the sheath 42 would remain in its most distal position protecting the injection needles 49 and protecting health care workers from exposure to needle stick injury, FIG. 8 is a longitudinal cross section of a disposable injector 90 for use in providing ablative fluid heated to a preset temperature for injection through the INAS 10 of FIGS. 1-5C to ablate tissue in a human body. The injector 90 includes a syringe 104 with fluid storage volume 99 and female Luer fitting 93 that would typically attach to a standard stopcock (not shown) the stopcock being connected to the male Luer fitting 35 at the proximal end of the INAS 10 of FIGS. 1-4. It is also envisioned that a stopcock could be provided with either the injector 90 or INAS 10 or integrated into either. The syringe 104 is surrounded by the heating coil 94 which is contained within the case 95 filled with heat insulation 96. The power for the heating coil 94 comes from the battery 98 with positive terminal 91 and negative terminal 92 housed in the battery case 97. A moveable plunger 101 with handle 102 and distal sealing gasket 103 is used to inject the heated ablative fluid in the volume 99 through the Luer fitting 93 into the INAS 10 injector lumen 21 of FIG. 4 where it will then flow out through the injector needles 19 of FIGS. 1 and 3 into the tissue as shown in FIG. 5C. The injector 90 may include closed loop electronics with either a display of the temperature or one or more LEDs that let the user know when the ablative fluid in the syringe 104 is at the desired temperature. The injector 90 could be manufactured for a single preset temperature or be adjustable to more than one temperature. While HG. 8 shows a manual injection plunger 101, it is also envisioned that a fluid pump or mechanical system to depress the plunger could be integrated into the injector 90. The use of heated fluid to abate tissue may be either effective by having a normally benign substance like normal saline heated to the point where the heat causes the tissue ablation or the heat may act to improve the ablative ability of a fluid such as alcohol that is normally ablative at room or body temperature.

FIG. 9 is a longitudinal cross section drawing of the proximal section of an injection needle 110 with lumen 111 and distal end 119, showing attached longitudinal memory metal wire penetration limiting members 114 and 116 with proximal portions 112 and 113 respectively. These proximal portions 112 and 113 are attached (glued, welded or brazed) to the outside 115 of the needle so that when the needles 110 are released from inside of the sheath 12 of FIGS. 1-4 the distal portion of the wires 114 and 116 will assume their memory state as shown in FIG. 9 forming a member that will limit penetration of the needle tip 119 to approximately a preset distance L. Since most arteries have a similar thickness, the distance L2 can be set to ensure the ablative fluid injected through the needle lumen 111 will emerge in the appropriate volume of tissue. Selection of the appropriate volume can be set by different values of L2 such that the injection can be set to be in the media of the artery, the adventitia of the artery or outside the adventitia of the artery. While FIG. 9 shows two wires 114 and 116, one wire would also function to limit penetration or 3 or more wires could also be used. Ideally the wires) be attached to the outside of the needle 115 on the sides circumferentially of the needle and not on the inside or outside where the wires 114 and 116 would increase the diameter of the closed INAS 10 of FIGS. 1-4 before the sheath 12 is pulled back to deploy the needles.

It s also envisioned, that an injector designed to deliver a super-cooled ablative fluid into the INAS of FIGS. 1-4 could also be appropriate for this application.

An important aspect of the present invention is the circumferential delivery of the ablative fluid with respect to the vessel wall. Such delivery from one or more injection egress points must attack the nerve tissue circumferentially and at the correct depth to ensure efficacy, and ideally to minimize injury to the healthy and normal cellular structures of the intimal and medial layers. The circumferential delivery can be handled as described above in three different ways.

1. Injection into the vessel wall at three or more points around, the circumference of the vessel,
2. Injection into the space outside of wall of the vessel— although this can be accomplished by a single needle/ egress point, this is best done with at least two egress points so that the needles can be kept small so as to allow the vessel wall to reseal as the needles are retracted.
3. Injection into the inside to fill an annular space and delivery the ablative fluid circumferentially to the inside surface of the vessel.

Figure 10:
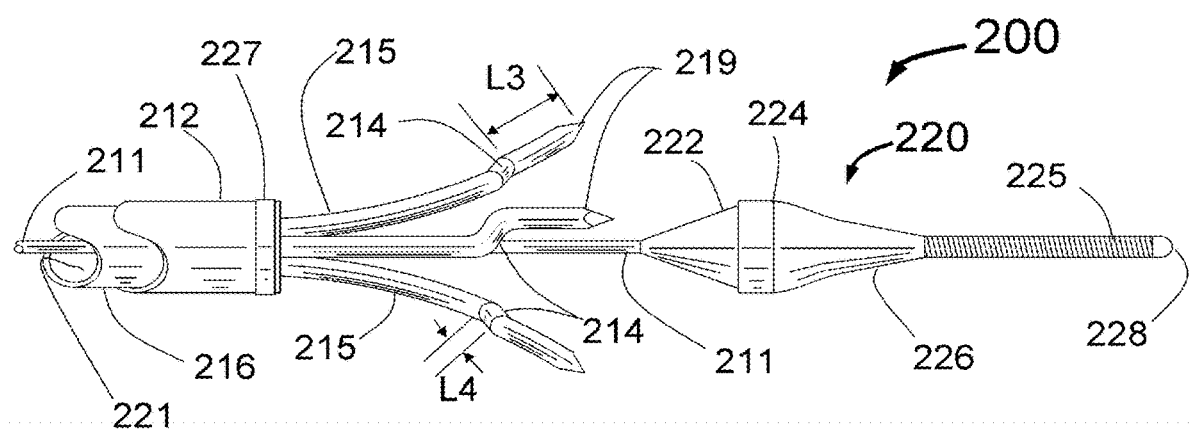
FIG. 10 is a longitudinal cross section drawing of the proximal section of another embodiment of the present invention that delivers an ablative fluid circumferentially to the inside of a target vessel.

FIG. 10 is a schematic view of yet another embodiment of the distal portion of the present invention Intravascular Nerve Ablation System (INAS) 200 in its fully open position having a fixed guide wire 225 with tip 228 at its distal end, FIG. 10 shows the INAS 200 in its fully open position with the self-expanding injector tubes 215 with distal ends sharpened to form injection needles 219 open to their maximum diameter. In this embodiment the injector tubes 215 each have a double bend or kink 214 having length L4 in the circumferential direction. The kinks 214 act as a penetration limiting member to prevent the distal tip of the needles 219 from penetrating more than a maximum distance L3 into a vessel wall.

A sheath 212 with radiopaque marker 227 is shown in FIG. 10 in its position where it has been pulled back to allow full expansion of the injector tubes 215. There are 3 injector tubes 215 in this embodiment of the INAS. The distal section 220 of the INAS 200 includes the fixed distal wire 225, tapered flexible tip 226, radiopaque maker 224 and sheath engagement section 222 that assures that the distal portion will properly pull back into the sheath 212 following use of the INAS 200 to ablate tissue in a vessel of the human body. Also shown in FIG. 10 are the outer tube 216 with injection lumen 221 and core wire 211. The INAS 200 of FIG. 10 would be used in the same way as the INAS 10 of FIGS. 1 through 5E with the difference being the use of the kinks (double bends) 214 as the penetration limiting members. The kinks 214 being integrated into the injector tubes 215 as compared with the penetration limiter of FIGS. 1-5E which are attached to the injector tubes. Adding the kinks 214 should be a matter of setting a double bend into the shape of the memory metal (e.g. NITINOL) tubing used to form each of the injector tubes 215 that have sharpened ends that form the injection needles 219. In this embodiment the injector tubes themselves limit the penetration into the wall of a target vessel. Processes for shaping and heat treating NITINOL tubing to set the memory are well known.

The present invention has discussed use of the INAS for ablating tissue in the human body. It may also have merit for intravascular injection of any fluid or medication. The ability to limit the depth of penetration allows it to inject any fluid selectively into the media, adventitia or outside of the adventitia of a blood vessel. It is also envisioned that the use of the double bend penetration limiting member concept of FIG. 10 could be applied to any application where fluid injection is required at a preset distance into human tissue.

The term circumferential delivery is defined here as at least three points of simultaneous injection spaced circumferentially within a vessel wall, or circumferential filling of the space outside of the adventitial layer (outer wall) of a blood vessel.

Figure 11:
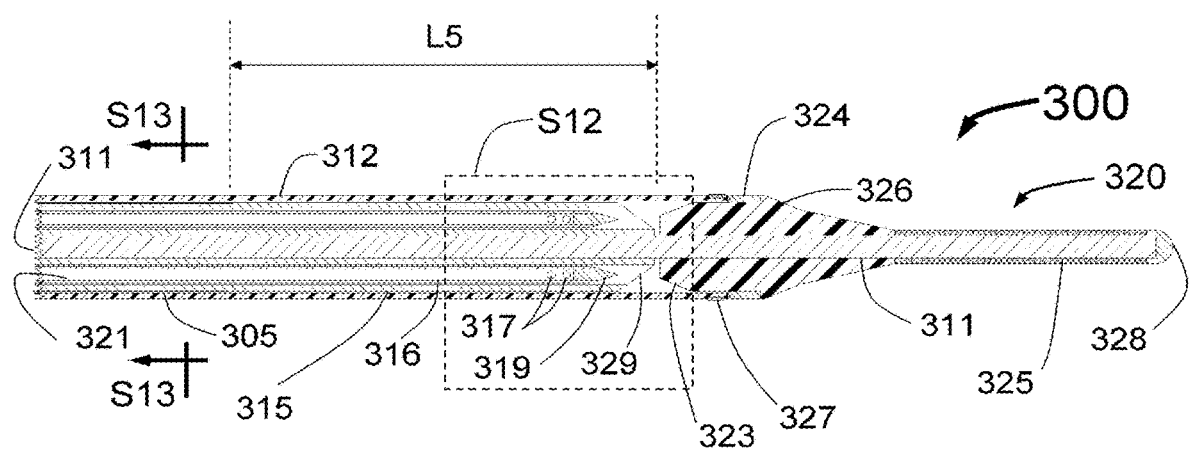
FIG. 11 is a longitudinal cross section of another embodiment of the present invention INAS in its closed position having four injector tubes that can slide within four guide tubes. The injector tubes have sharpened needles having injection egress ports at the distal end of each injector tubes.

FIG. 11 is a longitudinal cross section of the another embodiment of the present invention INAS 300 in its closed position having four injector tubes 316 that can slide within four guide tubes 315 having expandable distal portions. The injector tubes 316 with sharpened needles 319 have injection egress ports 317 near the distal end of each injector tube 316. A sheath 312 with distal radiopaque marker band 327 encloses the guide tubes 315 with coaxial injector tubes 316. The injector tubes 316 have injection lumens 321. The distal end of each of the guide tubes 329 are tapered to provide a surface that will be approximately parallel to the vessel wall when the guide tubes 315 expand outward during deployment. The distal portion of the guide tubes 315 having a length L5 are set in an expanded memory shape and as shown in FIG. 11 are constrained by the sheath 312 to prevent expansion. The four guide tubes 315 are not attached or connected to the core wire 311 over the distance L5. Proximal to the distance L5 the guide tubes 315 are attached or connected to the core wire 311 with the preferred embodiment shown in FIG. 13 where the core wire 311 and four guide tubes 315 are embedded in a plastic cylinder 305.

The INAS 300 distal end has a tapered section 326 attached to a distal shapeable fixed guide wire 320 with wire wrap exterior 325, core wire 311 and tip 328. The tapered section 326 includes a radiopaque marker 324 and proximal taper 323 to facilitate closing the sheath 312 over the proximal section 323 following deployment of the INAS 300 to inject ablative fluid into a vessel wall.

Figure 12:
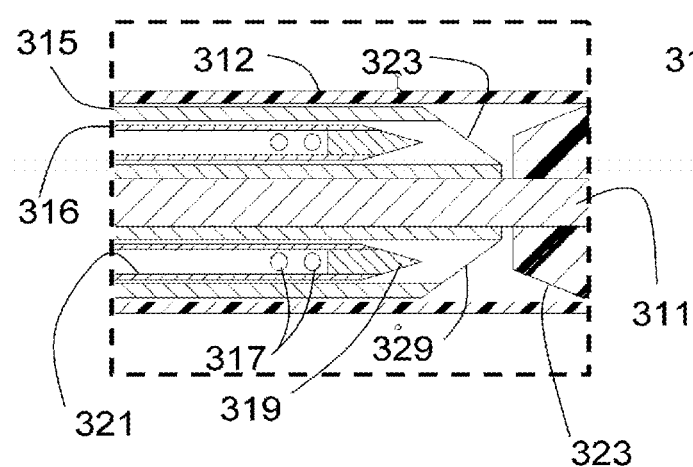
FIG. 12 is an enlargement of the area S12 of showing the distal portion of the injector tubes and guide tubes.

FIG. 12 is an enlargement of the area S12 of the INAS 300 of FIG. 11 showing guide tubes 315 located coaxially inside of the sheath 312. The distal portion of the injector tubes 316 having sharpened needles 319, lumens 321 and injection egress ports 327 are located coaxially inside of the distal portion of the guide tubes 315 with tapered distal ends 329. All or a portion of the needles 319 or the entire injector tube(s) may be made of a radiopaque material such as tantalum, platinum or gold. It is also envisioned that the ends of the needles may be coated or plated with a radiopaque material such as gold or that a platinum insert is placed into the distal tip of the injection tube prior to sharpening the tip into a cutting needle. Also shown are the core wire 311 and the proximal section 323 of the tapered section 326. It is also envisioned that a distal portion including the distal end 321 of the guide tubes 315 may also be made of, coated or plated with a radiopaque material such as gold.

Figure 13:
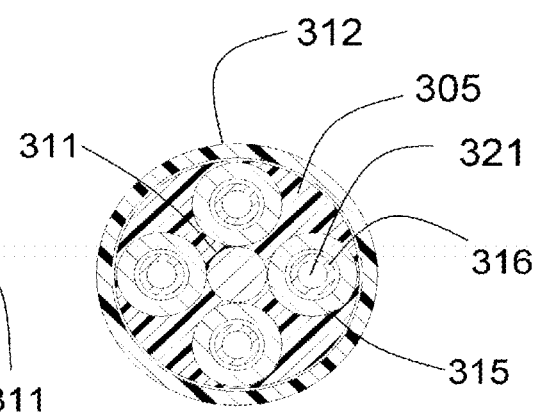
FIG. 13 is a circumferential cross section at S13-S13 of the INAS of FIG. 11.

FIG. 13 is a circumferential cross section at S13-S13 of the INAS 300 of FIG. 11 clearly showing the four guide tubes 315 attached to the outside of the core wire 31. The injector tubes 316 with injection lumens 321 are located coaxially inside of the guide tubes 315. The injection tubes 316 are free to slide in the longitudinal direction within the lumens of the guide tubes 315. The injection tubes 316 could also be formed from nitinol and pre-shaped to parallel the curved distal shape of the guide tubes 315 to enhance the coaxial movement of the injector tubes 316 within the guide tubes 315. The guide tubes 315, injection tubes 316 and core wire 311 lie coaxially within the sheath 312 which is free to slide over these parts. It is also shown how the guide tubes 315 and core wire 311 are be embedded in plastic 305 to better hold the parts together or they could be joined by welding, brazing of use of an adhesive. The use of the plastic 305 also allows a cylindrical surface to which the proximal portion of the sheath 312 can seal to allow flushing of the space between the inside of the sheath 312 and the outside of the plastic 305 with saline before the start of device use.

Figure 14:
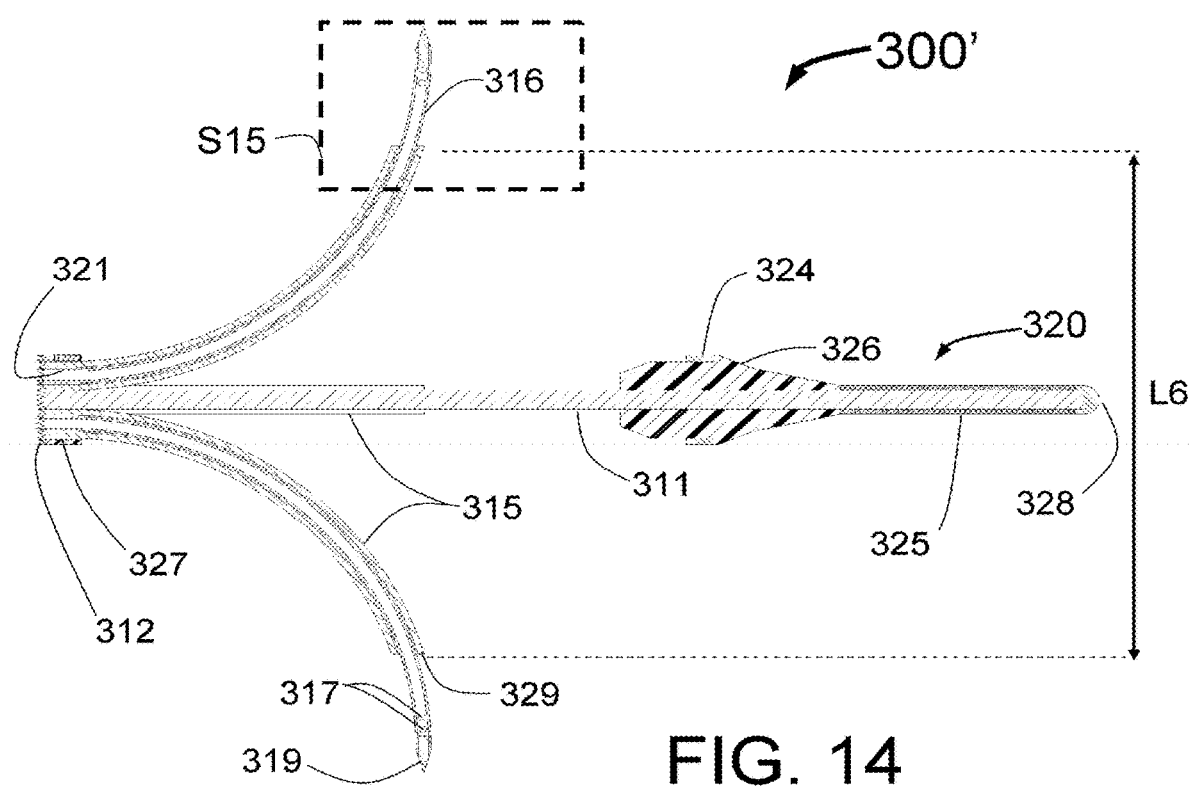
FIG. 14 is a longitudinal cross section of the expanded distal portion of the INAS.

FIG. 14 is a longitudinal cross section of the expanded distal portion of the INAS 300' in the fully open configuration with the injection tubes 316 shown advanced beyond the distal end of the guide tubes 315. The distal end of the injector tubes 316 has the sharpened needles 319 with injection egress ports 317.

In this configuration the sheath 312 has been pulled back to allow the guide tubes 315 to expand outward. The guide tubes 315 are typically made from a memory metal such as NITINOL, The injector tube 316 may be made from any metal such as 316 surgical grade stainless steel or may also be made from NITINOL or a radioopaque metal such as tantalum or platinum. If the elements 315 and 316 are not fabricated from a radio-opaque metal it is envisioned that distal portion of the injector tube(s) 316 and guide tube(s) 315 would be coated with a radio-opaque material such as gold, typically at or near the distal end of the tube(s) or a piece of radiopaque material may be used to form or be located near the sharpened needles 319 at the distal end of the injector tubes. The diameter L6 denotes the memory configuration for the fully open guide tubes 315. For use in the renal arteries, L6 would typically be between 3 and 10 mm with 8 mm being a best configuration if only one size is made as very few renal arteries are larger than 7 mm diameter. Also shown in FIG. 14 are the distal ends 329 of the guide tubes 315 that in the fully open configuration are parallel to the longitudinal axis of the INAS 300'. The distal portion of the INAS 300' has the tapered section 326 attached to the fixed guide wire 320 with tip 328, outer layer 325 and core wire 311.

Figure 15:
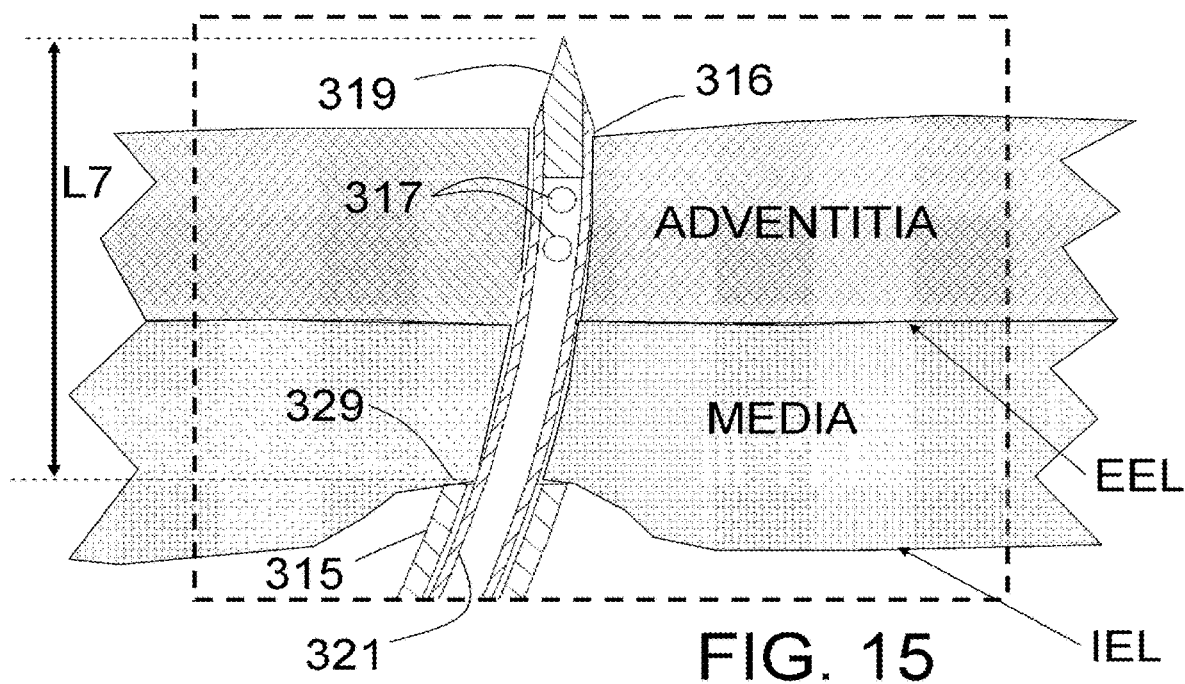
FIG. 15 is an enlargement of the area S15 of FIG. 14.

FIG. 15 is an enlargement of the area S15 of FIG. 14 as it would appear with the distal end of the injector tube 316 with lumen 321 and distal needle 319 fully advanced beyond the distal end 329 of the guide tube 315. Also shown in FIG. 15 is the arterial wall with internal elastic lamina (IEL), Media, External Elastic Lamina (EEL) and adventitia. FIG. 14 shows that the injection egress ports 317 are placed into the heart of the adventitia.

An important feature of the present invention INAS 300 is that the penetration depth for injection through the injection egress ports is adjustable so that any of the following can be accomplished.

1. Injection into the media
2. Injection into the media and adventitia by positioning one of the injection egress holes in each.
3. Injection into the adventitia as shown in FIG. 15,
4. Injection into both the adventitia and the volume outside of the adventitia and
5. Injection only into the volume outside the adventitia.

Specifically, the distance 12 that the tip of the needle 319 extends beyond the end 329 of the guide tube 315 can be adjusted using the apparatus in the proximal end of the INAS 300

Figure 16:
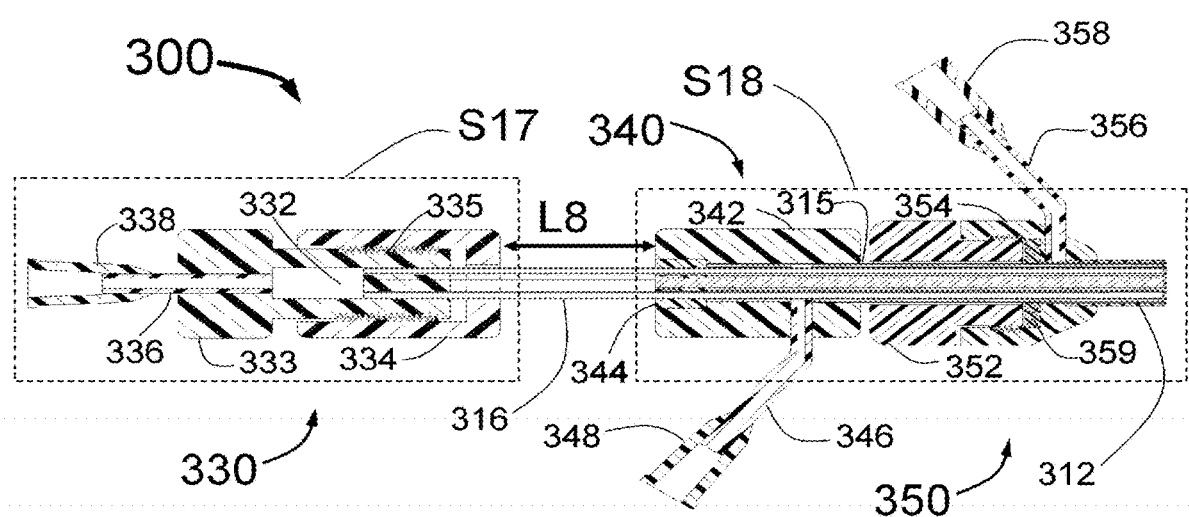
FIG. 16 is a longitudinal cross section of the proximal end of the INAS of FIGS. 11-15.

FIG. 16 is a longitudinal cross section of the proximal end of the INAS 300 of FIGS. 11-15. Three handles, the proximal injection handle 330, the central guide tube handle 340 and the distal sheath control handle 350 allow the relative longitudinal movement of the sheath 312, guide tubes 315 and injector tubes 316. The position shown for FIG. 16 has the sheath control handle 350 in its most proximal posit on which would indicate the sheath 312 has been hilly pulled back in the proximal direction which would allow the guide tubes 315 to expand outward as shown in FIG. 14. The gap with distance L8 between the injection handle 330 and the guide tube handle 340 can be adjusted using the screw adjustment piece 334 with screw threads 335 that allow it to move with respect to the proximal portion 333 of the injection handle 330. The gap L8 as set will limit the penetration of the needles 319 and injection egress ports 317 of the injector tubes 316 into the wall of the target vessel. Ideally, a scale can be marked on the proximal portion 333 of the proximal injection handle 330 so that the medical practitioner can set the gap L8 and thus adjust the penetration distance. A leur fitting 338 with access tube 336 is the port for ablative fluid injection into the handle central lumen 332 which is in fluid communication with the lumens 321 of the injector tubes 316.

The central guide tube handle 340 includes an outer portion 342, a sealing member 344 that seals the distal portion of the core wire 311 to the outer portion 342 and provides four holes through which the four injector tubes 316 can slide into the proximal ends of the guide tubes 315. A Luer fitting 348 with access tube 346 provides access to the space between the injector tubes 316 and the guide tubes 315 through holes in the guide tubes 347.

The distal sheath control handle 350 includes a distal portion 354 attached to the outside of the sheath 312 with Luer fitting 358 and side tube 356 providing access to the lumen under the sheath 312 to allow it to be flushed with saline before the procedure begins. The handle 350 also has proximal portion 352 and elastic washer 359 that is compressed by screwing the proximal portion 352 into the distal portion 354 to lock the position of the sheath 312 with respect to the guide tubes 315.

Figure 17:
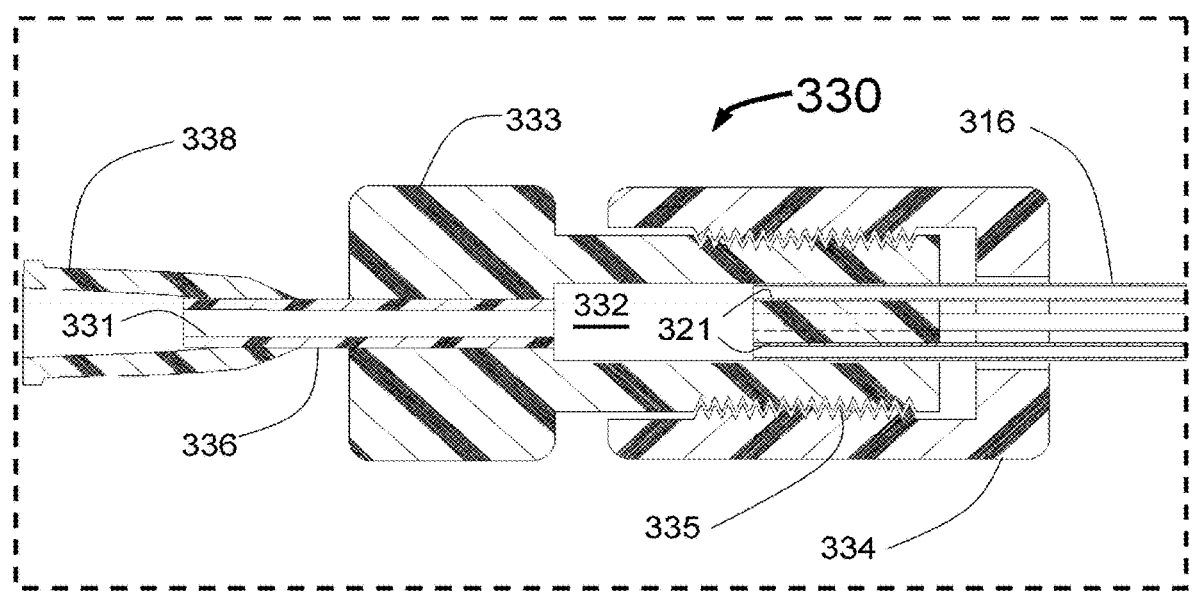
FIG. 17 is an enlargement pf the area S17 of FIG. 16.

FIG. 17 is an enlargement of the area S17 of FIG. 16 showing the injection handle 330 with proximal Luer fitting 338 attached to the side tube 336 with lumen 331, The proximal portion 333 is sealed against the outside of the side tube 336 and also seals against the outside of the four injector tubes 316. This sealing can be by an adhesive or by molding or forming the proximal piece onto the tubes 336 and 316. The lumen 331 of the side tube 336 is in fluid communication with the central lumen 332 of the proximal portion 333 which is in fluid communication with the lumens 321 of the injector tubes 316. Thus an ablative fluid injected through the Luer 338 will flow into the lumens 321 of the injector tubes 316 and will emerge through the injection egress ports 317 shown in FIG. 15 into the tissue in or near the wall of the target vessel. The screw threads 335 on both the proximal portion 333 and screw adjustment piece 334 of the injection handle 330 allow adjustment of the gap L8 of FIG. 16. The gap L8 as set will limit the penetration of the needles 319 and injection egress ports 317 of the injector tubes 316 into the wall of the target vessel. Ideally, a scale can be marked on the proximal portion 333 of the injection handle 330 so that the medical practitioner can set the gap L8 and thus adjust the penetration distance.

Figure 18:
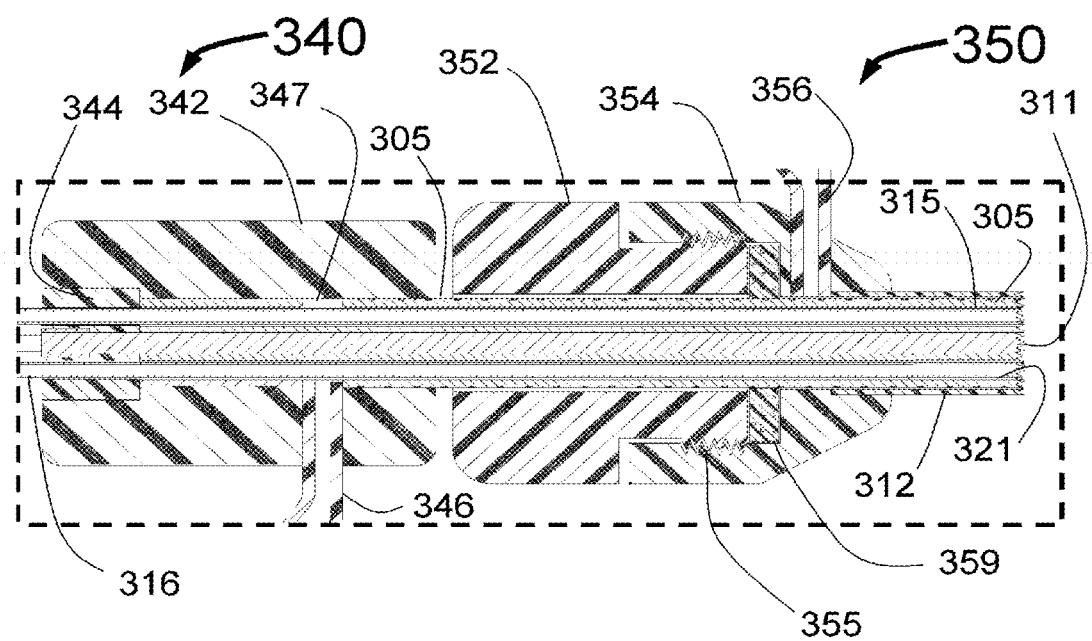
FIG. 18 is an enlargement of the area S18 of FIG. 16.

FIG. 18 is an enlargement of the area S18 of FIG. 16 showing the central guide tube handle 340 and the sheath control handle 350.

The central guide tube handle 340 includes an outer portion 342, a sealing member 344 that attaches the distal portion of the guide tubes 315 and core wire 311 to the outer portion 342. The outer portion 342 seals against the plastic 305 in which the guide tubes 315 and core wire 311 are embedded. Proximal to the proximal end of the plastic 305, a Luer fitting 348 (shown in FIG. 15) with access tube 346 provides access to the space between the injector tubes 316 and the guide tubes 315 through holes 347 in the guide tubes 315.

The distal sheath control handle 350 includes a distal portion 354 attached to the outside of the sheath 312 with Luer fitting 358 (shown in FIG. 15) and side tube 356 providing access to the lumen between the sheath 312 and the plastic 305 to allow it to be flushed with saline before the procedure begins. The handle 350 also has proximal portion 352 and elastic washer 359 that is compressed by screwing the proximal portion 352 into the distal portion 354 to lock the position of the sheath 312 onto the plastic 305. In this locked position with the INAS 300 closed as shown in FIG. 11 om INAS 300 is advanced into the body until the distal end with the marker band 324 of FIG. 11 is in the renal artery. The proximal portion 352 is then loosened so that the sheath control handle 350 can be pulled in the distal direction while holding the central guide tube handle 340 fixed. It is envisioned that when the proximal end of the sheath control handle proximal piece 352 touches the distal end of the outer portion 342 of the guide tube handle 340 as shown in FIG. 18, that the sheath 312 will be full retracted to allow expansion of the guide tubes 315 against the wall of the target vessel.

The full procedure for renal denervation using the INAS 300 is as follows:
1. Remove the sterilized INAS 300 from its packaging in a sterile field, flush the injection lumens 321 of the injector tubes and the space between the sheath 312 and plastic 305 and injector tubes 316 and guide tubes 315 with saline.
2. Access the aorta via a femoral artery, typically with the insertion of an introducer sheath,
3. Using a guiding catheter 80 of FIGS. 5A through 5E or a guiding sheath with a shaped distal end, engage the first targeted renal artery through the aorta. This can be confirmed with contrast injections as needed.
4. Place the distal end of the INAS 300 in its closed position of FIG. 11 into the proximal end of the guiding catheter. There is typically a Tuohy-Borst fitting attached to the distal end of a guiding catheter 80 to constrain blood loss.
5. The closed INAS 300 is then pushed through the opened Tuohy-Borst fitting into the guiding catheter.
6. Advance the INAS 300 through the guiding catheter, until the marker band 324 is distal to the distal end of the guiding catheter within the renal artery.
7. Pull the sheath 312 back in the proximal direction while holding the guide tube handle 340 fixed. This will allow expansion of the injector tubes 315 against the wall of the renal artery as shown in FIG. 15.
8. Lock the sheath control handle 350 down on the plastic 305.
9. Lock the Tuohy-Borst fitting at the proximal end of the guiding catheter down onto the sheath 312
10. Advance the guide tube handle 340 to be sure the distal ends 329 of the guide tubes 315 are in good contact with the wall of the renal artery and flaring outward in order to point more closely to perpendicular to the long axis of the renal artery wall.
11. While holding the guide tube handle 340 fixed, advance the injection handle 330 until its distal end touches the proximal end of the guide tube control handle 340. This will cause the needles 319 to advance through the distal ends 329 of the guide tubes 315 into the wall of the target vessel to the appropriate penetration limited by the two handles 330 and 340 touching.
12. Attach a syringe or injection system to the Luer fitting 338 that provides ablative fluid that will be injected into the wall of the renal artery. One could optionally inject an anesthetic drug like lidocaine and/or contrast media before the ablative fluid to prevent or reduce the pain associated with the procedure and/or ensure the needles are in the right position. It is also conceived that an anesthetic or contrast can be combined with the ablative fluid.
13. Inject an appropriate volume of the ablative fluid from the syringe or injection system through the lumens 321 of the injector tubes and out of the injection egress ports 317 into and/or outside of the wall of the renal artery. A typical injection would be 140 ml. This should produce a multiplicity of intersecting volumes of ablation (one for each needle) that should create a torroid of ablated tissue around the circumference of the renal artery as shown as the ablated regions shown in FIGS. 5D and 5E.
14. While holding the guide tube handle 340 fixed. Pull the injection handle 330 in the proximal direction retracting the needles 319 back into the guide tubes 315.
15. Unlock the sheath control handle 350 from the plastic 305 and while holding the guide tube control handle 340 fixed, advance the sheath control handle 350 in the distal direction until the guide tubes 315 are fully collapsed back into the distal end of the sheath 312 and the marker bands 327 and 324 are next to one another indicating that the INAS 300 is now in its closed position as shown in FIG. 11.
16. The same methods as per steps 6-15 can be repeated to ablate tissue around the other renal artery during the same procedure.
17. Remove the INAS 300 in its closed position from the guiding catheter, Being in the closed, position, the needles 319 are doubly enclosed within the guide tubes 315 which are inside the sheath 312 so the sharpened needles 319 cannot harm the health care workers, or expose them to blood borne pathogens.
18. Remove all remaining apparatus from the body.

A similar approach can be used with the INAS 300, to treat atrial fibrillation through a guiding catheter inserted through the septum into the left atrium with the wall of the target vessel being the wall of one of the pulmonary veins.

Figure 19:
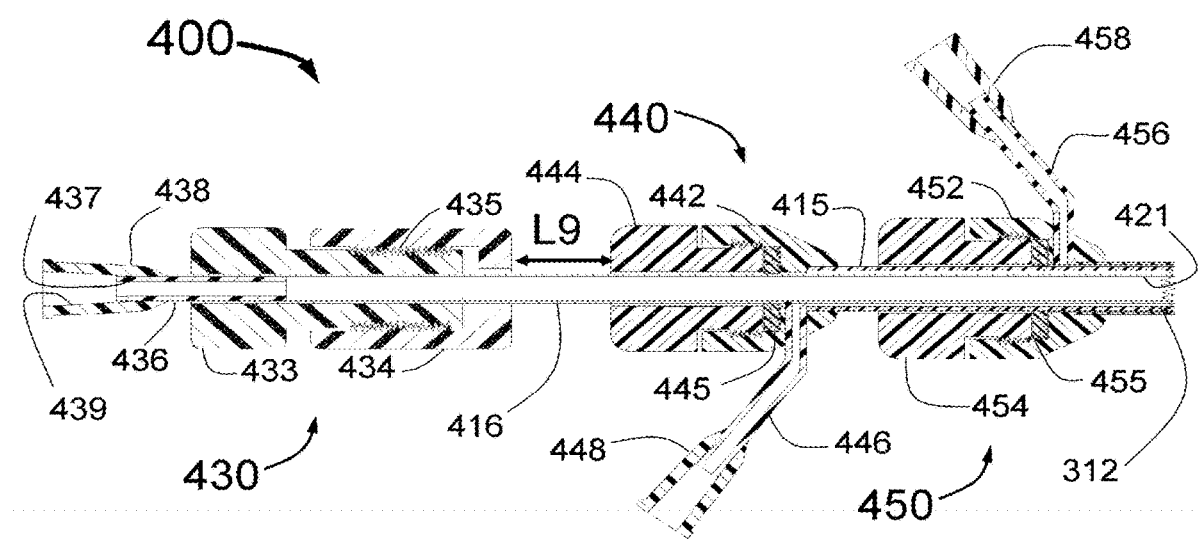
FIG. 19 is a longitudinal cross section of an alternate embodiment of all but the distal portion of the INAS using multiple guide tubes.

FIG. 19 is a longitudinal cross section of the proximal portion of an alternate embodiment of the INAS 400 which simplifies the design as compared to the INAS 300 proximal portion of FIG. 16. The INAS 400 uses the identical distal portion design as the INAS 300 of FIGS. 11-15, Three handles, the proximal injection handle 430, the central guide tube handle 440 and the distal sheath control handle 450 allow the relative longitudinal movement of the sheath 312, middle tube 415 and inner tube 416 with injection lumen 421. The position shown for FIG. 19 has the sheath control handle 450 near its most proximal position which would indicate the sheath 312 has been pulled back in the proximal direction. In this position, as with the INAS 300 of FIGS. 11-18 this will cause the distal portion of the guide tubes 315 to expand outward as shown in FIG. 14.

The gap with distance L9 between the injection handle 430 and the guide tube handle 440 can be adjusted using the screw adjustment piece 434 with screw threads 435 that allow it to move with respect to the proximal portion 433 of the proximal injection handle 430. The proximal end of the screw adjustment piece 434 is the penetration limiting member that will limit to the distance L9, the penetration of the needles 319 and injection egress ports 317 of the injector tubes 316 into the wall of the target vessel. Ideally, a scale can be marked on the proximal portion 433 of the handle 430 so that the medical practitioner can set the gap L9 and thus adjust the penetration distance. The central tube 416 with lumen 421 is sealed into the proximal piece 433 of the proximal injection handle 430. A luer fitting 438 with access tube 436 is the port for ablative fluid injection into the handle lumen 432. The lumen 439 of the Luer fitting 438 is in fluid communication with the lumen 437 of the access tube 436 which is in fluid communication with the injection lumen 421 of the inner tube 416. The inner tube 416 is typically a metal hypertube although a plastic tube or plastic tube with braided or helical wire reinforcement is also conceived. The central guide tube handle 440 attached to and controlling the longitudinal movement of the middle tube 415 includes a proximal portion 444 that can screw into a distal portion 442. When screwed in to the distal portion 442, the proximal portion 444 will compress the washer 445 allowing the handle 440 to be locked down onto the middle tube 415. This is also needed during preparation for use when the Luer fitting 448 with side tube 446 can be used to flush the space between the inner tube 416 and middle tube 415 with saline solution.

The distal sheath control handle 450 attached to and controlling the longitudinal movement of the sheath 312 includes a proximal portion 454 that can screw into a distal portion 452. When screwed in to the distal portion 452, the proximal portion 454 will compress the washer 455 allowing the handle 450 to be locked down onto the sheath 312. This is also needed during preparation for use when the Luer fitting 458 with side tube 456 can be used to flush the space between the middle tube 415 and sheath 312 with saline solution.

Figure 20:
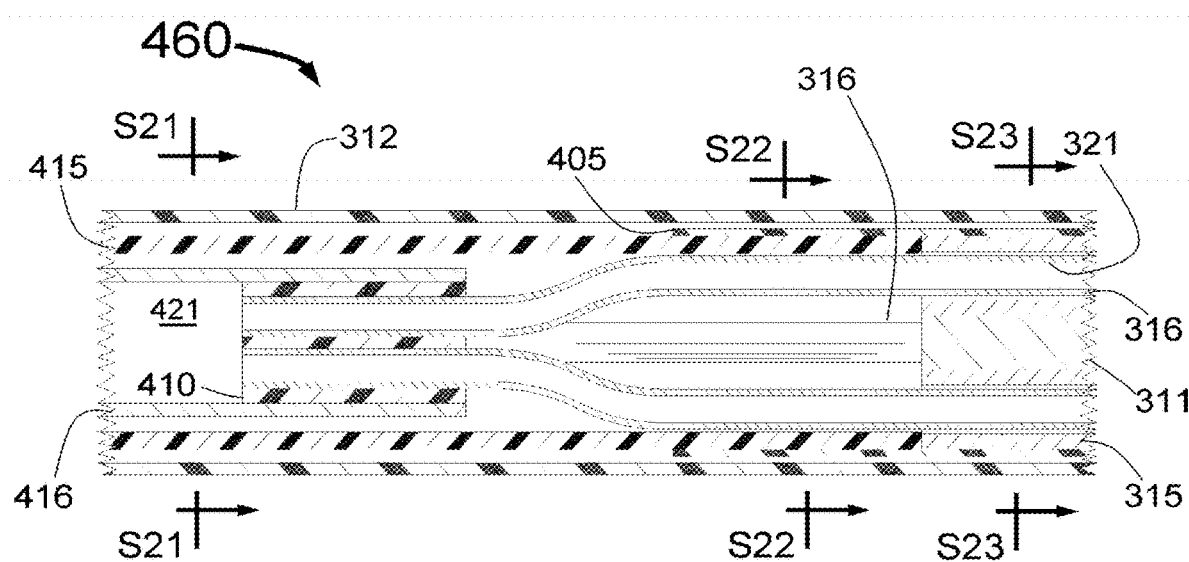
FIG. 20, is a longitudinal cross section of a central transition portion connecting the proximal portion of the of the INAS of FIG. 19 with the distal portion of the INAS of FIGS. 11-14.

FIG. 20 is a longitudinal cross section of a central transition portion 460 connecting the proximal portion of the INAS 400 of FIG. 19 with the distal portion of the INAS 300 of FIGS. 11-15. The proximal end of the central transition portion 460 includes the same three concentric tubes located at the distal end of the handle portion of the INAS 400 shown in FIG. 19. Specifically, the proximal end of the transition portion 460 includes the inner tube 416 with injection lumen 421, the middle tube 415 and the sheath 312. At the distal end of the inner tube 416, a manifold 410 is inserted which seals the inner tube 416 to the four injector tubes 316 such that the lumen 421 of the inner tube 416 is in fluid communication with the lumens 321 of the four injector tubes 316. In addition, longitudinal motion of the inner tube 416 will therefore be translated to longitudinal motion of the four injector tubes 316.

The middle tube 415 seals inside of the plastic member 405 which also seals to the guide tubes 315 and core wire 311. Longitudinal motion of the middle tube 415 will translate into longitudinal motion of the four guide tubes 315. The sheath 312 is the same sheath as in the distal portions of the INAS 300 of FIGS. 11-15.

Figure 21:
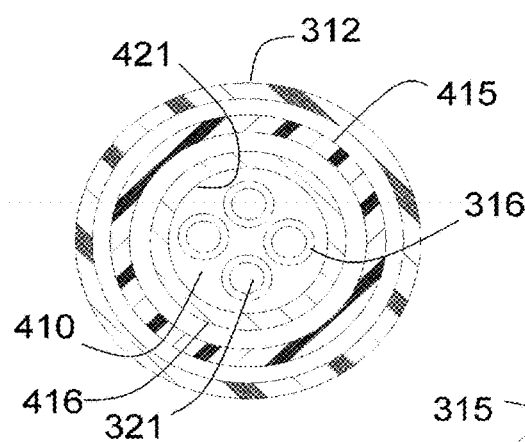
FIG. 21 is a circumferential cross section at S21-S21 of the INAS central transition portion of FIG. 20.

FIG. 21 is a circumferential cross section at S21-S21 of the central transition section 460 of FIG. 20. Looking in the distal direction, one sees in cross section, the three concentric tubes the sheath 312, middle tube 415 and inner tube 416. Inside the inner tube one sees the proximal end of the manifold 410 and the proximal ends of the four injector tubes 316. It can clearly be seen that the manifold 410 seals the four injector tubes 316 into the inner tube 416 and the lumens 321 of the injector tubes 316 open into the lumen 421 of the inner tube 416.

Figure 22:
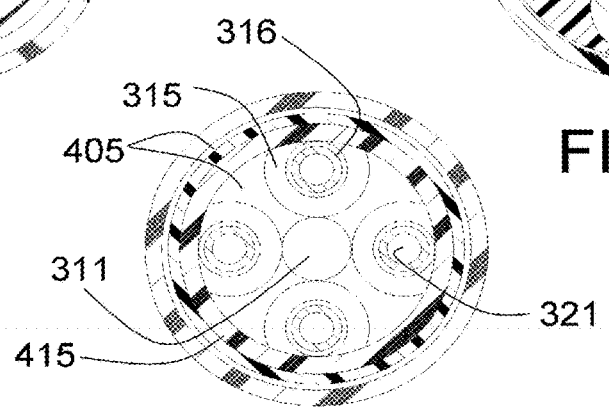
FIG. 22 is a circumferential cross section at S22-S22 of the INAS central transition portion of FIG. 20.

FIG. 22 is a circumferential cross section at S22-S22 of the central transition section 460 of FIG. 20. Looking in the distal direction one sees in cross section, the sheath 312 and middle tube 415. The middle tube 415 is sealed into the distal portion of the plastic member 405. One also sees the proximal end of the four guide tubes 315 and core wire 411. It also shows how the four injector tubes 316 enter the proximal ends of the guide tubes 315.

Figure 23:
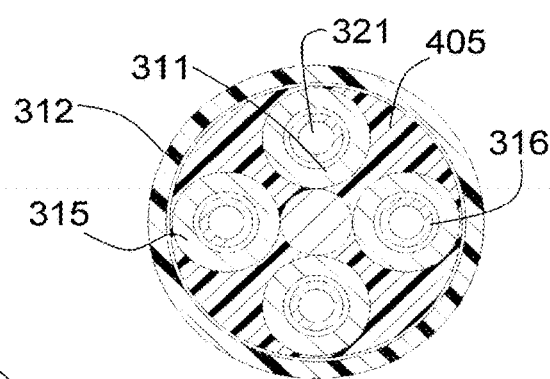
FIG. 23 is a circumferential cross section at S23-S23 of the INAS central transition portion of FIG. 20.

FIG. 23 is a circumferential cross section at S23-S23 of the central transition section 460 of FIG. 20. This cross section is identical to the circumferential cross section shown in FIG. 13 showing the sheath 312 and plastic member 405 (was 305 in FIG. 13) that seals and attaches together the four guide tubes 315 and the core wire 311. The injector tubes 316 lie concentrically inside of the four guide tubes 315. Thus, FIGS. 20-23 clearly show how the simplified proximal end of FIG. 19 connects to the distal portion of the INAS 300 of FIGS. 11-15.

Figure 24:
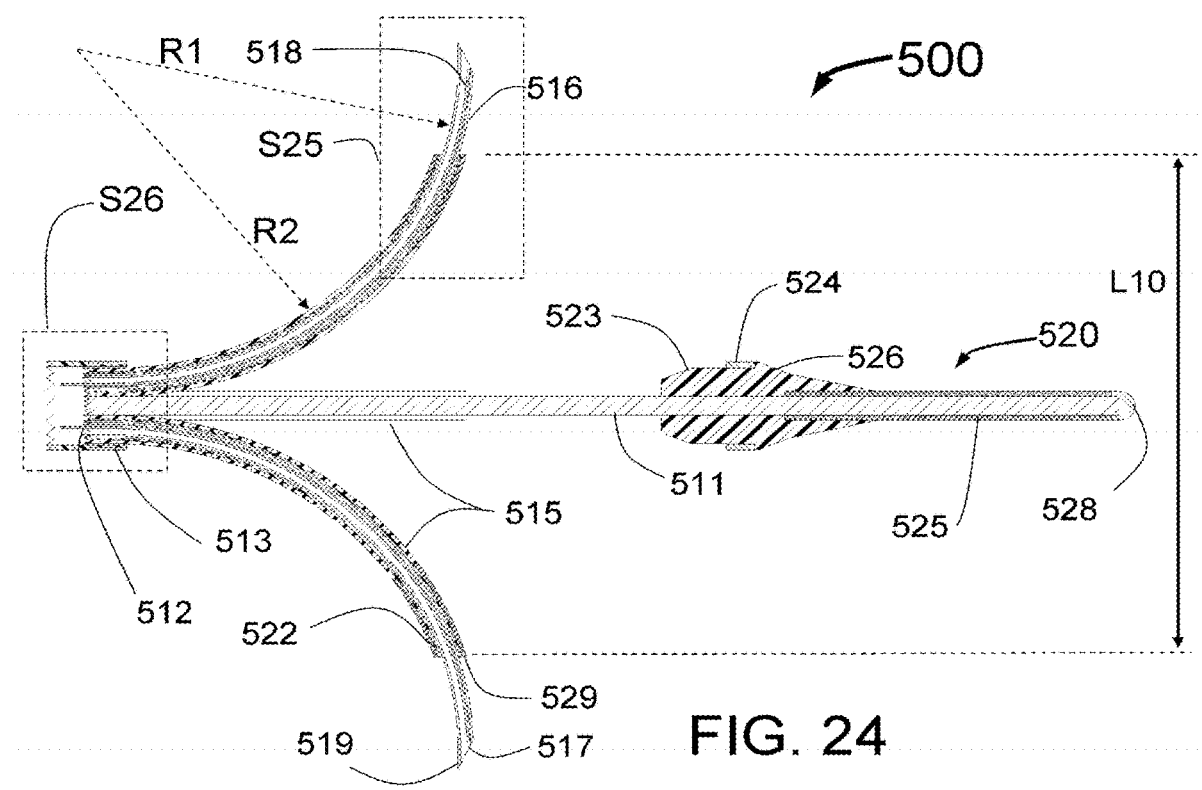
FIG. 24 is a longitudinal cross section of the proximal end of an alternate embodiment of the INAS having coring needles with radiopaque wires in their lumens to provide visualization of the needles when deployed.

FIG. 24 is a longitudinal cross section of the proximal end of an alternate embodiment of the INAS 500 having injector tubes 516 with coring needles 519 with radiopaque wires 518 in their lumens to provide visualization of the needles when deployed. The radiopaque wires 518 would typically extend beyond the proximal end of the injector tubes 516 where they would be attached to the structure of the INAS 500. While the preferred configuration has the radiopaque wires 518 simply within the lumen of the injector tubes 516, it is also envisioned that the radiopaque wires could be fixedly attached inside the injector tubes using adhesive or brazing. If such attachment is used than the radiopaque wires can be shorter then the injection tubes 516 and positioned in the most distal portion.

In this embodiment the injection egress ports 517 are at the distal end of the coring needles 519. In this configuration the sheath 512 has been pulled back to allow the guide tubes 515 to expand outward. The guide tubes 515 in this embodiment are made from one or two layers of plastic preformed in the expanded curved shape. The injector tubes 516 may be made from any metal such as 316 surgical grade stainless steel, NITINOL or a radiopaque metal such as tantalum or platinum. In this embodiment the distal portion of each guide tube 516 has a radiopaque section 522 that is formed integral to the guide tube and is typically made of a radiopaque plastic such as barium or tungsten filled urethane. Also shown in FIG. 24 are the distal ends 529 of the guide tubes 515 that in the fully open configuration at the diameter L10 are parallel to the longitudinal axis of the INAS 500. For use in the renal arteries, L10 would typically be between 3 and 10 mm with 8 mm being a best configuration if only one size is made as very few renal arteries are larger than 7 mm diameter.

It is important to have the distal ends 529 of the guide tubes touch as close as possible to flat against the inside of the renal artery for if the angle is too acute then the needles 519 might not properly puncture the arterial wall. It also turns out that when plastic is used for the guide tubes 515, although formed in a curved shape, the shape can become somewhat straightened when pulled back for an extended period of time into the sheath. For this reason, it is envisioned that the INAS 500 would be packaged in its open configuration so as to reduce the time the guide tubes would be in a straight shape within the sheath.

It is also suggested that the initial shape of the guide tubes 516 would have the ends 529 actually shaped in the fully open position to curve back further than the 90 degrees shown in FIGS. 14 and 24. For example, if the initial angle was 135 degrees at 8 mm diameter which is the position for the fully open INAS 500 as formed, then at 7 mm diameter the angle could be at 120 degrees, at 6 mm-105 degrees, at 5 min-90 degrees, at 4 mm 75 degrees and at 3 mm 60 degrees. Thus the needles 519 would engage the vessel wall between 60 and 120 degrees for vessels between 3 and 7 mm in diameter. Thus, in this example, FIG. 24 would be the shape of the INAS 500 within a 5 mm diameter vessel.

Figure 26:
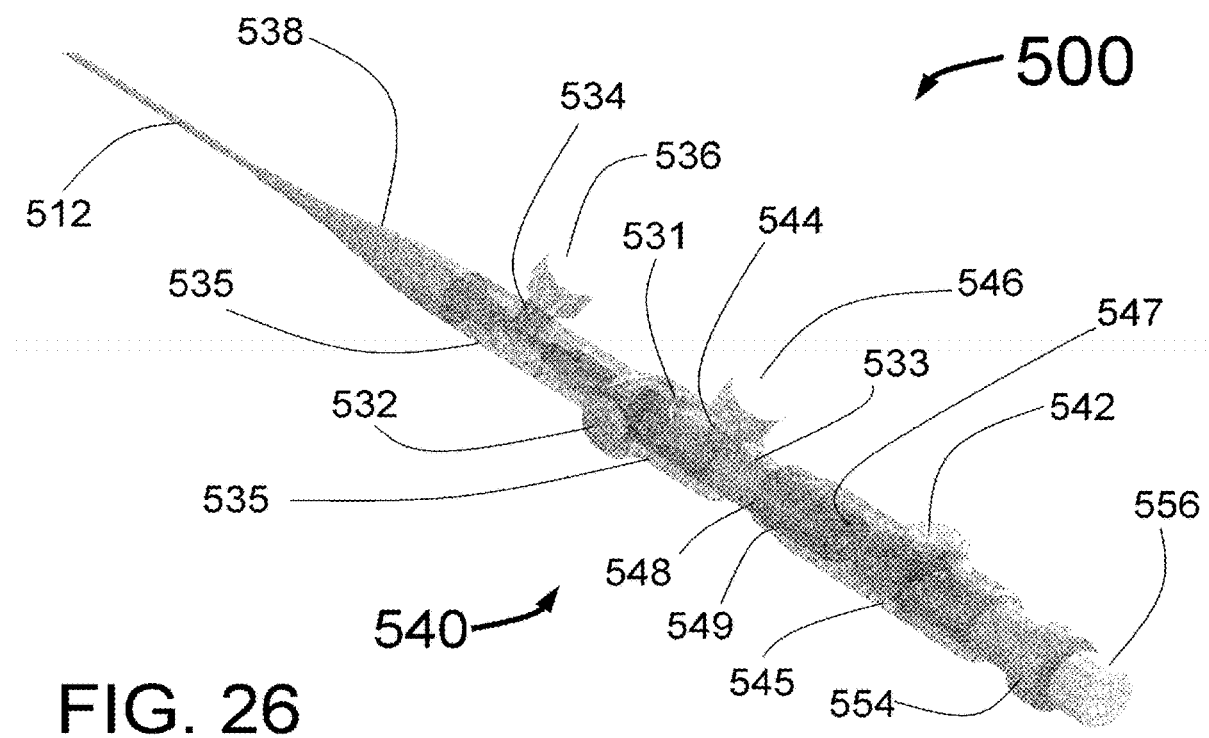
FIG. 26 is a schematic view of an embodiment of the INAS proximal portion having locking mechanisms activated by press-able buttons.

The distal portion of the INAS 500 has the tapered section 526 attached to the fixed guide wire 520 with tip 528, having an outer layer 525 and core wire 511. The distal end of the sheath 512 with distal radiopaque marker 513 is also shown. An enlarged view of section S26 is shown in FIG. 26.

FIG. 25A is an enlargement of the area S25 of FIG. 24 as it would appear with the distal end of the injector tube 516 with lumen 521 and distal needle 519 fully advanced beyond the distal end 529 of the guide tube 515. The radiopaque wire 518 is clearly shown within the lumen 521 of the injector tube 516. The injector tube 516 would typically be smaller than a 25 guage needle and ideally less than 0.015" in diameter with the lumen 521 being at least 0.008" in diameter. Thus the radiopaque wire 518 must be sufficiently less than the diameter of the lumen 521 so as not to impede injection but still large enough in diameter to be visible under fluoroscopy. Thus an ideal diameter of 100002" to 0.006" should work with a diameter of 0.004" to 0.005" being ideal. The preferred outside and inside diameters for the injector tube 516 would be 0.012" to 0.014" with the lumen 521 between 0.008" and 0.010".

In addition the guide tube 515 is shown with an inner plastic layer 527 an outer plastic layer 531 and the radiopaque marker 522. The radiopaque marker 522 is shown here molded over the inner plastic layer 527 distal to the end of the outer plastic layer 531. The radiopaque marker 522 should be at least 0.5 mm long with 1-2 mm being preferred. For example, the inner plastic layer 527 might be Teflon or polyimid, while the outer layer 531 might be a softer plastic such as urethane or tecothane. Ideally, the distal end 529 of the guide tube 515 would be soft enough so as to reduce the risk of penetration of the vessel wall when it touches during deployment. It is also envisioned that a metal band made of gold, platinum or tantalum could also be used to mark the distal end of the guide tube 515. It is also envisioned that the outer layer 531 and the radiopaque marker 522 could be the same so that the entire guide tube 516 would be visible under fluoroscopy.

The use of the radiopaque wires 518 also reduces the dead space within the injector tubes 516 as it is important to minimize the amount of volume within the entire INAS 500 with the ideal volume being less than 0.2 ml. This will facilitate a reduced time injection method for PVRD that would have the INAS 500 flushed with saline to begin.

One technique envisioned to decrease the dead space inside any of the injection lumens of the INAS is to have a wire inside the lumen just like the wire 518 inside of the lumen 521 to take up volume. Similarly, a wire could be inserted into the lumen 421 of the inner tube 416 of FIG. 20 to take up volume in the lumen 421.

Once in place with the needles through the renal artery wall, the proper amount of ablative fluid would be infused. Enough saline would then be injected to completely flush all of the ablative fluid out of the INAS 500. The INAS 500 would be closed and the $2^{nd}$ renal artery treated the same way. The INAS 500 would then be removed from the body. The radius of curvature R1 of the distal portion of the injector tube 516 should be approximately the same as the radius of curvature R2 of the guide tube 515, This will prevent the guide tubes 515 from moving proximally (hacking up) as the needles 519 puncture the vessel wall. Thus R1 and R2 should be within 2 mm of each other. It is also envisioned that if the radii of curvature are significantly different then the radius of curvature R1 should be less than R2.

In reality the radius of curvature of the distal portion of each guide tube 515 will vary with the diameter of the vessel, being tamer for smaller vessels that will constrain the guide tubes 515 not allowing them to completely open up. Thus ideally, the radius of curvature of the distal portion of each injector tube 516 including the injection needle 519 should be approximately the same as that of the proximal portion of the guide tubes 515 when the guide tubes 515 are expanded to their maximum diameter.

The needles 519 extend a distance L11 beyond the distal ends 529 of the guide tubes 515. This distance would typically be between 2 and 4 mm with the preferred distances being 2.5, 3.0 and 3.5 mm assuming the INAS 500 distance L11 is preset in the factory.

FIG. 25B is an alternate embodiment of the distal section S25 of the INAS 500 of FIG. 24. FIG. 25B has the same structure as FIG. 25A for the injector tubes 516 with injector needles 519 having injection egress 517 and radiopaque wires 518. The difference from FIG. 25A is the means of radiopaque marker for the guide tube 515. In FIG. 25B, the guide tube 515 also has an inner layer 527 and outer layer 531 with distal end 529. The metal radiopaque marker band 505 is attached to the outside of the guide tube 515 close to the distal end 529. The combination of a metal band 505 to show the distal end of the guide tube 515 in with the radiopaque wire 518 to show the extension of the injector tube 516 with injection needle 519 provide a great combination for visualization the key portion of the INAS 500 to ensure that the injection egress 517 is properly situated before the ablative fluid in injected.

FIG. 26 is a schematic view of an embodiment of the proximal section 540 (or handle) of the INAS 500 having locking mechanisms activated by press-able buttons 532 and 542. Specifically, button 532 when depressed unlocks the motion of the sheath control cylinder 535 with respect to the guide tube control cylinder 533. The sheath control cylinder 535 is attached to the sheath 512 by the transition section 538. The guide tube control cylinder 533 is attached to the middle tube 505 of FIG. 28 that in turn is connected to the guide tubes 515 of FIGS. 24, 25 and 28. The sheath control cylinder 535 includes a notch 531 that is used to limit the pull back in the proximal distance of the sheath 512.

The button 542 when depressed, unlocks the motion of the needle control cylinder 545 with respect to the guide tube control cylinder 533.

The handle 540 has two flushing ports. Port 534 which would typically have a Luer fitting is shown with a cap 536. Port 534 is used to flush with saline the space 507 shown in FIG. 28 between the sheath 512 and the middle tube 505 as well as the space between the sheath 512 and the guide tubes 515. Port 544 which would typically have a Luer fitting is shown with cap 546. Port 544 is used to flush with saline the space 508 between the middle tube 505 and the inner tube 506. The injection port 554 which typically has a Luer fitting is shown with cap 556. Port 554 allows injection of the ablative fluid into the lumen 521 of FIG. 28 which is in fluid communication with the lumens of the injector tubes 516.

Figure 25:
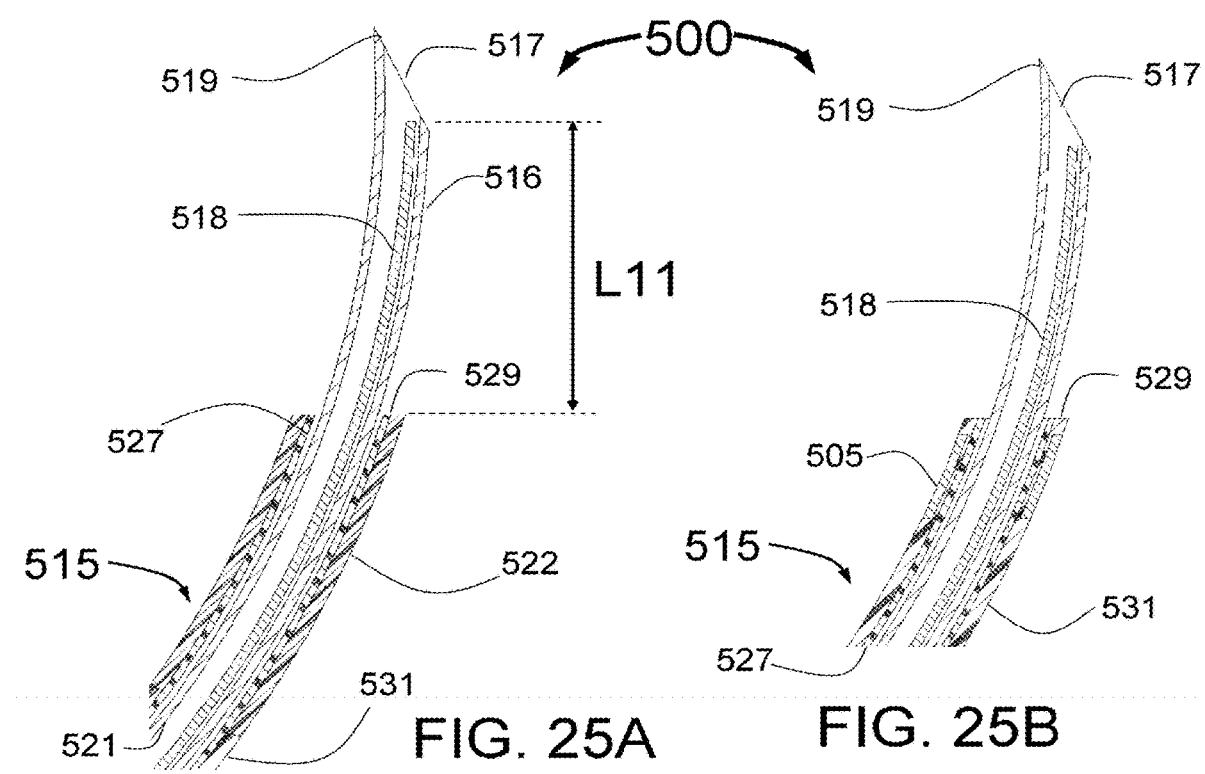
FIG. 25A is longitudinal cross section showing an enlargement of the distal portion of a guide tube and coring needle of the INAS of FIG. 24.
FIG. 25B is an alternate embodiment of the distal section S25 of the INAS of FIG. 24 with the same structure as FIG. 25A for the injector tubes but with a metal band as a radiopaque marker for the guide tube.

The handle 540 also includes a gap adjustment cylinder 548 that when rotated in one direction reduces the distance the injection needles 519 extend beyond the end of the guide tubes 515. Rotation in the other direction of the cylinder 548 will increase the distance the injection needles 519 extend beyond the distal ends 529 of the guide tubes 515. It is envisioned that the gap adjustment cylinder could be accessible to the user of the INAS 500 with markings on the handle 540 to indicate the distance that will be achieved. In a preferred embodiment the gap adjustment cylinder 548 could be accessible only during assembly and testing of the INAS 500 to ensure a properly calibrated, distance L11 of FIG. 25 is preset in the factory during manufacturing and testing of each INAS 500. This ability to calibrate the distance L11 is critical to a good yield during manufacturing. In other words, even with variation of a few millimeters in the relative lengths of the components of the INAS 500 such as the inner tube 506 and middle tube 505, the distance L11 can be dialed in exactly using the gap adjustment cylinder 548. In this preferred embodiment, the INAS 500 would be labeled according to the preset distance L11 shown in FIG. 25. For example, the INAS 500 might be configured to have three different distances L11 of 2.5 mm, 3 mm and 3.5 mm. It is also envisioned that a set screw or other mechanism not shown could be included to lock the gap adjustment cylinder 548 at the desired distance setting after calibration. While a gap adjustment cylinder 548 is shown here, it is envisioned that other mechanisms such as a sliding cylinder could also be used to adjust the distance L11.

The function of the handle 540 to operate the INAS PVRD would include the following steps:

1. Flush all of the internal volumes of the INAS 500 with normal saline through the ports 534, 544 and 554.
2. Insert the INAS 500 through a previously placed guiding catheter positioning the distal portion of the INAS 500 at the desired location in one renal artery of the patient,
3. Depress the button 532 and while holding the needle control cylinder 545 which is locked to the guide tube control cylinder 533, pull the sheath control cylinder 535 in the proximal direction until the notch 531 engages the port 544 limiting the pull back of the sheath 512,
4. Release the button 532 which relocks the relative motion of the sheath control cylinder 535 with respect to the guide tube control cylinder 533.
5. Depress the button 542 that release relative motion of the injection needle control cylinder 545 with respect to the guide tube control cylinder 533 and while holding the sheath control cylinder 535 which is now locked to the guide tube control cylinder 533, advance the needle control cylinder 545 with distal end 549 until the penetration limiting mechanism stops the motion and the preset depth Lit of the needles 519 with respect to the distal ends 529 of the guide tubes 515. There are two ways this can be done: 1) The distal end 549 of the needle control cylinder 545 is pushed forward until it engages the guide tube flush port 544 or 2) the internal gap 547 is closed against the proximal end of the gap adjustment cylinder 548 inside the needle control cylinder 545 as shown in FIG. 26.
6. Release the button 542 which relocks the motion of the injection needle control cylinder 545 to the guide tube control cylinder 533.
7. In this position a syringe or manifold with syringes shown) can be attached to the port 554 and the desired volume of ablative fluid is injected. For example 0.2 ml of ethanol could be injected. If it is desired to verify the position of the INAS 500 needles 519, angiography can be performed looking down the length of the renal artery such that concentrically one would see the radiopaque rings 513 and 524 on the distal end of the sheath 512 and tapered distal end 520, outside of that the radiopaque markings on the guide tubes 522 and extending into the wall of the renal artery and into the peri-vascular space, the distal portion of the injector tubes 516 with internal radiopaque wires 518. This can be done with or without contrast injection into the renal artery
8. Next a syringe with normal saline solution is attached to the port 554 replacing the ablative fluid syringe. Ideally, slightly more saline is injected than the total volume of dead space to ensure there is no ablative fluid left in the INAS 500. For example, if the dead space in the INAS 500 is 0.1 ml then 0.12 to 0.15 ml of saline would be a good amount to ensure the ablative fluid is all delivered to the appropriate peri-vascular volume of tissue.
9. Depress the button 542 and while holding the sheath control cylinder 535, pull the needle control cylinder 545 back in the proximal direction until the injection needles 519 are fully retracted back inside the guide tubes 515. It is envisioned that a click or stop would occur when the injection needle control cylinder 545 reaches the correct position so that the injection needles 519 are fully retracted.
10. Release the button 542 locking the motion of the injection needle control cylinder 545 to the guide tube control cylinder 533.
11. Depress the button 532 releasing the relative motion of the sheath control cylinder 535 with respect to the guide tube control cylinder 533 that is now locked to the injection needle control cylinder 545.
12. Advance the sheath control cylinder 535 in the distal direction while holding the injection needle control cylinder 545 fixed. This will close the INAS 500, collapsing the guide tubes 515 back inside the sheath 512.
13. Pull the INAS 500 back into the guiding catheter.
14. Move the guiding catheter to the other renal artery.
15. Repeat steps 3 through 13 for the other renal artery
16. Remove the INAS 500 from the body.

While the buttons 532 and 542, as described above, release the motion of control cylinders when depressed and lock when released, it is also envisioned that they could also be interlocked as follows:

1. The first interlock allows the injection needle control cylinder 545 to be unlocked only when the sheath control cylinder 535 is in its most distal position where the sheath 512 is pulled hack and the guide tubes 515 are fully deployed.
2. The second interlock allows the sheath control cylinder 535 to be unlocked only when the injection needle control cylinder 545 is in its most distal position where the needles 519 are retracted within the guide tubes 515.

The combination of the buttons 532 and 542 with the control mechanisms described above should make the use of the INAS 500 simple and foolproof. One basically presses button 532 and pulls the sheath 512 back releasing the guide tubes 515 to expand outward, then press button 542 and advance the needles 519 forward to penetrate the wall of the renal artery. Injections are performed then the reverse is done with button 542 depressed and the needles 519 retracted, then button 532 depressed and the sheath 512 pushed forward collapsing the guide tubes 515 and closing the INAS 500.

FIG. 27 is a schematic view of the needle section of another embodiment of the present invention INAS 550 having a core wire 561 formed from three twisted wires 561A, 561B and 561C and non circular cross section guide tubes 565 having radiopaque distal section 572 and distal ends 579. The INAS 550 is somewhat similar to the INAS 500 of FIG. 24. It has a sheath 512 with distal radiopaque marker 513, injector tubes 566 with distal injection needles 569 and injection egress ports 567. The tapered distal section 580 has a tapered section 576, a radiopaque marker 574 and a proximal section 573. Of significant importance in this embodiment is the backward curved shape of the injector tubes 566 with injection needles 569. Specifically, the radius of curvature of the injector tubes 566 should match or be slightly smaller (more curved than) the radius of curvature of the guide tubes 565 and the guide tube distal radiopaque sections 572. This will prevent straightening of the guide tubes 565 including the distal radiopaque sections 572 as the needles 569 penetrate the wall of the target vessel. FIG. 27 shows the fully deployed shape of the INAS 550 where the center of the injection egress ports 567 are proximal by a distance L12 from the center of the distal ends 579 of the guide tubes 565 with radiopaque section 572. L12 should be between 0.5 mm and 5 mm.

FIG. 28 is the central portion of a transverse cross section at S28-S28 of the INAS 550 with sheath 512 of FIG. 27. It shows the non circular cross section guide tube 565 surrounding the injector tubes 566. At the position S28-S28, the middle tube 564 which is connected to the guide tube control cylinder 533 of FIG. 26, is fixedly attached to the outsides of the three guide tubes 565 as well as the three wires, 561A, 561E and 561C which twist together to become the core wire 561 as shown in FIG. 27. This can be accomplished by injecting plastic or adhesive to in the connective media 555 within the lumen of the middle tube 564.

Figure 29:
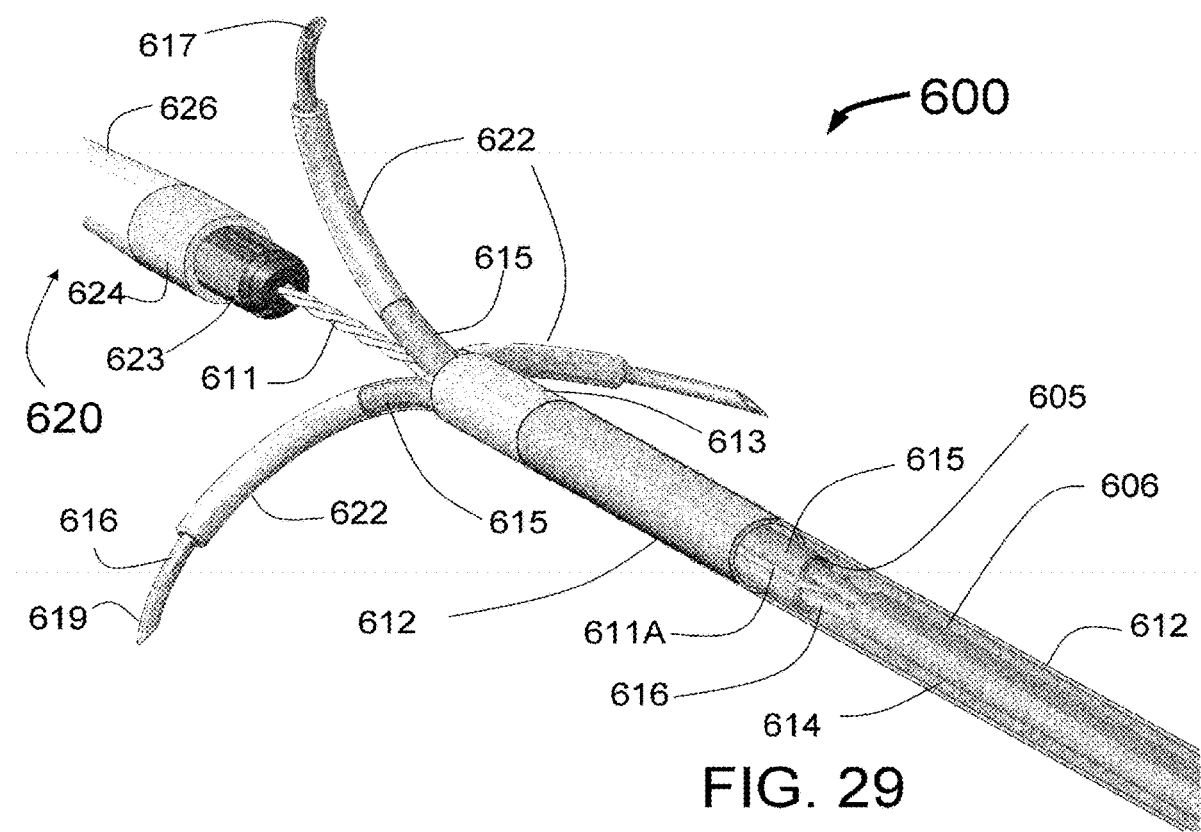
FIG. 29 is a schematic view of a distal portion of yet another embodiment of the INAS having a twisted core wire with circular cross section guide tubes.

FIG. 29 is a schematic view of a distal portion of yet another embodiment of the INAS 600 having a twisted core wire 611 with circular cross section guide tubes 615 having distal radiopaque sections 622.

With the exception of the twisted core wire 611 and three rather than 4 injection needles, the INAS 600 is somewhat similar to the INAS 500 of FIG. 24. It has a sheath 612 with distal radiopaque marker 613, injector tubes 616 with distal injection needles 619 and injection egress ports 617. It also has the radiopaque wires 618 that lie within the injector tubes 616 to assist in visualization during fluoroscopy. The tapered distal section 620 has a tapered section 626, a radiopaque marker 624 and a proximal section 623. Similar to the INAS 550 of FIGS. 27 and 28, this embodiment has a backward (proximal) curved shape of the injector tubes 616 with injection needles 619. Specifically, the radius of curvature of the injector tubes 616 should match or be slightly smaller (more curved than) the radius of curvature of the guide tubes 615 and the guide tube distal radiopaque sections 622. This will prevent straightening of the guide tubes 615 including the distal radiopaque sections 622 as the needles 569 penetrate the wall of the target vessel.

For better visualization, in FIG. 29, the proximal portion of the sheath 612 and middle tube 614 are shown as transparent so the internal structure of the INAS 600 is evident. Specifically, the three circular cross section guide tubes 615 would be connected to the middle tube 614 using a technique similar to the INAS 550 of FIG. 28. Also shown is the wire 611A which is one of the three wires that twist together to form the core wire 611 also as shown in FIGS. 27 and 28. The inner tube 606 which connects to the needle control cylinder 545 of FIG. 26, is internally attached to the three injector tubes 616 using a manifold (not shown) similar to that of the manifold 410 of FIG. 20. The three injector tubes 616 are shown as they enter the proximal end 605 of the three guide tubes 615.

Figures 30, 31:
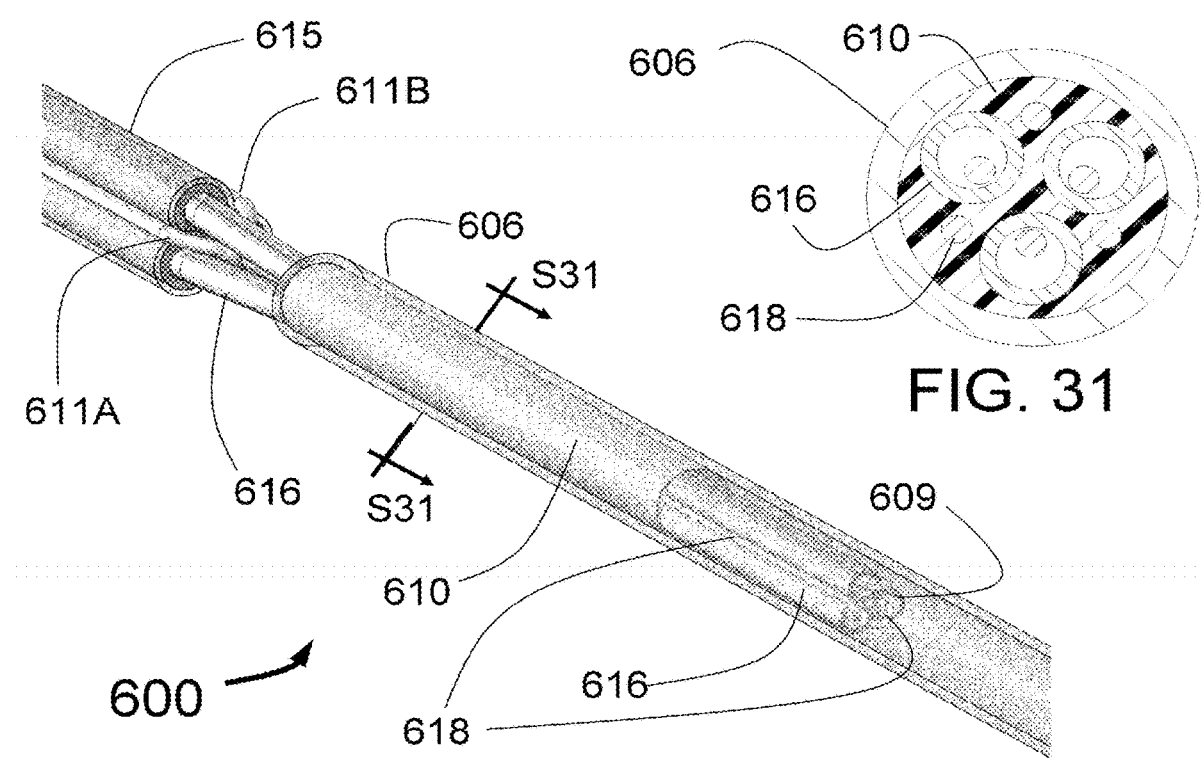
FIG. 30 is a schematic view of the inner portion of the INAS that clearly shows the proximal end of the radiopaque wires that run the length of the injector tubes to provide radiopacity.
FIG. 31 is the transverse cross section at S31-S31 of FIG. 30.

FIG. 30 is a schematic view of the inner portion of the INAS 600 that clearly shows the proximal end of the radiopaque wires 618 that run the length of the injector tubes 616 to provide radiopacity. These radiopaque wires 618 are similar to the radiopaque wires 518 of FIGS. 24 and 25. Clearly visible in this inner portion which has the sheath 612 and middle tube 614 removed, is the inner tube 606 which is transparent, the 3 guide tubes 615, the three injector tubes 616, 611A and 611B which are two of the component wires of the core wire 611 of FIG. 29. The manifold 610 is shown in FIG. 30 as being inside the inner tube 606, The distal portion of the manifold 610 is shown with the proximal portion being transparent. Although not shown, the proximal transparent portion of the manifold 610 extends all the way to the proximal end of the injector tubes 616 similar to the manifold 410 of FIG. 20. Finally, the radiopaque wires 618 which exit the proximal end of the injector tubes 616 are folded back and run back in the distal longitudinal direction in the space beside the injector tubes 616.

Figures 32A, 32B:
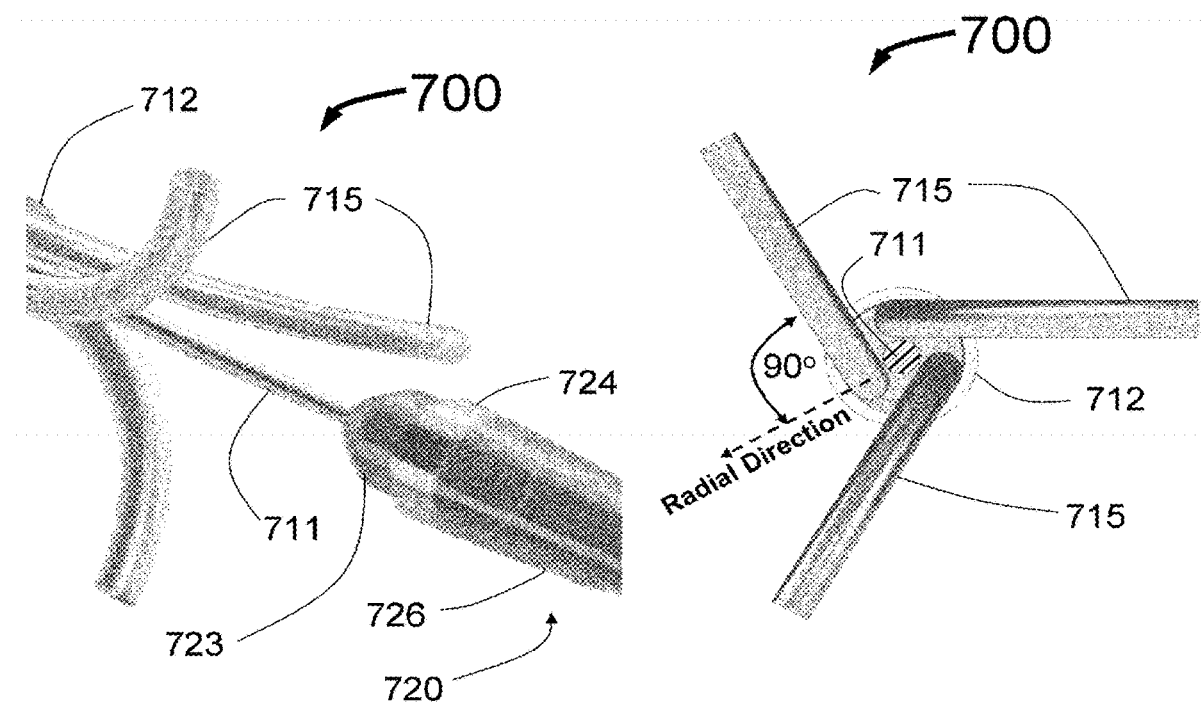
FIG. 32A is a schematic view of an embodiment of the INAS distal portion having non-circular guide tubes.
FIG. 32B is an end on schematic view showing the guide tubes of FIG. 30A

As shown in FIG. 31 which is the transverse cross section at S31-S31 of FIG. 30, the manifold 610 that is either molded or injected plastic or adhesive, seals together the inside of the inner tube 606 with the three injector tubes 616 and three radiopaque wires 618. In the full catheter 600 not just the inner portion FIG. 32A is a schematic view of an embodiment of the INAS 700 distal portion having non-circular guide tubes 715. Also shown is the core wire 711 and tapered with an elliptical or oval cross section. The tapered distal section 720 has a tapered section 726, a radiopaque marker 724 and a proximal section 723. The distal end of the sheath 712 is just visible. The guide tubes 715 in this embodiment can be made of NITINOL or a formed plastic such as polyamid. The advantage of the non-circular cross section of the guide tubes 715 is to provide better support for the injector tubes (not shown) as they are pushed distally to engage the inside watt of the target vessel.

FIG. 32B is an end on schematic view of the 32A looking in the proximal direction, just proximal to the proximal end of the tapered distal section 720. Here you can see that rather than the guide tubes 715 being oriented to expand outward in a purely radial direction, the guide tubes 715 are rotated 90 degrees to the radial direction to allow the non-circular cross section to have a reduces impact on catheter diameter. The core wire ill is seen in cross section as well as the distal end of the sheath 712.

Figure 33:
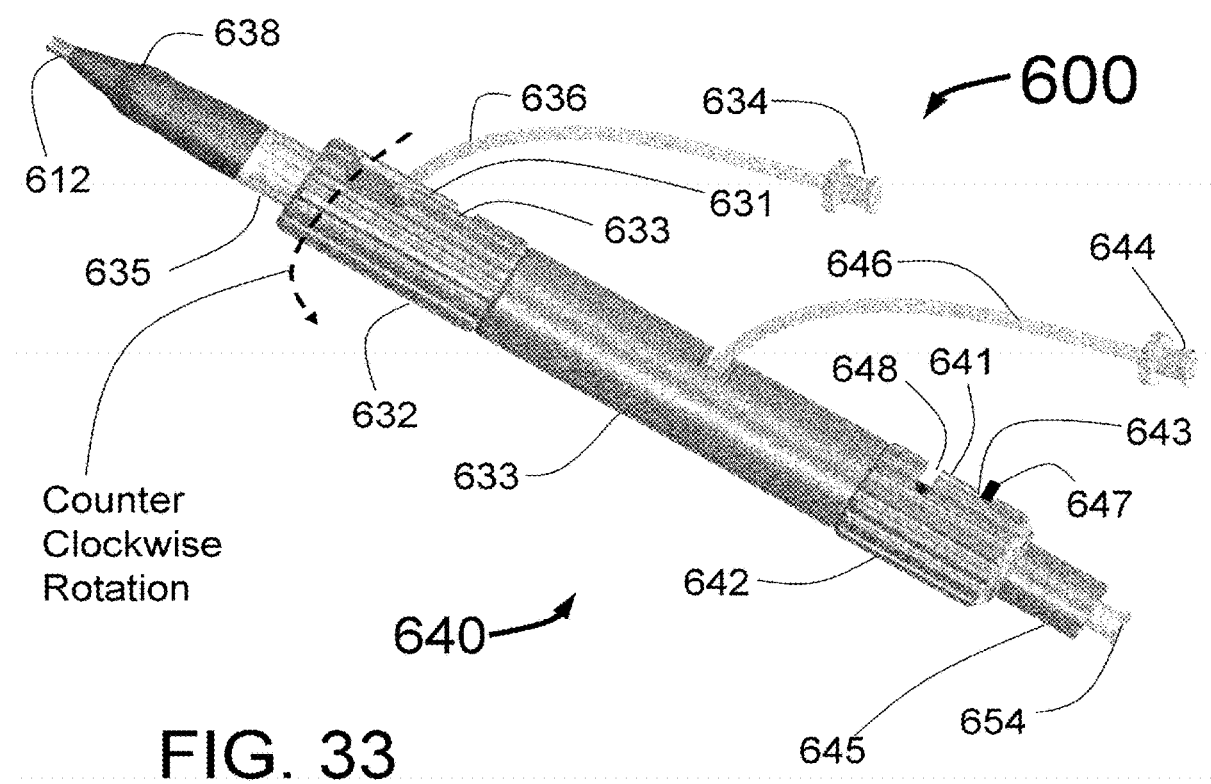
FIG. 33 is a schematic view of an alternate embodiment of the INAS handle which uses rotation of members to lock and unlock motion between the moving sections.

FIG. 33 is a schematic view of an embodiment of the proximal section/handle 640 of the INAS 600 having locking mechanisms activated by rotation of the sheath control lock 632 and the needle control lock 642. Specifically rotation of the sheath control lock 632 counter clock wise form the position shown in FIG. 33 until the sheath flush tube 636 with Luer port 634 lines up with the longitudinal slot 631 will unlock the motion of the sheath control cylinder 635 which is attached to the sheath 612 through the tapered section 638. The sheath control cylinder 635 and tapered section 638 can now be pulled in the proximal direction with respect to the guide tube control cylinder 633 to retract the sheath with respect to the guide tubes as seen in the configuration of FIG. 29. Once the sheath control cylinder 635 is pulled all the way back in the proximal direction, the sheath flush tube 632 will now line up with the circumferential slot 633 which extends in the clockwise direction within the sheath control lock 632. In this position, the sheath control lock can be rotated further in the counter clockwise direction so that the sheath flush tube 636 lies within the circumferential slot 633 and prevents longitudinal motion of the sheath control cylinder 635. It is envisioned that springs could be embedded in this mechanism so that once the sheath flush tube 636 is lined up with the slot 633 the sheath control lock 632 would automatically spring to the locked position.

Once the sheath 612 has been retracted in the proximal direction as described above, the handle is ready to have the injector tubes 616 with injection needles 619 of FIG. 29 advanced distally to penetrate the vessel wall of the target vessel. The circumferential slots 643 and 648 are connected by the longitudinal slot 641. A locking pin 647 attached to the outside of the needle control cylinder 645 tracks within the three slots 643, 641 and 648 to lock and unlock the relative motion of the guide tube control cylinder 633 with respect to the needle control cylinder 645. To enable advancement of the injector tubes 616 of FIG. 29, the needle lock cylinder 642 is rotated in the clockwise direction to align the pin 647 with the longitudinal slot 641. The needle control cylinder 645 can now be moved in the distal direction causing the injector tubes 616 to advance distally. When the pin 647 now reaches a position aligned with the circumferential slot 648, it can no longer move any more in the distal direction and the penetration of the needles 619 is therefore limited. In this configuration, additional clockwise rotation of the needle lock cylinder 642 will move the pin 647 into the circumferential slot 648 which will low lock longitudinal motion of the needle control cylinder 645. A syringe can now be attached to the Luer fitting 654 and appropriate ablative fluid injected into the peri-vascular space as desired. An additional injection of saline or other inert fluid to flush the internal dead space of the INAS 600 and ensure full delivery of all the ablative fluid to the desired site would now be done. The reverse of the sheath 612 retraction and injector tube 616 distal motion can now be accomplished by the reverse motion of the components of the handle 640.

It is also envisioned that the proximal section 640 can be built such that the reverse direction of rotation of any of the steps above would work. Also the combination of rotational motion such as described for the proximal section/handle 640 of FIG. 33 with a button lock/unlock mechanism such as is shown in the proximal section/handle 540 is clearly envisioned here.

Figures 34, 35:
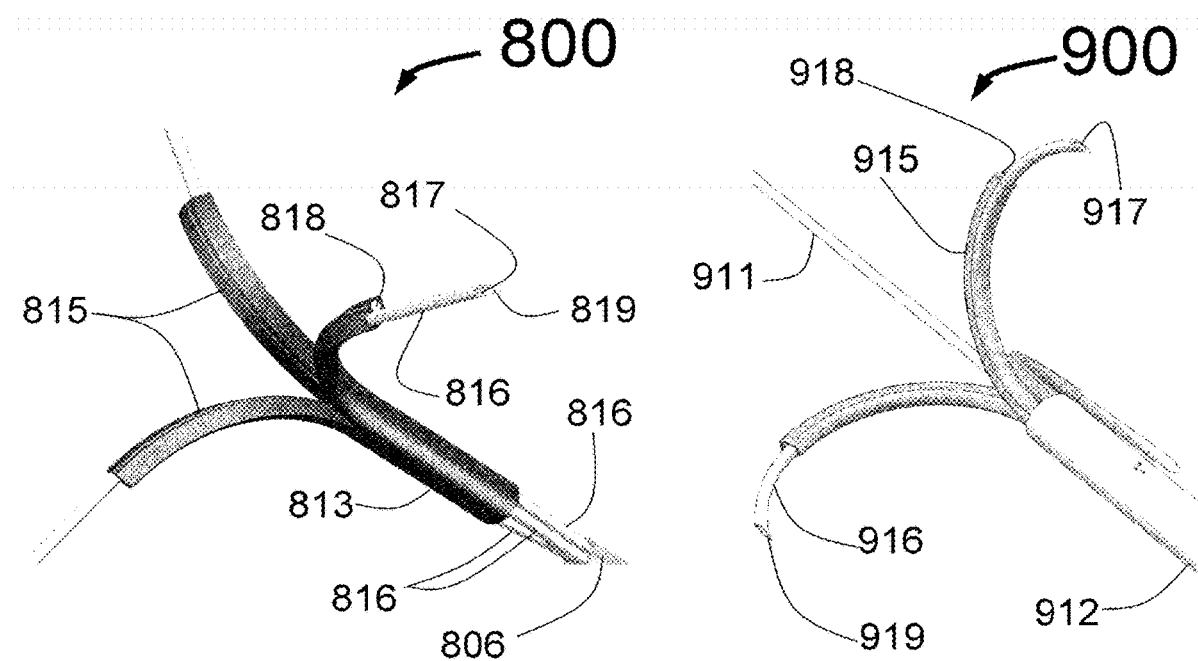
FIG. 34 is a schematic view of the guide tubes and injection tubes of another embodiment of the present invention INAS having three guide tubes that separate from a main guide wire body.
FIG. 35 is a schematic view of yet another embodiment of the present invention INAS having injector tubes with distal needles having injection egress ports.

FIG. 34 is a schematic view of the guide tubes 815 and injector tubes 816 of another embodiment of the present invention INAS 800 having three guide tubes 815 that separate from a main guide wire body 813. Each guide tube 815 has two lumens, on for passage of the injector tubes 816 and the other for a wire 818 which provides the shape memory that causes the guide tubes 815 to open up against the inside vessel wall of the target vessel. The wire 818 can also provide additional radiopacity for visualization of the guide tubes 815. The guide tubes 815 and guide tube body 813 in the INAS 800 would be made from a plastic material, soft enough to allow the wire 818 to cause the guide tubes 815 to form the shape shown. It is also envisioned that the guide tubes 815 themselves would include a radiopaque material such as Tungsten or Barium. The wires 818 could be made from a shape memory alloy such as NITNOL or from a pre-shaped spring material such as spring steel. Also show is the proximal end of the inner tube 806 which attaches to the injector tubes 816 with distal ends having sharpened injection needles 819 with injection egress 817.

FIG. 35 is a schematic view of yet another embodiment of the present invention INAS 900 having injector tubes 916 with distal needles 919 having injection egress ports 917. The INAS 900 also has three guide tubes 915 that include a flat wire 918 inside of the guide tube 915. The flat wire 918 provides the shape memory and optionally the radiopacity for visualization of the guide tubes 915. The flat wire 918 would typically be made from a memory metal such as NITINOL, or a spring material such as spring steel. The guide tubes 915 would typically be made from a plastic material, soft enough to allow the re 818 to cause the guide tubes 815 to form the shape shown. Also show is the sheath 912 and core wire 911 which are similar in function to those shown in many of the earlier embodiments of the INAS, It is also envisioned that the guide tubes 915 themselves would include a radiopaque material such as Tungsten or Barium.

While each of the INAS embodiments shown herein have closed and open positions where the close position has the injection needles completely enclosed, it is envisioned that the system would function with an outer sheath that is open at its distal end such as is shown in the McGuckin device of U.S. Pat. No. 7,087,040. In such an embodiment, needlestick injuries could be prevented by withdrawing the injection needles back in the proximal direction a sufficient distance that they are hidden. An interlock in the proximal section and/or handle could lock the motion of the needles to prevent them from accidentally moving in the distal direction. This concept would work with the INAS designs of FIGS. 1-10 as well as those embodiments with guide tubes shown in FIGS. 11-35 where the needles would be retracted proximally within the guide tubes and then the guide tubes would be retracted back into the sheath.

Figures 36A, 36B, 36C:
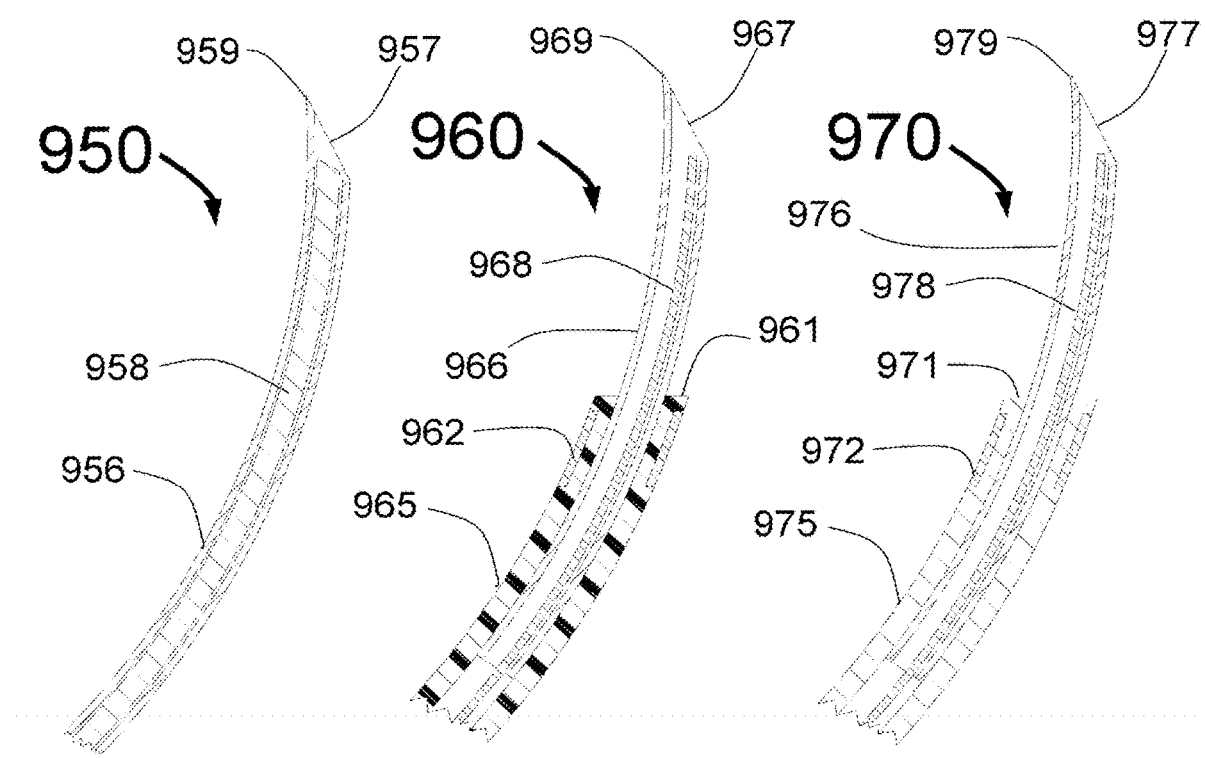
FIG. 36A is a longitudinal cross section view of another embodiment of the distal portion of an injection needle.
FIG. 36B is a longitudinal cross section view of still another embodiment of the distal portion of a plastic injector tube, with an injection needle inserted into its distal end.
FIG. 36C is a longitudinal cross section view of another yet another embodiment of the distal portion of a metal injector tube with an injection needle inserted into its distal end.

FIG. 36A is a longitudinal cross section view of another embodiment of the distal portion of an injector tube 956 with distal injection needle 959 of the INAS 950. The other structure of the INAS 950 is similar to the INAS 10 of FIG. 1. The injection needle 959 has injection egress 957. A stylette 958 is shown inside the lumen of the injector tube 956. The stylette 958 has two potential uses, 1) it can stiffen the injector tube 956 to it will maintain its proper curved shape and better penetrate the inside wall of the target vessel and 2) it could provide additional radiopacity for visualization under fluoroscopy. It is also envisioned that the injection needle 959 could have a non sharp end and the stylus 958 could extend beyond the injection egress 957 and be sharpened to provide means to penetrate the inside wall of the target vessel. The stylette 958 would be removed completely or pulled back so as not to obstruct flow once the needles are properly positioned. A cord such as the cord 13 of the INAS 10 of FIG. 1 could provide the means to limit penetration depth in this design.

FIG. 36B is a longitudinal cross section view of still another embodiment of the distal portion of a plastic proximal tube 965 of the INAS 950 with an injector tube 966 with distal injection needle 969 inserted into the distal end of the injector tube 965. Radiopacity is provided by a radiopaque marker hand 962 on the injector tube 965 and a radiopaque wire 968 inside of the injector tube 966. The injection needle 969 has injection egress 957. The injector tube 965 would be made from a pre-shaped plastic such as urethane or polyamide or a combination of two or more layers of plastic. The distal end. 961 of the injector tube 965 provides the means to limit penetration of the needle 969. It is also envisioned that the injector tube 966 can be made from a radiopaque metal such as tantalum or L605 cobalt chromium or the injector tube 966 could be plated or coated with a radiopaque metal such as gold. In those cases, there would not be a need for the radiopaque wire 968

FIG. 36C is a longitudinal cross section view of still another embodiment of the distal portion of a metal proximal tube 975 with an injector tube 976 with distal injection needle 979 inserted into the distal end of the injector tube 975. Radiopacity is provided by a radiopaque marker band 972 on the injector tube 975 and a radiopaque wire 978 inside of the injector tube 976. The injection needle 979 has injection egress 977. The injector tube 975 would be made from a pre-shaped metal such as NITINOL. The distal end 971 of the injector tube 975, provides the means to limit penetration of the needle 979.

While this description has focused on use of the INAS for use in ablation of tissue, it is also clearly envisioned that the apparatus and methods of FIGS. 1-33 can be applied to the use of this apparatus to inject any fluid for any purpose including that of local drug delivery into a specified portion of a blood vessel or the volume of tissue just outside of a blood vessel.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A method comprising:
   providing a system comprising a catheter body, a first guide tube, a second guide tube, a third guide tube, a first injection needle, a second injection needle, and a third injection needle, the first injection needle disposed within a lumen of the first guide tube, the second injection needle disposed within a lumen of the second guide tube, the third injection needle disposed within a lumen of the third guide tube;
   simultaneously advancing the first guide tube, the second guide tube, and the third guide tube to curve outward toward a target wall of a target vessel but not penetrate the target wall of the target vessel;
   simultaneously advancing the first injection needle, the second injection needle, and the third injection needle to penetrate the target wall, guided by the first guide tube, the second guide tube, and the third guide tube, each injection needle extending beyond the respective guide tube until further advancement of the injection needles is prevented; and
   delivering an ablative fluid through the first injection needle, the second injection needle, and the third injection needle to form an ablation zone of ablative fluid for each injection needle, wherein the ablation zones of ablative fluid intersect to form an ablative ring of ablative fluid around a circumference of the target vessel.

2. The method of claim 1, further including visualization of a radiopaque marker.

3. The method of claim 1, further including visualization of a radiopaque marker of the first guide tube.

4. The method of claim 1, further including visualization of a radiopaque marker of the first injection needle.

5. The method of claim 1, further including visualization of a radiopaque wire within the first injection needle.

6. The method of claim 1, further including evaluating electrical activity with the first injection needle.

7. The method of claim 1, further including measuring electrical activity within the target wall with the first injection needle.

8. The method of claim 1, wherein the first and second injection needles advance at least 0.5 mm beyond the respective guide tubes.

9. The method of claim 1, wherein the first and second injection needles advance between 0.5 mm and 4 mm beyond the respective guide tubes.

10. The method of claim 1, wherein the first and second injection needles advance between 2 mm and 3 mm beyond the respective guide tubes.

11. A method comprising:
    providing a system comprising a catheter body, a first guide tube, a second guide tube, a third guide tube, a first injection needle, a second injection needle, and a third injection needle, the first injection needle disposed within a lumen of the first guide tube, the second injection needle disposed within a lumen of the second guide tube, the third injection needle disposed within a lumen of the third guide tube;
    simultaneously advancing the first guide tube, the second guide tube, and the third guide tube to curve outward against a target wall but not penetrate the target wall;
    simultaneously advancing the first injection needle, the second injection needle, and the third injection needle relative to and within the lumens of the first guide tube, the second guide tube, and the third guide tube, respectively, to penetrate the target wall, each injection needle extending beyond the respective guide tube to penetrate the target wall at a preset distance; and
    delivering an ablative fluid through the first injection needle, the second injection needle, and the third injection needle to produce a ring of ablative fluid causing circumferential damage in nerve tissue near the target wall.

12. The method of claim 11, further including visualization of the first guide tube, the second guide tube, or the first and second guide tubes.

13. The method of claim 11, further including visualization of the first injection needle, the second injection needle, or the first and second injection needles.

14. The method of claim 11, wherein the preset distance is 0.5 mm.

15. The method of claim 11, wherein the preset distance is between 0.5 mm and 4 mm.

16. The method of claim 11, wherein the preset distance is between 2 mm and 3 mm.

17. The method of claim 11, wherein the preset distance is determined prior to advancing the system in a body of a patient.

18. The method of claim 11, wherein the preset distance is determined by a measurement of anatomy of a patient.

19. A method comprising:
    providing a system comprising a catheter body, three guide tubes, three injection needles, each injection needle adapted to move distally and proximally relative to and within a lumen of a respective guide tube of the three guide tubes;
    simultaneously advancing the three guide tubes against a target wall but not penetrate the target wall;
    simultaneously advancing the three injection needles, each injection needle advancing relative to the respective guide tube of the three guide tubes to penetrate the target wall, each injection needle extending beyond the respective guide tube up to a maximum distance; and
    delivering an ablative fluid through the three injection needles to form a ring of ablative fluid causing ablation of sympathetic nerve fibers beyond the target wall.

20. The method of claim 19, wherein each injection needle advances at least 0.5 mm beyond the respective guide tube.

* * * * *